(12) United States Patent
Peck et al.

(10) Patent No.: US 10,936,953 B2
(45) Date of Patent: Mar. 2, 2021

(54) DNA-BASED DIGITAL INFORMATION STORAGE WITH SIDEWALL ELECTRODES

(71) Applicant: Twist Bioscience Corporation, San Francisco, CA (US)

(72) Inventors: Bill James Peck, Santa Clara, CA (US); Brian Wayne Bramlett, Portland, OR (US)

(73) Assignee: Twist Bioscience Corporation, San Francisco, CA (US)

( * ) Notice: Subject to any disclaimer, the term of this patent is extended or adjusted under 35 U.S.C. 154(b) by 0 days.

(21) Appl. No.: 16/239,453

(22) Filed: Jan. 3, 2019

(65) Prior Publication Data

US 2019/0244109 A1 Aug. 8, 2019

Related U.S. Application Data

(60) Provisional application No. 62/613,728, filed on Jan. 4, 2018, provisional application No. 62/617,067, filed
(Continued)

(51) Int. Cl.
*G06N 3/12* (2006.01)
*G06F 17/40* (2006.01)
(Continued)

(52) U.S. Cl.
CPC ............ *G06N 3/123* (2013.01); *C12N 15/09* (2013.01); *C12N 15/1068* (2013.01);
(Continued)

(58) Field of Classification Search
CPC ......... G06N 3/123; G16B 50/20; G11C 11/00
See application file for complete search history.

(56) References Cited

U.S. PATENT DOCUMENTS 3,549,368 A 12/1970 Robert et al.
3,920,714 A 11/1975 Streck
(Continued)

FOREIGN PATENT DOCUMENTS

AU 3157000 A 9/2000
CA 2362939 A1 8/2000
(Continued)

OTHER PUBLICATIONS

Abudayyeh et al., C2c2 is a single-component programmable RNA-guided RNA-targeting CRISPR effector. Science, available on line, Jun. 13, 2016, at: http://zlab.mit.edu/assets/reprints/Abudayyeh_OO_Science_2016.pdf , 17 pages.
(Continued)

*Primary Examiner* — Mushfique Siddique
(74) *Attorney, Agent, or Firm* — Wilson Sonsini Goodrich & Rosati

(57) ABSTRACT

Provided herein are compositions, devices, systems and methods for generation and use of biomolecule-based information for storage. Further provided are devices-having addressable electrodes controlling polynucleotide synthesis (deprotection, extension, or cleavage, etc.) The compositions, devices, systems and methods described herein provide improved storage, density, and retrieval of biomolecule-based information.

14 Claims, 19 Drawing Sheets

Related U.S. Application Data on Jan. 12, 2018, provisional application No. 62/650,321, filed on Mar. 29, 2018.

(51) Int. Cl.

| | | |
|---|---|---|
| *G11C 13/02* | (2006.01) | |
| *G16B 50/20* | (2019.01) | |
| *C12N 15/10* | (2006.01) | |
| *G11C 13/00* | (2006.01) | |
| *G06N 99/00* | (2019.01) | |
| *G11C 11/56* | (2006.01) | |
| *G11C 11/00* | (2006.01) | |
| *C12N 15/09* | (2006.01) | |
| *G06F 16/00* | (2019.01) | |
| *G16B 30/00* | (2019.01) | |

(52) U.S. Cl.
CPC .......... *G06F 17/40* (2013.01); *G06N 99/007* (2013.01); *G11C 11/00* (2013.01); *G11C 11/56* (2013.01); *G11C 13/0019* (2013.01); *G11C 13/02* (2013.01); *G16B 50/20* (2019.02); *G06F 16/00* (2019.01); *G16B 30/00* (2019.02)

(56) References Cited

U.S. PATENT DOCUMENTS

| | | |
|---|---|---|
| 4,123,661 A | 10/1978 | Wolf et al. |
| 4,415,732 A | 11/1983 | Caruthers et al. |
| 4,613,398 A | 9/1986 | Chiong et al. |
| 4,726,877 A | 2/1988 | Fryd et al. |
| 4,808,511 A | 2/1989 | Holmes |
| 4,837,401 A | 6/1989 | Hirose et al. |
| 4,863,557 A | 9/1989 | Kokaku et al. |
| 4,981,797 A | 1/1991 | Jessee et al. |
| 4,988,617 A | 1/1991 | Landegren et al. |
| 5,102,797 A | 4/1992 | Tucker et al. |
| 5,118,605 A | 6/1992 | Urdea |
| 5,137,814 A | 8/1992 | Rashtchian et al. |
| 5,143,854 A | 9/1992 | Pirrung et al. |
| 5,242,794 A | 9/1993 | Whiteley et al. |
| 5,242,974 A | 9/1993 | Holmes |
| 5,288,514 A | 2/1994 | Ellman et al. |
| 5,291,897 A | 3/1994 | Gastrin et al. |
| 5,299,491 A | 4/1994 | Kawada |
| 5,384,261 A | 1/1995 | Winkler et al. |
| 5,387,541 A | 2/1995 | Hodge et al. |
| 5,395,753 A | 3/1995 | Prakash |
| 5,431,720 A | 7/1995 | Nagai et al. |
| 5,445,934 A | 8/1995 | Fodor et al. |
| 5,449,754 A | 9/1995 | Nishioka |
| 5,459,039 A | 10/1995 | Modrich et al. |
| 5,474,796 A | 12/1995 | Brennan |
| 5,476,930 A | 12/1995 | Letsinger et al. |
| 5,487,993 A | 1/1996 | Herrnstadt et al. |
| 5,494,810 A | 2/1996 | Barany et al. |
| 5,501,893 A | 3/1996 | Laermer et al. |
| 5,508,169 A | 4/1996 | Deugau et al. |
| 5,510,270 A | 4/1996 | Fodor et al. |
| 5,514,789 A | 5/1996 | Kempe |
| 5,527,681 A | 6/1996 | Holmes et al. |
| 5,530,516 A | 6/1996 | Sheets |
| 5,556,750 A | 9/1996 | Modrich et al. |
| 5,586,211 A | 12/1996 | Dumitrou et al. |
| 5,641,658 A | 6/1997 | Adams et al. |
| 5,677,195 A | 10/1997 | Winkler et al. |
| 5,679,522 A | 10/1997 | Modrich et al. |
| 5,683,879 A | 11/1997 | Laney et al. |
| 5,688,642 A | 11/1997 | Chrisey et al. |
| 5,700,637 A | 12/1997 | Southern et al. |
| 5,700,642 A | 12/1997 | Monforte et al. |
| 5,702,894 A | 12/1997 | Modrich et al. |
| 5,707,806 A | 1/1998 | Shuber |
| 5,712,124 A | 1/1998 | Walker |
| 5,739,386 A | 4/1998 | Holmes |
| 5,750,672 A | 5/1998 | Kempe |
| 5,780,613 A | 7/1998 | Letsinger et al. |
| 5,830,643 A | 11/1998 | Yamamoto et al. |
| 5,830,655 A | 11/1998 | Monforte et al. |
| 5,830,662 A | 11/1998 | Soares et al. |
| 5,834,252 A | 11/1998 | Stemmer et al. |
| 5,843,669 A | 12/1998 | Kaiser et al. |
| 5,843,767 A | 12/1998 | Beattie |
| 5,846,717 A | 12/1998 | Brow et al. |
| 5,854,033 A | 12/1998 | Lizardi |
| 5,858,754 A | 1/1999 | Modrich et al. |
| 5,861,482 A | 1/1999 | Modrich et al. |
| 5,863,801 A | 1/1999 | Southgate et al. |
| 5,869,245 A | 2/1999 | Yeung |
| 5,877,280 A | 3/1999 | Wetmur |
| 5,882,496 A | 3/1999 | Northrup et al. |
| 5,922,539 A | 7/1999 | Modrich et al. |
| 5,922,593 A | 7/1999 | Livingston |
| 5,928,907 A | 7/1999 | Woudenberg et al. |
| 5,962,272 A | 10/1999 | Chenchik et al. |
| 5,976,842 A | 11/1999 | Wurst |
| 5,976,846 A | 11/1999 | Passmore et al. |
| 5,989,872 A | 11/1999 | Luo et al. |
| 5,994,069 A | 11/1999 | Hall et al. |
| 6,001,567 A | 12/1999 | Brow et al. |
| 6,008,031 A | 12/1999 | Modrich et al. |
| 6,013,440 A | 1/2000 | Lipshutz et al. |
| 6,015,674 A | 1/2000 | Woudenberg et al. |
| 6,017,434 A | 1/2000 | Simpson et al. |
| 6,020,481 A | 2/2000 | Benson et al. |
| 6,027,898 A | 2/2000 | Gjerde et al. |
| 6,028,189 A | 2/2000 | Blanchard |
| 6,028,198 A | 2/2000 | Liu et al. |
| 6,040,138 A | 3/2000 | Lockhart et al. |
| 6,077,674 A | 6/2000 | Schleifer et al. |
| 6,087,482 A | 7/2000 | Teng et al. |
| 6,090,543 A | 7/2000 | Prudent et al. |
| 6,090,606 A | 7/2000 | Kaiser et al. |
| 6,103,474 A | 8/2000 | Dellinger et al. |
| 6,107,038 A | 8/2000 | Choudhary et al. |
| 6,110,682 A | 8/2000 | Dellinger et al. |
| 6,114,115 A | 9/2000 | Wagner, Jr. |
| 6,130,045 A | 10/2000 | Wurst et al. |
| 6,132,997 A | 10/2000 | Shannon |
| 6,136,568 A | 10/2000 | Hiatt et al. |
| 6,171,797 B1 | 1/2001 | Perbost |
| 6,180,351 B1 | 1/2001 | Cattell |
| 6,201,112 B1 | 3/2001 | Ach |
| 6,218,118 B1 | 4/2001 | Sampson et al. |
| 6,221,653 B1 | 4/2001 | Caren et al. |
| 6,222,030 B1 | 4/2001 | Dellinger et al. |
| 6,232,072 B1 | 5/2001 | Fisher |
| 6,235,483 B1 | 5/2001 | Wolber et al. |
| 6,242,266 B1 | 6/2001 | Schleifer et al. |
| 6,251,588 B1 | 6/2001 | Shannon et al. |
| 6,251,595 B1 | 6/2001 | Gordon et al. |
| 6,251,685 B1 | 6/2001 | Dorsel et al. |
| 6,258,454 B1 | 7/2001 | Lefkowitz et al. |
| 6,262,490 B1 | 7/2001 | Hsu et al. |
| 6,274,725 B1 | 8/2001 | Sanghvi et al. |
| 6,284,465 B1 | 9/2001 | Wolber |
| 6,287,776 B1 | 9/2001 | Hefti |
| 6,287,824 B1 | 9/2001 | Lizardi |
| 6,297,017 B1 | 10/2001 | Schmidt et al. |
| 6,300,137 B1 | 10/2001 | Earhart et al. |
| 6,306,599 B1 | 10/2001 | Perbost |
| 6,309,822 B1 | 10/2001 | Fodor et al. |
| 6,309,828 B1 | 10/2001 | Schleifer et al. |
| 6,312,911 B1 | 11/2001 | Bancroft et al. |
| 6,319,674 B1 | 11/2001 | Fulcrand et al. |
| 6,323,043 B1 | 11/2001 | Caren et al. |
| 6,329,210 B1 | 12/2001 | Schleifer |
| 6,346,423 B1 | 2/2002 | Schembri |
| 6,365,355 B1 | 4/2002 | McCutchen-Maloney |
| 6,372,483 B2 | 4/2002 | Schleifer et al. |
| 6,375,903 B1 | 4/2002 | Cerrina et al. |
| 6,376,285 B1 | 4/2002 | Joyner et al. |
| 6,384,210 B1 | 5/2002 | Blanchard |
| 6,387,636 B1 | 5/2002 | Perbost et al. |

(56) References Cited

U.S. PATENT DOCUMENTS

| | | |
|---|---|---|
| 6,399,394 B1 | 6/2002 | Dahm et al. |
| 6,399,516 B1 | 6/2002 | Ayon |
| 6,403,314 B1 | 6/2002 | Lange et al. |
| 6,406,849 B1 | 6/2002 | Dorsel et al. |
| 6,406,851 B1 | 6/2002 | Bass |
| 6,408,308 B1 | 6/2002 | Maslyn et al. |
| 6,419,883 B1 | 7/2002 | Blanchard |
| 6,428,957 B1 | 8/2002 | Delenstarr |
| 6,440,669 B1 | 8/2002 | Bass et al. |
| 6,444,268 B2 | 9/2002 | Lefkowitz et al. |
| 6,446,642 B1 | 9/2002 | Caren et al. |
| 6,446,682 B1 | 9/2002 | Viken |
| 6,451,998 B1 | 9/2002 | Perbost |
| 6,458,526 B1 | 10/2002 | Schembri et al. |
| 6,458,535 B1 | 10/2002 | Hall et al. |
| 6,458,583 B1 | 10/2002 | Bruhn et al. |
| 6,461,812 B2 | 10/2002 | Barth et al. |
| 6,461,816 B1 | 10/2002 | Wolber et al. |
| 6,469,156 B1 | 10/2002 | Schafer et al. |
| 6,472,147 B1 | 10/2002 | Janda et al. |
| 6,492,107 B1 | 12/2002 | Kauffman et al. |
| 6,518,056 B2 | 2/2003 | Schembri et al. |
| 6,521,427 B1 | 2/2003 | Evans |
| 6,521,453 B1 | 2/2003 | Crameri et al. |
| 6,555,357 B1 | 4/2003 | Kaiser et al. |
| 6,558,908 B2 | 5/2003 | Wolber et al. |
| 6,562,611 B1 | 5/2003 | Kaiser et al. |
| 6,566,495 B1 | 5/2003 | Fodor et al. |
| 6,582,908 B2 | 6/2003 | Fodor et al. |
| 6,582,938 B1 | 6/2003 | Su et al. |
| 6,586,211 B1 | 7/2003 | Staehler et al. |
| 6,587,579 B1 | 7/2003 | Bass |
| 6,589,739 B2 | 7/2003 | Fisher |
| 6,599,693 B1 | 7/2003 | Webb |
| 6,602,472 B1 | 8/2003 | Zimmermann et al. |
| 6,610,978 B2 | 8/2003 | Yin et al. |
| 6,613,513 B1 | 9/2003 | Parce et al. |
| 6,613,523 B2 | 9/2003 | Fischer |
| 6,613,560 B1 | 9/2003 | Tso et al. |
| 6,613,893 B1 | 9/2003 | Webb |
| 6,621,076 B1 | 9/2003 | Van De Goor et al. |
| 6,630,581 B2 | 10/2003 | Dellinger et al. |
| 6,632,641 B1 | 10/2003 | Brennan et al. |
| 6,635,226 B1 | 10/2003 | Tso et al. |
| 6,642,373 B2 | 11/2003 | Manoharan et al. |
| 6,649,348 B2 | 11/2003 | Bass et al. |
| 6,660,338 B1 | 12/2003 | Hargreaves |
| 6,664,112 B2 | 12/2003 | Mulligan et al. |
| 6,670,127 B2 | 12/2003 | Evans |
| 6,670,461 B1 | 12/2003 | Wengel et al. |
| 6,673,552 B2 | 1/2004 | Frey |
| 6,682,702 B2 | 1/2004 | Barth et al. |
| 6,689,319 B1 | 2/2004 | Fisher et al. |
| 6,692,917 B2 | 2/2004 | Neri et al. |
| 6,702,256 B2 | 3/2004 | Killeen et al. |
| 6,706,471 B1 | 3/2004 | Brow et al. |
| 6,706,875 B1 | 3/2004 | Goldberg et al. |
| 6,709,852 B1 | 3/2004 | Bloom et al. |
| 6,709,854 B2 | 3/2004 | Donahue et al. |
| 6,713,262 B2 | 3/2004 | Gillibolian et al. |
| 6,716,629 B2 | 4/2004 | Hess et al. |
| 6,716,634 B1 | 4/2004 | Myerson |
| 6,723,509 B2 | 4/2004 | Ach |
| 6,728,129 B2 | 4/2004 | Lindsey et al. |
| 6,743,585 B2 | 6/2004 | Dellinger et al. |
| 6,753,145 B2 | 6/2004 | Holcomb et al. |
| 6,768,005 B2 | 7/2004 | Mellor et al. |
| 6,770,748 B2 | 8/2004 | Imanishi et al. |
| 6,770,892 B2 | 8/2004 | Corson et al. |
| 6,773,676 B2 | 8/2004 | Schembri |
| 6,773,888 B2 | 8/2004 | Li et al. |
| 6,780,982 B2 | 8/2004 | Lyamichev et al. |
| 6,787,308 B2 | 9/2004 | Balasubramanian et al. |
| 6,789,965 B2 | 9/2004 | Barth et al. |
| 6,790,620 B2 | 9/2004 | Bass et al. |
| 6,794,499 B2 | 9/2004 | Wengel et al. |
| 6,796,634 B2 | 9/2004 | Caren et al. |
| 6,800,439 B1 | 10/2004 | McGall et al. |
| 6,814,846 B1 | 11/2004 | Berndt |
| 6,815,218 B1 | 11/2004 | Jacobson et al. |
| 6,824,866 B1 | 11/2004 | Glazer et al. |
| 6,830,890 B2 | 12/2004 | Lockhart et al. |
| 6,833,246 B2 | 12/2004 | Balasubramanian |
| 6,833,450 B1 | 12/2004 | McGall et al. |
| 6,835,938 B2 | 12/2004 | Ghosh et al. |
| 6,838,888 B2 | 1/2005 | Peck |
| 6,841,131 B2 | 1/2005 | Zimmermann et al. |
| 6,845,968 B2 | 1/2005 | Killeen et al. |
| 6,846,454 B2 | 1/2005 | Peck |
| 6,846,922 B1 | 1/2005 | Manoharan et al. |
| 6,852,850 B2 | 2/2005 | Myerson et al. |
| 6,858,720 B2 | 2/2005 | Myerson et al. |
| 6,879,915 B2 | 4/2005 | Cattell |
| 6,880,576 B2 | 4/2005 | Karp et al. |
| 6,884,580 B2 | 4/2005 | Caren et al. |
| 6,887,715 B2 | 5/2005 | Schembri |
| 6,890,723 B2 | 5/2005 | Perbost et al. |
| 6,890,760 B1 | 5/2005 | Webb |
| 6,893,816 B1 | 5/2005 | Beattie |
| 6,897,023 B2 | 5/2005 | Fu et al. |
| 6,900,047 B2 | 5/2005 | Bass |
| 6,900,048 B2 | 5/2005 | Perbost |
| 6,911,611 B2 | 6/2005 | Wong et al. |
| 6,914,229 B2 | 7/2005 | Corson et al. |
| 6,916,113 B2 | 7/2005 | Van De Goor et al. |
| 6,916,633 B1 | 7/2005 | Shannon |
| 6,919,181 B2 | 7/2005 | Hargreaves |
| 6,927,029 B2 | 8/2005 | Lefkowitz et al. |
| 6,929,951 B2 | 8/2005 | Corson et al. |
| 6,936,472 B2 | 8/2005 | Earhart et al. |
| 6,938,476 B2 | 9/2005 | Chesk |
| 6,939,673 B2 | 9/2005 | Bass et al. |
| 6,943,036 B2 | 9/2005 | Bass |
| 6,946,285 B2 | 9/2005 | Bass |
| 6,950,756 B2 | 9/2005 | Kincaid |
| 6,951,719 B1 | 10/2005 | Dupret et al. |
| 6,958,119 B2 | 10/2005 | Yin et al. |
| 6,960,464 B2 | 11/2005 | Jessee et al. |
| 6,969,449 B2 | 11/2005 | Maher et al. |
| 6,969,488 B2 | 11/2005 | Bridgham et al. |
| 6,976,384 B2 | 12/2005 | Hobbs et al. |
| 6,977,223 B2 | 12/2005 | George et al. |
| 6,987,263 B2 | 1/2006 | Hobbs et al. |
| 6,989,267 B2 | 1/2006 | Kim et al. |
| 6,991,922 B2 | 1/2006 | Dupret et al. |
| 7,008,037 B2 | 3/2006 | Caren et al. |
| 7,025,324 B1 | 4/2006 | Slocum et al. |
| 7,026,124 B2 | 4/2006 | Barth et al. |
| 7,027,930 B2 | 4/2006 | Cattell |
| 7,028,536 B2 | 4/2006 | Karp et al. |
| 7,029,854 B2 | 4/2006 | Collins et al. |
| 7,034,290 B2 | 4/2006 | Lu et al. |
| 7,041,445 B2 | 5/2006 | Chenchik et al. |
| 7,045,289 B2 | 5/2006 | Allawi et al. |
| 7,051,574 B2 | 5/2006 | Peck |
| 7,052,841 B2 | 5/2006 | Delenstarr |
| 7,062,385 B2 | 6/2006 | White et al. |
| 7,064,197 B1 | 6/2006 | Rabbani et al. |
| 7,070,932 B2 | 7/2006 | Leproust et al. |
| 7,075,161 B2 | 7/2006 | Barth |
| 7,078,167 B2 | 7/2006 | Delenstarr et al. |
| 7,078,505 B2 | 7/2006 | Bass et al. |
| 7,094,537 B2 | 8/2006 | Leproust et al. |
| 7,097,974 B1 | 8/2006 | Staehler et al. |
| 7,101,508 B2 | 9/2006 | Thompson et al. |
| 7,101,986 B2 | 9/2006 | Dellinger et al. |
| 7,105,295 B2 | 9/2006 | Bass et al. |
| 7,115,423 B1 | 10/2006 | Mitchell |
| 7,122,303 B2 | 10/2006 | Delenstarr et al. |
| 7,122,364 B1 | 10/2006 | Lyamichev et al. |
| 7,125,488 B2 | 10/2006 | Li |
| 7,125,523 B2 | 10/2006 | Sillman |
| 7,128,876 B2 | 10/2006 | Yin et al. |
| 7,129,075 B2 | 10/2006 | Gerard et al. |

(56) References Cited

U.S. PATENT DOCUMENTS

| | | | |
|---|---|---|---|
| 7,135,565 B2 | 11/2006 | Dellinger et al. |
| 7,138,062 B2 | 11/2006 | Yin et al. |
| 7,141,368 B2 | 11/2006 | Fisher et al. |
| 7,141,807 B2 | 11/2006 | Joyce et al. |
| 7,147,362 B2 | 12/2006 | Caren et al. |
| 7,150,982 B2 | 12/2006 | Allawi et al. |
| 7,153,689 B2 | 12/2006 | Tolosko et al. |
| 7,163,660 B2 | 1/2007 | Lehmann |
| 7,166,258 B2 | 1/2007 | Bass et al. |
| 7,179,659 B2 | 2/2007 | Stolowitz et al. |
| 7,183,406 B2 | 2/2007 | Belshaw et al. |
| 7,192,710 B2 | 3/2007 | Gellibolian et al. |
| 7,193,077 B2 | 3/2007 | Dellinger et al. |
| 7,198,939 B2 | 4/2007 | Dorsel et al. |
| 7,202,264 B2 | 4/2007 | Ravikumar et al. |
| 7,202,358 B2 | 4/2007 | Hargreaves |
| 7,205,128 B2 | 4/2007 | Ilsley et al. |
| 7,205,400 B2 | 4/2007 | Webb |
| 7,206,439 B2 | 4/2007 | Zhou et al. |
| 7,208,322 B2 | 4/2007 | Stolowitz et al. |
| 7,217,522 B2 | 5/2007 | Brenner |
| 7,220,573 B2 | 5/2007 | Shea et al. |
| 7,221,785 B2 | 5/2007 | Curry et al. |
| 7,226,862 B2 | 6/2007 | Staehler et al. |
| 7,227,017 B2 | 6/2007 | Mellor et al. |
| 7,229,497 B2 | 6/2007 | Stott et al. |
| 7,247,337 B1 | 7/2007 | Leproust et al. |
| 7,247,497 B2 | 7/2007 | Dahm et al. |
| 7,252,938 B2 | 8/2007 | Leproust et al. |
| 7,269,518 B2 | 9/2007 | Corson |
| 7,271,258 B2 | 9/2007 | Dellinger et al. |
| 7,276,336 B1 | 10/2007 | Webb et al. |
| 7,276,378 B2 | 10/2007 | Myerson |
| 7,276,599 B2 | 10/2007 | Moore et al. |
| 7,282,183 B2 | 10/2007 | Peck |
| 7,282,332 B2 | 10/2007 | Caren et al. |
| 7,282,705 B2 | 10/2007 | Brennen |
| 7,291,471 B2 | 11/2007 | Sampson et al. |
| 7,302,348 B2 | 11/2007 | Ghosh et al. |
| 7,306,917 B2 | 12/2007 | Prudent et al. |
| 7,314,599 B2 | 1/2008 | Roitman et al. |
| 7,323,320 B2 | 1/2008 | Oleinikov |
| 7,344,831 B2 | 3/2008 | Wolber et al. |
| 7,348,144 B2 | 3/2008 | Minor |
| 7,351,379 B2 | 4/2008 | Schleifer |
| 7,353,116 B2 | 4/2008 | Webb et al. |
| 7,361,906 B2 | 4/2008 | Ghosh et al. |
| 7,364,896 B2 | 4/2008 | Schembri |
| 7,368,550 B2 | 5/2008 | Dellinger et al. |
| 7,371,348 B2 | 5/2008 | Schleifer et al. |
| 7,371,519 B2 | 5/2008 | Wolber et al. |
| 7,371,580 B2 | 5/2008 | Yakhini et al. |
| 7,372,982 B2 | 5/2008 | Le Cocq |
| 7,384,746 B2 | 6/2008 | Lyamichev et al. |
| 7,385,050 B2 | 6/2008 | Dellinger et al. |
| 7,390,457 B2 | 6/2008 | Schembri |
| 7,393,665 B2 | 7/2008 | Brenner |
| 7,396,676 B2 | 7/2008 | Robotti et al. |
| 7,399,844 B2 | 7/2008 | Sampson et al. |
| 7,402,279 B2 | 7/2008 | Schembri |
| 7,411,061 B2 | 8/2008 | Myerson et al. |
| 7,413,709 B2 | 8/2008 | Roitman et al. |
| 7,417,139 B2 | 8/2008 | Dellinger et al. |
| 7,422,911 B2 | 9/2008 | Schembri |
| 7,427,679 B2 | 9/2008 | Dellinger et al. |
| 7,432,048 B2 | 10/2008 | Neri et al. |
| 7,435,810 B2 | 10/2008 | Myerson et al. |
| 7,439,272 B2 | 10/2008 | Xu |
| 7,476,709 B2 | 1/2009 | Moody et al. |
| 7,482,118 B2 | 1/2009 | Allawi et al. |
| 7,488,607 B2 | 2/2009 | Tom-Moy et al. |
| 7,504,213 B2 | 3/2009 | Sana et al. |
| 7,514,369 B2 | 4/2009 | Li et al. |
| 7,517,979 B2 | 4/2009 | Wolber |
| 7,524,942 B2 | 4/2009 | Wang et al. |
| 7,524,950 B2 | 4/2009 | Dellinger et al. |
| 7,527,928 B2 | 5/2009 | Neri et al. |
| 7,531,303 B2 | 5/2009 | Dorsel et al. |
| 7,534,561 B2 | 5/2009 | Sana et al. |
| 7,534,563 B2 | 5/2009 | Hargreaves |
| 7,537,936 B2 | 5/2009 | Dahm et al. |
| 7,541,145 B2 | 6/2009 | Prudent et al. |
| 7,544,473 B2 | 6/2009 | Brenner |
| 7,556,919 B2 | 7/2009 | Chenchik et al. |
| 7,563,600 B2 | 7/2009 | Oleinikov |
| 7,572,585 B2 | 8/2009 | Wang |
| 7,572,907 B2 | 8/2009 | Dellinger et al. |
| 7,572,908 B2 | 8/2009 | Dellinger et al. |
| 7,585,970 B2 | 9/2009 | Dellinger et al. |
| 7,588,889 B2 | 9/2009 | Wolber et al. |
| 7,595,350 B2 | 9/2009 | Xu |
| 7,604,941 B2 | 10/2009 | Jacobson |
| 7,604,996 B1 | 10/2009 | Stuelpnagel et al. |
| 7,608,396 B2 | 10/2009 | Delenstarr |
| 7,618,777 B2 | 11/2009 | Myerson et al. |
| 7,629,120 B2 | 12/2009 | Bennett et al. |
| 7,635,772 B2 | 12/2009 | McCormac |
| 7,648,832 B2 | 1/2010 | Jessee et al. |
| 7,651,762 B2 | 1/2010 | Xu et al. |
| 7,659,069 B2 | 2/2010 | Belyaev et al. |
| 7,678,542 B2 | 3/2010 | Lyamichev et al. |
| 7,682,809 B2 | 3/2010 | Sampson |
| 7,709,197 B2 | 5/2010 | Drmanac |
| 7,718,365 B2 | 5/2010 | Wang |
| 7,718,786 B2 | 5/2010 | Dupret et al. |
| 7,723,077 B2 | 5/2010 | Young et al. |
| 7,737,088 B1 | 6/2010 | Staehler et al. |
| 7,737,089 B2 | 6/2010 | Guimil et al. |
| 7,741,463 B2 | 6/2010 | Gormley et al. |
| 7,749,701 B2 | 7/2010 | Leproust et al. |
| 7,759,471 B2 | 7/2010 | Dellinger et al. |
| 7,776,021 B2 | 8/2010 | Borenstein et al. |
| 7,776,532 B2 | 8/2010 | Gibson et al. |
| 7,790,369 B2 | 9/2010 | Stahler et al. |
| 7,790,387 B2 | 9/2010 | Dellinger et al. |
| 7,807,356 B2 | 10/2010 | Sampson et al. |
| 7,807,806 B2 | 10/2010 | Allawi et al. |
| 7,811,753 B2 | 10/2010 | Eshoo |
| 7,816,079 B2 | 10/2010 | Fischer |
| 7,820,387 B2 | 10/2010 | Neri et al. |
| 7,829,314 B2 | 11/2010 | Prudent et al. |
| 7,855,281 B2 | 12/2010 | Dellinger et al. |
| 7,862,999 B2 | 1/2011 | Zheng et al. |
| 7,867,782 B2 | 1/2011 | Barth |
| 7,875,463 B2 | 1/2011 | Adaskin et al. |
| 7,879,541 B2 | 2/2011 | Kincaid |
| 7,879,580 B2 | 2/2011 | Carr et al. |
| 7,894,998 B2 | 2/2011 | Kincaid |
| 7,919,239 B2 | 4/2011 | Wang |
| 7,919,308 B2 | 4/2011 | Schleifer |
| 7,927,797 B2 | 4/2011 | Nobile et al. |
| 7,927,838 B2 | 4/2011 | Shannon |
| 7,932,025 B2 | 4/2011 | Carr et al. |
| 7,932,070 B2 | 4/2011 | Hogrefe et al. |
| 7,935,800 B2 | 5/2011 | Allawi et al. |
| 7,939,645 B2 | 5/2011 | Borns |
| 7,943,046 B2 | 5/2011 | Martosella et al. |
| 7,943,358 B2 | 5/2011 | Hogrefe et al. |
| 7,960,157 B2 | 6/2011 | Borns |
| 7,977,119 B2 | 7/2011 | Kronick et al. |
| 7,979,215 B2 | 7/2011 | Sampas |
| 7,998,437 B2 | 8/2011 | Berndt et al. |
| 7,999,087 B2 | 8/2011 | Dellinger et al. |
| 8,021,842 B2 | 9/2011 | Brenner |
| 8,021,844 B2 | 9/2011 | Wang |
| 8,034,917 B2 | 10/2011 | Yamada |
| 8,036,835 B2 | 10/2011 | Sampas et al. |
| 8,048,664 B2 | 11/2011 | Guan et al. |
| 8,053,191 B2 | 11/2011 | Blake |
| 8,058,001 B2 | 11/2011 | Crameri et al. |
| 8,058,004 B2 | 11/2011 | Oleinikov |
| 8,058,055 B2 | 11/2011 | Barrett et al. |
| 8,063,184 B2 | 11/2011 | Allawi et al. |
| 8,067,556 B2 | 11/2011 | Hogrefe et al. |

(56) References Cited

U.S. PATENT DOCUMENTS

| | | |
|---|---|---|
| 8,073,626 B2 | 12/2011 | Troup et al. |
| 8,076,064 B2 | 12/2011 | Wang |
| 8,076,152 B2 | 12/2011 | Robotti |
| 8,097,711 B2 | 1/2012 | Timar et al. |
| 8,137,936 B2 | 3/2012 | Macevicz |
| 8,148,068 B2 | 4/2012 | Brenner |
| 8,154,729 B2 | 4/2012 | Baldo et al. |
| 8,168,385 B2 | 5/2012 | Brenner et al. |
| 8,168,388 B2 | 5/2012 | Gormley et al. |
| 8,173,368 B2 | 5/2012 | Staehler et al. |
| 8,182,991 B1 | 5/2012 | Kaiser et al. |
| 8,194,244 B2 | 6/2012 | Wang et al. |
| 8,198,071 B2 | 6/2012 | Goshoo et al. |
| 8,202,983 B2 | 6/2012 | Dellinger et al. |
| 8,202,985 B2 | 6/2012 | Dellinger et al. |
| 8,206,952 B2 | 6/2012 | Carr et al. |
| 8,213,015 B2 | 7/2012 | Kraiczek et al. |
| 8,242,258 B2 | 8/2012 | Dellinger et al. |
| 8,247,221 B2 | 8/2012 | Fawcett et al. |
| 8,263,335 B2 | 9/2012 | Carr et al. |
| 8,268,605 B2 | 9/2012 | Sorge et al. |
| 8,283,148 B2 | 10/2012 | Sorge et al. |
| 8,288,093 B2 | 10/2012 | Hall et al. |
| 8,298,767 B2 | 10/2012 | Brenner et al. |
| 8,304,273 B2 | 11/2012 | Stellacci et al. |
| 8,309,307 B2 | 11/2012 | Barrett et al. |
| 8,309,706 B2 | 11/2012 | Dellinger et al. |
| 8,309,710 B2 | 11/2012 | Sierzchala et al. |
| 8,314,220 B2 | 11/2012 | Mullinax et al. |
| 8,318,433 B2 | 11/2012 | Brenner |
| 8,318,479 B2 | 11/2012 | Domansky et al. |
| 8,357,489 B2 | 1/2013 | Chua et al. |
| 8,357,490 B2 | 1/2013 | Froehlich et al. |
| 8,367,016 B2 | 2/2013 | Quan et al. |
| 8,367,335 B2 | 2/2013 | Staehler et al. |
| 8,380,441 B2 | 2/2013 | Webb et al. |
| 8,383,338 B2 | 2/2013 | Kitzman et al. |
| 8,415,138 B2 | 4/2013 | Leproust |
| 8,435,736 B2 | 5/2013 | Gibson et al. |
| 8,445,205 B2 | 5/2013 | Brenner |
| 8,445,206 B2 | 5/2013 | Bergmann et al. |
| 8,470,996 B2 | 6/2013 | Brenner et al. |
| 8,476,018 B2 | 7/2013 | Brenner |
| 8,476,598 B1 | 7/2013 | Pralle et al. |
| 8,481,292 B2 | 7/2013 | Casbon et al. |
| 8,481,309 B2 | 7/2013 | Zhang et al. |
| 8,491,561 B2 | 7/2013 | Borenstein et al. |
| 8,497,069 B2 | 7/2013 | Hutchison, III et al. |
| 8,500,979 B2 | 8/2013 | Elibol et al. |
| 8,501,454 B2 | 8/2013 | Liu et al. |
| 8,507,226 B2 | 8/2013 | Carr et al. |
| 8,507,239 B2 | 8/2013 | Lubys et al. |
| 8,507,272 B2 | 8/2013 | Zhang et al. |
| 8,530,197 B2 | 9/2013 | Li et al. |
| 8,552,174 B2 | 10/2013 | Dellinger et al. |
| 8,563,478 B2 | 10/2013 | Gormley et al. |
| 8,569,046 B2 | 10/2013 | Love et al. |
| 8,577,621 B2 | 11/2013 | Troup et al. |
| 8,586,310 B2 | 11/2013 | Mitra et al. |
| 8,614,092 B2 | 12/2013 | Zhang et al. |
| 8,642,755 B2 | 2/2014 | Sierzchala et al. |
| 8,664,164 B2 | 3/2014 | Ericsson et al. |
| 8,669,053 B2 | 3/2014 | Stuelpnagel et al. |
| 8,679,756 B1 | 3/2014 | Brenner et al. |
| 8,685,642 B2 | 4/2014 | Sampas |
| 8,685,676 B2 | 4/2014 | Hogrefe et al. |
| 8,685,678 B2 | 4/2014 | Casbon et al. |
| 8,715,933 B2 | 5/2014 | Oliver |
| 8,715,967 B2 | 5/2014 | Casbon et al. |
| 8,716,467 B2 | 5/2014 | Jacobson |
| 8,722,368 B2 | 5/2014 | Casbon et al. |
| 8,722,585 B2 | 5/2014 | Wang |
| 8,728,766 B2 | 5/2014 | Casbon et al. |
| 8,741,606 B2 | 6/2014 | Casbon et al. |
| 8,808,896 B2 | 8/2014 | Choo et al. |
| 8,808,986 B2 | 8/2014 | Jacobson et al. |
| 8,815,600 B2 | 8/2014 | Liu et al. |
| 8,889,851 B2 | 11/2014 | Leproust et al. |
| 8,932,994 B2 | 1/2015 | Gormley et al. |
| 8,962,532 B2 | 2/2015 | Shapiro et al. |
| 8,968,999 B2 | 3/2015 | Gibson et al. |
| 8,980,563 B2 | 3/2015 | Zheng et al. |
| 9,018,365 B2 | 4/2015 | Brenner et al. |
| 9,023,601 B2 | 5/2015 | Oleinikov |
| 9,051,666 B2 | 6/2015 | Oleinikov |
| 9,073,962 B2 | 7/2015 | Fracchia et al. |
| 9,074,204 B2 | 7/2015 | Anderson et al. |
| 9,085,797 B2 | 7/2015 | Gebeyehu et al. |
| 9,133,510 B2 | 9/2015 | Andersen et al. |
| 9,139,874 B2 | 9/2015 | Myers et al. |
| 9,150,853 B2 | 10/2015 | Hudson et al. |
| 9,187,777 B2 | 11/2015 | Jacobson et al. |
| 9,194,001 B2 | 11/2015 | Brenner |
| 9,216,414 B2 | 12/2015 | Chu |
| 9,217,144 B2 | 12/2015 | Jacobson et al. |
| 9,279,149 B2 | 3/2016 | Efcavitch et al. |
| 9,286,439 B2 | 3/2016 | Shapiro et al. |
| 9,295,965 B2 | 3/2016 | Jacobson et al. |
| 9,315,861 B2 | 4/2016 | Hendricks et al. |
| 9,328,378 B2 | 5/2016 | Earnshaw et al. |
| 9,347,091 B2 | 5/2016 | Bergmann et al. |
| 9,375,748 B2 | 6/2016 | Harumoto et al. |
| 9,376,677 B2 | 6/2016 | Mir et al. |
| 9,376,678 B2 | 6/2016 | Gormley et al. |
| 9,384,320 B2 | 7/2016 | Church |
| 9,384,920 B1 | 7/2016 | Bakulich |
| 9,388,407 B2 | 7/2016 | Jacobson |
| 9,394,333 B2 | 7/2016 | Wada et al. |
| 9,403,141 B2 | 8/2016 | Banyai et al. |
| 9,409,139 B2 * | 8/2016 | Banyai ............... B01J 19/0046 |
| 9,410,149 B2 | 8/2016 | Brenner et al. |
| 9,410,173 B2 | 8/2016 | Betts et al. |
| 9,416,411 B2 | 8/2016 | Stuelpnagel et al. |
| 9,422,600 B2 | 8/2016 | Ramu et al. |
| 9,487,824 B2 | 11/2016 | Kutyavin et al. |
| 9,499,848 B2 | 11/2016 | Carr et al. |
| 9,523,122 B2 | 12/2016 | Zheng et al. |
| 9,528,148 B2 | 12/2016 | Zheng et al. |
| 9,534,251 B2 | 1/2017 | Young et al. |
| 9,555,388 B2 | 1/2017 | Banyai et al. |
| 9,568,839 B2 | 2/2017 | Stahler et al. |
| 9,580,746 B2 | 2/2017 | Leproust et al. |
| 9,670,529 B2 | 6/2017 | Osborne et al. |
| 9,670,536 B2 | 6/2017 | Casbon et al. |
| 9,677,067 B2 | 6/2017 | Toro |
| 9,695,211 B2 | 7/2017 | Wada et al. |
| 9,718,060 B2 | 8/2017 | Venter et al. |
| 9,745,573 B2 | 8/2017 | Stuelpnagel et al. |
| 9,745,619 B2 | 8/2017 | Rabbani et al. |
| 9,765,387 B2 | 9/2017 | Rabbani et al. |
| 9,771,576 B2 | 9/2017 | Gibson et al. |
| 9,833,761 B2 | 12/2017 | Banyai et al. |
| 9,834,774 B2 | 12/2017 | Carstens |
| 9,839,894 B2 | 12/2017 | Banyai |
| 9,879,283 B2 | 1/2018 | Ravinder et al. |
| 9,889,423 B2 | 2/2018 | Banyai |
| 9,895,673 B2 | 2/2018 | Peck |
| 9,925,510 B2 | 3/2018 | Jacobson et al. |
| 9,932,576 B2 | 4/2018 | Raymond et al. |
| 9,981,239 B2 | 5/2018 | Banyai et al. |
| 10,053,688 B2 | 8/2018 | Cox |
| 10,272,410 B2 | 4/2019 | Banyai |
| 10,583,415 B2 | 3/2020 | Banyai et al. |
| 10,754,994 B2 | 8/2020 | Peck |
| 10,773,232 B2 | 9/2020 | Banyai et al. |
| 2001/0018512 A1 | 8/2001 | Blanchard |
| 2001/0039014 A1 | 11/2001 | Bass et al. |
| 2001/0055761 A1 | 12/2001 | Kanemoto et al. |
| 2002/0012930 A1 | 1/2002 | Rothberg et al. |
| 2002/0025561 A1 | 2/2002 | Hodgson |
| 2002/0076716 A1 | 6/2002 | Sabanayagam et al. |
| 2002/0081582 A1 | 6/2002 | Gao et al. |
| 2002/0094533 A1 | 7/2002 | Hess et al. |
| 2002/0095073 A1 | 7/2002 | Jacobs et al. |

(56) References Cited

U.S. PATENT DOCUMENTS

| | | |
|---|---|---|
| 2002/0119459 A1 | 8/2002 | Griffiths et al. |
| 2002/0132308 A1 | 9/2002 | Liu et al. |
| 2002/0155439 A1 | 10/2002 | Rodriguez et al. |
| 2002/0160536 A1 | 10/2002 | Regnier et al. |
| 2002/0164824 A1 | 11/2002 | Xiao et al. |
| 2003/0008411 A1 | 1/2003 | Van Dam et al. |
| 2003/0022207 A1 | 1/2003 | Balasubramanian et al. |
| 2003/0022317 A1 | 1/2003 | Jack et al. |
| 2003/0044781 A1 | 3/2003 | Korlach et al. |
| 2003/0058629 A1 | 3/2003 | Hirai et al. |
| 2003/0064398 A1 | 4/2003 | Barnes |
| 2003/0068633 A1 | 4/2003 | Belshaw et al. |
| 2003/0082719 A1 | 5/2003 | Schumacher et al. |
| 2003/0100102 A1 | 5/2003 | Rothberg et al. |
| 2003/0108903 A1 | 6/2003 | Wang et al. |
| 2003/0120035 A1 | 6/2003 | Gao et al. |
| 2003/0138782 A1 | 7/2003 | Evans |
| 2003/0143605 A1 | 7/2003 | Lok et al. |
| 2003/0148291 A1 | 8/2003 | Robotti |
| 2003/0148344 A1 | 8/2003 | Rothberg et al. |
| 2003/0171325 A1 | 9/2003 | Gascoyne et al. |
| 2003/0186226 A1 | 10/2003 | Brennan et al. |
| 2003/0228602 A1 | 12/2003 | Parker et al. |
| 2003/0228620 A1 | 12/2003 | Du Breuil Lastrucci |
| 2004/0009498 A1 | 1/2004 | Short |
| 2004/0043509 A1 | 3/2004 | Stahler et al. |
| 2004/0053362 A1 | 3/2004 | De Luca et al. |
| 2004/0086892 A1 | 5/2004 | Crothers et al. |
| 2004/0087008 A1 | 5/2004 | Schembri |
| 2004/0106130 A1 | 6/2004 | Besemer et al. |
| 2004/0106728 A1 | 6/2004 | McGall et al. |
| 2004/0110133 A1 | 6/2004 | Xu et al. |
| 2004/0175710 A1 | 9/2004 | Haushalter |
| 2004/0175734 A1 | 9/2004 | Stahler et al. |
| 2004/0191810 A1 | 9/2004 | Yamamoto |
| 2004/0219663 A1 | 11/2004 | Page et al. |
| 2004/0236027 A1 | 11/2004 | Maeji et al. |
| 2004/0248161 A1 | 12/2004 | Rothberg et al. |
| 2004/0259146 A1 | 12/2004 | Friend et al. |
| 2005/0022895 A1 | 2/2005 | Barth et al. |
| 2005/0049796 A1 | 3/2005 | Webb et al. |
| 2005/0053968 A1 | 3/2005 | Bharadwaj et al. |
| 2005/0079510 A1 | 4/2005 | Berka et al. |
| 2005/0100932 A1 | 5/2005 | Lapidus et al. |
| 2005/0112608 A1 | 5/2005 | Grossman et al. |
| 2005/0112636 A1 | 5/2005 | Hurt et al. |
| 2005/0112679 A1 | 5/2005 | Myerson et al. |
| 2005/0124022 A1 | 6/2005 | Srinivasan et al. |
| 2005/0137805 A1 | 6/2005 | Lewin et al. |
| 2005/0208513 A1 | 9/2005 | Agbo et al. |
| 2005/0227235 A1 | 10/2005 | Carr et al. |
| 2005/0255477 A1 | 11/2005 | Carr et al. |
| 2005/0266045 A1 | 12/2005 | Canham et al. |
| 2005/0277125 A1 | 12/2005 | Benn et al. |
| 2005/0282158 A1 | 12/2005 | Landegren |
| 2006/0003381 A1 | 1/2006 | Gilmore et al. |
| 2006/0003958 A1 | 1/2006 | Melville et al. |
| 2006/0012784 A1 | 1/2006 | Ulmer |
| 2006/0012793 A1 | 1/2006 | Harris |
| 2006/0019084 A1 | 1/2006 | Pearson |
| 2006/0024678 A1 | 2/2006 | Buzby |
| 2006/0024711 A1 | 2/2006 | Lapidus et al. |
| 2006/0024721 A1 | 2/2006 | Pedersen |
| 2006/0076482 A1 | 4/2006 | Hobbs et al. |
| 2006/0078909 A1 | 4/2006 | Srinivasan et al. |
| 2006/0078927 A1 | 4/2006 | Peck et al. |
| 2006/0078937 A1 | 4/2006 | Korlach et al. |
| 2006/0127920 A1 | 6/2006 | Church et al. |
| 2006/0134638 A1 | 6/2006 | Mulligan et al. |
| 2006/0160138 A1 | 7/2006 | Church |
| 2006/0171855 A1 | 8/2006 | Yin et al. |
| 2006/0202330 A1 | 9/2006 | Reinhardt et al. |
| 2006/0203236 A1 | 9/2006 | Ji et al. |
| 2006/0203237 A1 | 9/2006 | Ji et al. |
| 2006/0207923 A1 | 9/2006 | Li |
| 2006/0219637 A1 | 10/2006 | Killeen et al. |
| 2007/0031857 A1 | 2/2007 | Makarov et al. |
| 2007/0031877 A1 | 2/2007 | Stahler et al. |
| 2007/0043516 A1 | 2/2007 | Gustafsson et al. |
| 2007/0054127 A1 | 3/2007 | Hergenrother et al. |
| 2007/0059692 A1 | 3/2007 | Gao et al. |
| 2007/0087349 A1 | 4/2007 | Staehler et al. |
| 2007/0099208 A1 | 5/2007 | Drmanac et al. |
| 2007/0122817 A1 | 5/2007 | Church et al. |
| 2007/0141557 A1 | 6/2007 | Raab et al. |
| 2007/0196854 A1 | 8/2007 | Stahler et al. |
| 2007/0207482 A1 | 9/2007 | Church et al. |
| 2007/0207487 A1 | 9/2007 | Emig et al. |
| 2007/0231800 A1 | 10/2007 | Roberts et al. |
| 2007/0238104 A1 | 10/2007 | Barrett et al. |
| 2007/0238106 A1 | 10/2007 | Barrett et al. |
| 2007/0238108 A1 | 10/2007 | Barrett et al. |
| 2007/0259344 A1 | 11/2007 | Leproust et al. |
| 2007/0259345 A1 | 11/2007 | Sampas |
| 2007/0259346 A1 | 11/2007 | Gordon et al. |
| 2007/0259347 A1 | 11/2007 | Gordon et al. |
| 2007/0269870 A1 | 11/2007 | Church et al. |
| 2008/0085511 A1 | 4/2008 | Peck et al. |
| 2008/0085514 A1 | 4/2008 | Peck et al. |
| 2008/0087545 A1 | 4/2008 | Jensen et al. |
| 2008/0161200 A1 | 7/2008 | Yu et al. |
| 2008/0182296 A1 | 7/2008 | Chanda et al. |
| 2008/0214412 A1 | 9/2008 | Stahler et al. |
| 2008/0227160 A1 | 9/2008 | Kool |
| 2008/0233616 A1 | 9/2008 | Liss |
| 2008/0287320 A1 | 11/2008 | Baynes et al. |
| 2008/0300842 A1 | 12/2008 | Govindarajan et al. |
| 2008/0308884 A1 | 12/2008 | Kalvesten |
| 2008/0311628 A1 | 12/2008 | Shoemaker |
| 2009/0036664 A1 | 2/2009 | Peter |
| 2009/0053704 A1 | 2/2009 | Novoradovskaya et al. |
| 2009/0062129 A1 | 3/2009 | McKernan et al. |
| 2009/0087840 A1 | 4/2009 | Baynes et al. |
| 2009/0088679 A1 | 4/2009 | Wood et al. |
| 2009/0105094 A1 | 4/2009 | Heiner et al. |
| 2009/0170802 A1 | 7/2009 | Stahler et al. |
| 2009/0176280 A1 | 7/2009 | Hutchison, III et al. |
| 2009/0181861 A1 | 7/2009 | Li et al. |
| 2009/0194483 A1 | 8/2009 | Robotti et al. |
| 2009/0230044 A1 | 9/2009 | Bek |
| 2009/0238722 A1 | 9/2009 | Mora-Fillat et al. |
| 2009/0239759 A1 | 9/2009 | Balch |
| 2009/0246788 A1 | 10/2009 | Albert et al. |
| 2009/0263802 A1 | 10/2009 | Drmanac |
| 2009/0285825 A1 | 11/2009 | Kini et al. |
| 2009/0324546 A1 | 12/2009 | Notka et al. |
| 2010/0004143 A1 | 1/2010 | Shibahara |
| 2010/0009872 A1 | 1/2010 | Eid et al. |
| 2010/0047805 A1 | 2/2010 | Wang |
| 2010/0051967 A1 | 3/2010 | Bradley et al. |
| 2010/0069250 A1 | 3/2010 | White, III et al. |
| 2010/0090341 A1 | 4/2010 | Wan et al. |
| 2010/0099103 A1 | 4/2010 | Hsieh et al. |
| 2010/0160463 A1 | 6/2010 | Wang et al. |
| 2010/0167950 A1 | 7/2010 | Juang et al. |
| 2010/0173364 A1 | 7/2010 | Evans, Jr. et al. |
| 2010/0216648 A1 | 8/2010 | Staehler et al. |
| 2010/0256017 A1 | 10/2010 | Larman et al. |
| 2010/0258487 A1 | 10/2010 | Zelechonok et al. |
| 2010/0286290 A1 | 11/2010 | Lohmann et al. |
| 2010/0292102 A1 | 11/2010 | Nouri |
| 2010/0300882 A1 | 12/2010 | Zhang et al. |
| 2011/0009607 A1 | 1/2011 | Komiyama et al. |
| 2011/0082055 A1 | 4/2011 | Fox et al. |
| 2011/0114244 A1 | 5/2011 | Yoo et al. |
| 2011/0114549 A1 | 5/2011 | Yin et al. |
| 2011/0124049 A1 | 5/2011 | Li et al. |
| 2011/0124055 A1 | 5/2011 | Carr et al. |
| 2011/0126929 A1 | 6/2011 | Velasquez-Garcia et al. |
| 2011/0171651 A1 | 7/2011 | Richmond |
| 2011/0172127 A1 | 7/2011 | Jacobson et al. |
| 2011/0201057 A1 | 8/2011 | Carr et al. |
| 2011/0217738 A1 | 9/2011 | Jacobson |
| 2011/0230653 A1 | 9/2011 | Novoradovskaya et al. |

(56) References Cited

U.S. PATENT DOCUMENTS

| | | |
|---|---|---|
| 2011/0254107 A1 | 10/2011 | Bulovic et al. |
| 2011/0287435 A1 | 11/2011 | Grunenwald et al. |
| 2012/0003713 A1 | 1/2012 | Hansen et al. |
| 2012/0021932 A1 | 1/2012 | Mershin et al. |
| 2012/0027786 A1 | 2/2012 | Gupta et al. |
| 2012/0028843 A1 | 2/2012 | Ramu et al. |
| 2012/0032366 A1 | 2/2012 | Ivniski et al. |
| 2012/0046175 A1 | 2/2012 | Rodesch et al. |
| 2012/0050411 A1 | 3/2012 | Mabritto et al. |
| 2012/0094847 A1 | 4/2012 | Warthmann et al. |
| 2012/0128548 A1 | 5/2012 | West et al. |
| 2012/0129704 A1 | 5/2012 | Gunderson et al. |
| 2012/0149602 A1 | 6/2012 | Friend et al. |
| 2012/0164127 A1 | 6/2012 | Short et al. |
| 2012/0164633 A1 | 6/2012 | Laffler |
| 2012/0164691 A1 | 6/2012 | Eshoo et al. |
| 2012/0184724 A1 | 7/2012 | Sierzchala et al. |
| 2012/0220497 A1 | 8/2012 | Jacobson et al. |
| 2012/0231968 A1 | 9/2012 | Bruhn et al. |
| 2012/0238737 A1 | 9/2012 | Dellinger et al. |
| 2012/0258487 A1 | 10/2012 | Chang et al. |
| 2012/0264653 A1 | 10/2012 | Carr et al. |
| 2012/0270750 A1 | 10/2012 | Oleinikov |
| 2012/0270754 A1 | 10/2012 | Blake |
| 2012/0283140 A1 | 11/2012 | Chu |
| 2012/0288476 A1 | 11/2012 | Hartmann et al. |
| 2012/0289691 A1 | 11/2012 | Dellinger et al. |
| 2012/0315670 A1 | 12/2012 | Jacobson et al. |
| 2012/0322681 A1 | 12/2012 | Kung et al. |
| 2013/0005585 A1 | 1/2013 | Anderson et al. |
| 2013/0005612 A1 | 1/2013 | Carr et al. |
| 2013/0017642 A1 | 1/2013 | Milgrew et al. |
| 2013/0017977 A1 | 1/2013 | Oleinikov |
| 2013/0017978 A1 | 1/2013 | Kavanagh et al. |
| 2013/0035261 A1 | 2/2013 | Sierzchala et al. |
| 2013/0040836 A1 | 2/2013 | Himmler et al. |
| 2013/0045483 A1 | 2/2013 | Treusch et al. |
| 2013/0053252 A1 | 2/2013 | Xie et al. |
| 2013/0059296 A1 | 3/2013 | Jacobson et al. |
| 2013/0059761 A1 | 3/2013 | Jacobson et al. |
| 2013/0065017 A1 | 3/2013 | Sieber |
| 2013/0109595 A1 | 5/2013 | Routenberg |
| 2013/0109596 A1 | 5/2013 | Peterson et al. |
| 2013/0123129 A1 | 5/2013 | Zeiner et al. |
| 2013/0130321 A1 | 5/2013 | Staehler et al. |
| 2013/0137161 A1 | 5/2013 | Zhang et al. |
| 2013/0137173 A1 | 5/2013 | Zhang et al. |
| 2013/0137174 A1 | 5/2013 | Zhang et al. |
| 2013/0137861 A1 | 5/2013 | Leproust et al. |
| 2013/0164308 A1 | 6/2013 | Foletti et al. |
| 2013/0196864 A1 | 8/2013 | Govindarajan et al. |
| 2013/0225421 A1 | 8/2013 | Li et al. |
| 2013/0244884 A1 | 9/2013 | Jacobson et al. |
| 2013/0252849 A1 | 9/2013 | Hudson et al. |
| 2013/0261027 A1 | 10/2013 | Li et al. |
| 2013/0281308 A1 | 10/2013 | Kung et al. |
| 2013/0296192 A1 | 11/2013 | Jacobson et al. |
| 2013/0296194 A1 | 11/2013 | Jacobson et al. |
| 2013/0298265 A1 | 11/2013 | Cunnac et al. |
| 2013/0309725 A1 | 11/2013 | Jacobson et al. |
| 2013/0323725 A1 | 12/2013 | Peter et al. |
| 2013/0330778 A1 | 12/2013 | Zeiner et al. |
| 2014/0011226 A1 | 1/2014 | Bernick et al. |
| 2014/0018441 A1 | 1/2014 | Fracchia et al. |
| 2014/0031240 A1 | 1/2014 | Behlke et al. |
| 2014/0038240 A1 | 2/2014 | Temme et al. |
| 2014/0106394 A1 | 4/2014 | Ko et al. |
| 2014/0141982 A1 | 5/2014 | Jacobson et al. |
| 2014/0170665 A1 | 6/2014 | Hiddessen et al. |
| 2014/0178992 A1 | 6/2014 | Nakashima et al. |
| 2014/0274729 A1 | 9/2014 | Kurn et al. |
| 2014/0274741 A1 | 9/2014 | Hunter et al. |
| 2014/0303000 A1 | 10/2014 | Armour et al. |
| 2014/0309119 A1 | 10/2014 | Jacobson et al. |
| 2014/0309142 A1 | 10/2014 | Tian |
| 2015/0010953 A1 | 1/2015 | Lindstrom et al. |
| 2015/0012723 A1 | 1/2015 | Park et al. |
| 2015/0031089 A1 | 1/2015 | Lindstrom |
| 2015/0038373 A1 | 2/2015 | Banyai et al. |
| 2015/0056609 A1 | 2/2015 | Daum et al. |
| 2015/0057625 A1 | 2/2015 | Coulthard |
| 2015/0065357 A1 | 3/2015 | Fox |
| 2015/0065393 A1 | 3/2015 | Jacobson |
| 2015/0099870 A1 | 4/2015 | Bennett et al. |
| 2015/0120265 A1 | 4/2015 | Amirav-Drory |
| 2015/0159152 A1 | 6/2015 | Allen et al. |
| 2015/0183853 A1 | 7/2015 | Sharma et al. |
| 2015/0191719 A1 | 7/2015 | Hudson et al. |
| 2015/0196917 A1 | 7/2015 | Kay et al. |
| 2015/0203839 A1 | 7/2015 | Jacobson et al. |
| 2015/0211047 A1 | 7/2015 | Borns |
| 2015/0225782 A1 | 8/2015 | Walder et al. |
| 2015/0240232 A1 | 8/2015 | Zamore et al. |
| 2015/0240280 A1 | 8/2015 | Gibson et al. |
| 2015/0261664 A1 | 9/2015 | Goldman et al. |
| 2015/0269313 A1 | 9/2015 | Church |
| 2015/0293102 A1 | 10/2015 | Shim |
| 2015/0307875 A1 | 10/2015 | Happe et al. |
| 2015/0321191 A1 | 11/2015 | Kendall et al. |
| 2015/0322504 A1 | 11/2015 | Lao et al. |
| 2015/0344927 A1 | 12/2015 | Sampson et al. |
| 2015/0353921 A9 | 12/2015 | Tian |
| 2015/0353994 A1 | 12/2015 | Myers et al. |
| 2015/0361420 A1 | 12/2015 | Hudson et al. |
| 2015/0361422 A1 | 12/2015 | Sampson et al. |
| 2015/0361423 A1 | 12/2015 | Sampson et al. |
| 2015/0368687 A1 | 12/2015 | Saaem et al. |
| 2015/0376602 A1 | 12/2015 | Jacobson et al. |
| 2016/0001247 A1 | 1/2016 | Oleinikov |
| 2016/0002621 A1 | 1/2016 | Nelson et al. |
| 2016/0002622 A1 | 1/2016 | Nelson et al. |
| 2016/0010045 A1 | 1/2016 | Cohen et al. |
| 2016/0017394 A1 | 1/2016 | Liang et al. |
| 2016/0017425 A1 | 1/2016 | Ruvolo et al. |
| 2016/0019341 A1 | 1/2016 | Harris et al. |
| 2016/0024138 A1 | 1/2016 | Gebeyehu et al. |
| 2016/0024576 A1 | 1/2016 | Chee et al. |
| 2016/0026753 A1 | 1/2016 | Krishnaswami et al. |
| 2016/0026758 A1 | 1/2016 | Jabara et al. |
| 2016/0032396 A1 | 2/2016 | Diehn et al. |
| 2016/0046973 A1 | 2/2016 | Efcavitch et al. |
| 2016/0046974 A1 | 2/2016 | Efcavitch et al. |
| 2016/0082472 A1 | 3/2016 | Perego et al. |
| 2016/0089651 A1 | 3/2016 | Banyai |
| 2016/0090592 A1 | 3/2016 | Banyai et al. |
| 2016/0096160 A1 | 4/2016 | Banyai et al. |
| 2016/0097051 A1 | 4/2016 | Jacobson et al. |
| 2016/0102322 A1 | 4/2016 | Ravinder et al. |
| 2016/0108466 A1 | 4/2016 | Nazarenko et al. |
| 2016/0122755 A1 | 5/2016 | Hall et al. |
| 2016/0122800 A1 | 5/2016 | Bernick et al. |
| 2016/0152972 A1 | 6/2016 | Stapleton et al. |
| 2016/0168611 A1 | 6/2016 | Efcavitch et al. |
| 2016/0184788 A1 | 6/2016 | Hall et al. |
| 2016/0200759 A1 | 7/2016 | Srivastava et al. |
| 2016/0215283 A1 | 7/2016 | Braman et al. |
| 2016/0229884 A1 | 8/2016 | Indermuhle et al. |
| 2016/0230175 A1 | 8/2016 | Carstens |
| 2016/0230221 A1 | 8/2016 | Bergmann et al. |
| 2016/0251651 A1 | 9/2016 | Banyai |
| 2016/0256846 A1 | 9/2016 | Smith et al. |
| 2016/0264958 A1 | 9/2016 | Toro et al. |
| 2016/0289758 A1 | 10/2016 | Akeson et al. |
| 2016/0289839 A1 | 10/2016 | Harumoto et al. |
| 2016/0303535 A1 | 10/2016 | Banyai et al. |
| 2016/0304862 A1 | 10/2016 | Igawa et al. |
| 2016/0304946 A1 | 10/2016 | Betts et al. |
| 2016/0310426 A1 | 10/2016 | Wu |
| 2016/0310927 A1 | 10/2016 | Banyai et al. |
| 2016/0318016 A1 | 11/2016 | Hou et al. |
| 2016/0333340 A1 | 11/2016 | Wu |
| 2016/0339409 A1 | 11/2016 | Banyai et al. |
| 2016/0340672 A1 | 11/2016 | Banyai et al. |
| 2016/0348098 A1 | 12/2016 | Stuelpnagel et al. |

(56) References Cited

U.S. PATENT DOCUMENTS

| | | |
|---|---|---|
| 2016/0354752 A1 | 12/2016 | Banyai et al. |
| 2016/0355880 A1 | 12/2016 | Gormley et al. |
| 2017/0017436 A1 | 1/2017 | Church |
| 2017/0066844 A1 | 3/2017 | Glanville |
| 2017/0067099 A1 | 3/2017 | Zheng et al. |
| 2017/0073731 A1 | 3/2017 | Zheng et al. |
| 2017/0081660 A1 | 3/2017 | Cox |
| 2017/0081716 A1 | 3/2017 | Peck |
| 2017/0088887 A1 | 3/2017 | Makarov et al. |
| 2017/0095785 A1 | 4/2017 | Banyai et al. |
| 2017/0096706 A1 | 4/2017 | Behlke et al. |
| 2017/0114404 A1 | 4/2017 | Behlke et al. |
| 2017/0141793 A1 | 5/2017 | Strauss et al. |
| 2017/0147748 A1 | 5/2017 | Staehler et al. |
| 2017/0151546 A1 | 6/2017 | Peck et al. |
| 2017/0159044 A1 | 6/2017 | Toro et al. |
| 2017/0175110 A1 | 6/2017 | Jacobson et al. |
| 2017/0218537 A1 | 8/2017 | Olivares |
| 2017/0233764 A1 | 8/2017 | Young et al. |
| 2017/0249345 A1 | 8/2017 | Malik et al. |
| 2017/0253644 A1 | 9/2017 | Steyaert et al. |
| 2017/0320061 A1 | 11/2017 | Venter et al. |
| 2017/0327819 A1 | 11/2017 | Banyai et al. |
| 2017/0355984 A1 | 12/2017 | Evans et al. |
| 2017/0357752 A1 | 12/2017 | Diggans |
| 2017/0362589 A1 | 12/2017 | Banyai |
| 2018/0029001 A1 | 2/2018 | Banyai |
| 2018/0051278 A1 | 2/2018 | Cox et al. |
| 2018/0051280 A1 | 2/2018 | Gibson et al. |
| 2018/0068060 A1 | 3/2018 | Ceze et al. |
| 2018/0101487 A1 | 4/2018 | Peck |
| 2018/0104664 A1 | 4/2018 | Fernandez |
| 2018/0126355 A1 | 5/2018 | Peck et al. |
| 2018/0142289 A1 | 5/2018 | Zeitoun |
| 2018/0171509 A1 | 6/2018 | Cox |
| 2018/0236425 A1 | 8/2018 | Banyai et al. |
| 2018/0253563 A1 | 9/2018 | Peck et al. |
| 2018/0264428 A1 | 9/2018 | Banyai et al. |
| 2018/0273936 A1 | 9/2018 | Cox |
| 2018/0282721 A1 | 10/2018 | Cox et al. |
| 2018/0312834 A1 | 11/2018 | Cox et al. |
| 2018/0326388 A1 | 11/2018 | Banyai et al. |
| 2018/0355351 A1 | 12/2018 | Nugent et al. |
| 2019/0060345 A1 | 2/2019 | Harrison et al. |
| 2019/0118154 A1 | 4/2019 | Marsh et al. |
| 2019/0135926 A1 | 5/2019 | Glanville |
| 2019/0240636 A1 | 8/2019 | Peck et al. |
| 2019/0352635 A1 | 11/2019 | Toro et al. |
| 2019/0366293 A1 | 12/2019 | Banyai et al. |
| 2019/0370164 A1 * | 12/2019 | Goldman ............... B82Y 10/00 |
| 2020/0017907 A1 | 1/2020 | Zeitoun et al. |
| 2020/0102611 A1 | 4/2020 | Zeitoun et al. |
| 2020/0156037 A1 | 5/2020 | Banyai et al. |
| 2020/0181667 A1 | 6/2020 | Wu et al. |
| 2020/0222875 A1 | 7/2020 | Peck et al. |
| 2020/0283760 A1 | 9/2020 | Nugent et al. |
| 2020/0299322 A1 | 9/2020 | Indermuhle et al. |
| 2020/0299684 A1 | 9/2020 | Toro et al. |
| 2020/0308575 A1 | 10/2020 | Sato |

FOREIGN PATENT DOCUMENTS

| | | | |
|---|---|---|---|
| CA | 2792676 A1 | 9/2011 | |
| CN | 1771336 A | 5/2006 | |
| CN | 102159726 A | 8/2011 | |
| CN | 103907117 A | 7/2014 | |
| CN | 104520864 A | 4/2015 | |
| CN | 104562213 A * | 4/2015 | |
| CN | 104734848 A | 6/2015 | |
| DE | 10260805 A1 | 7/2004 | |
| EP | 0090789 A1 | 10/1983 | |
| EP | 0126621 B1 | 8/1990 | |
| EP | 0753057 A1 | 1/1997 | |
| EP | 1314783 A1 | 5/2003 | |
| EP | 1363125 A2 | 11/2003 | |
| EP | 1546387 A2 | 6/2005 | |
| EP | 1153127 B1 | 7/2006 | |
| EP | 1728860 A1 | 12/2006 | |
| EP | 1072010 B1 | 4/2010 | |
| EP | 2175021 A2 | 4/2010 | |
| EP | 2330216 A1 | 6/2011 | |
| EP | 1343802 B1 | 5/2012 | |
| EP | 2504449 A1 | 10/2012 | |
| EP | 2751729 A1 | 7/2014 | |
| EP | 2872629 A1 | 5/2015 | |
| EP | 2928500 A1 | 10/2015 | |
| EP | 2971034 A1 | 1/2016 | |
| EP | 3030682 A2 | 6/2016 | |
| EP | 3044228 A4 | 4/2017 | |
| EP | 2994509 B1 | 6/2017 | |
| EP | 3204518 A1 | 8/2017 | |
| JP | 2002536977 A | 11/2002 | |
| JP | 2002538790 A | 11/2002 | |
| JP | 2006503586 A | 2/2006 | |
| JP | 2008523786 A | 7/2008 | |
| JP | 2008218579 A * | 9/2008 | |
| JP | 2009294195 A | 12/2009 | |
| JP | 2016527313 A | 9/2016 | |
| WO | WO-9015070 A1 | 12/1990 | |
| WO | WO-9210092 A1 | 6/1992 | |
| WO | WO-9210588 A1 | 6/1992 | |
| WO | WO-9309668 A1 | 5/1993 | |
| WO | WO-9525116 A1 | 9/1995 | |
| WO | WO-9526397 A1 | 10/1995 | |
| WO | WO-9615861 A1 | 5/1996 | |
| WO | WO-9710365 A1 | 3/1997 | |
| WO | WO-9822541 A2 | 5/1998 | |
| WO | WO-9841531 A2 | 9/1998 | |
| WO | WO-9942813 A1 | 8/1999 | |
| WO | WO-0013017 A2 | 3/2000 | |
| WO | WO-0018957 A1 | 4/2000 | |
| WO | WO-0042559 A1 | 7/2000 | |
| WO | WO-0042560 A2 | 7/2000 | |
| WO | WO-0042561 A2 | 7/2000 | |
| WO | WO-0049142 A1 | 8/2000 | |
| WO | WO-0053617 A1 | 9/2000 | |
| WO | WO-0156216 A2 | 8/2001 | |
| WO | WO-0210443 A1 | 2/2002 | |
| WO | WO-0156216 A3 | 3/2002 | |
| WO | WO-0220537 A2 | 3/2002 | |
| WO | WO-0224597 A2 | 3/2002 | |
| WO | WO-0227638 A1 | 4/2002 | |
| WO | WO-0233669 A1 | 4/2002 | |
| WO | WO-02072791 A2 | 9/2002 | |
| WO | WO-03040410 A1 | 5/2003 | |
| WO | WO-03046223 A1 | 6/2003 | |
| WO | WO-03054232 A2 | 7/2003 | |
| WO | WO-03064026 A1 | 8/2003 | |
| WO | WO-03064027 A2 | 8/2003 | |
| WO | WO-03064699 A2 | 8/2003 | |
| WO | WO-03065038 A2 | 8/2003 | |
| WO | WO-03066212 A2 | 8/2003 | |
| WO | WO-03089605 A2 | 10/2003 | |
| WO | WO-03093504 A1 * | 11/2003 | ........... C12Q 1/6855 |
| WO | WO-03100012 A2 | 12/2003 | |
| WO | WO-2004024886 A2 | 3/2004 | |
| WO | WO-2004029220 A2 | 4/2004 | |
| WO | WO-2004029586 A1 | 4/2004 | |
| WO | WO-2004031351 A2 | 4/2004 | |
| WO | WO-2004031399 A2 | 4/2004 | |
| WO | WO-2004059556 A2 | 7/2004 | |
| WO | WO-2005014850 A2 | 2/2005 | |
| WO | WO-2005051970 A2 | 6/2005 | |
| WO | WO-2005059096 A2 | 6/2005 | |
| WO | WO-2005059097 A2 | 6/2005 | |
| WO | WO-2006023144 | 3/2006 | |
| WO | WO-2006044956 A1 | 4/2006 | |
| WO | WO-2006076679 A1 | 7/2006 | |
| WO | WO-2006116476 A1 | 11/2006 | |
| WO | WO-2007120627 A2 | 10/2007 | |
| WO | WO-2007137242 A2 | 11/2007 | |
| WO | WO-2008006078 A2 | 1/2008 | |
| WO | WO-2008027558 A2 | 3/2008 | |
| WO | WO-2008045380 | 4/2008 | |

(56) References Cited

FOREIGN PATENT DOCUMENTS

| | | |
|---|---|---|
| WO | WO-2008054543 A2 | 5/2008 |
| WO | WO-2008063134 A1 | 5/2008 |
| WO | WO-2008063135 A1 | 5/2008 |
| WO | WO-2008109176 A2 | 9/2008 |
| WO | WO-2010025310 A2 | 3/2010 |
| WO | WO-2010025566 A1 | 3/2010 |
| WO | WO-2010027512 A2 | 3/2010 |
| WO | WO-2010089412 A1 | 8/2010 |
| WO | WO-2010141433 A2 | 12/2010 |
| WO | WO-2010141433 A3 | 4/2011 |
| WO | WO-2011053957 A2 | 5/2011 |
| WO | WO-2011056872 A2 | 5/2011 |
| WO | WO-2011066185 A1 | 6/2011 |
| WO | WO-2011066186 A1 | 6/2011 |
| WO | WO-2011085075 A2 | 7/2011 |
| WO | WO-2011103468 A2 | 8/2011 |
| WO | WO-2011109031 A1 | 9/2011 |
| WO | WO-2011143556 A1 | 11/2011 |
| WO | WO-2011150168 A1 | 12/2011 |
| WO | WO-2011161413 A2 | 12/2011 |
| WO | WO-2012013913 A1 | 2/2012 |
| WO | WO-2012061832 A1 | 5/2012 |
| WO | WO-2012078312 A2 | 6/2012 |
| WO | WO-2012149171 A1 | 11/2012 |
| WO | WO-2012154201 A1 | 11/2012 |
| WO | WO-2013030827 A1 | 3/2013 |
| WO | WO-2013032850 A2 | 3/2013 |
| WO | WO-2013036668 A1 | 3/2013 |
| WO | WO-2013101896 A1 | 7/2013 |
| WO | WO-2013154770 A1 | 10/2013 |
| WO | WO-2013177220 A1 | 11/2013 |
| WO | WO-2014004393 A1 | 1/2014 |
| WO | WO-2014008447 A1 | 1/2014 |
| WO | WO-2014035693 A2 | 3/2014 |
| WO | WO-2014088693 A1 | 6/2014 |
| WO | WO-2014089160 A1 | 6/2014 |
| WO | WO-2014093330 A1 | 6/2014 |
| WO | WO-2014093694 A1 | 6/2014 |
| WO | WO-2014151117 A1 | 9/2014 |
| WO | WO-2014151696 A1 | 9/2014 |
| WO | WO-2014160004 A1 | 10/2014 |
| WO | WO-2014160059 A1 | 10/2014 |
| WO | WO-2014206304 A1 | 12/2014 |
| WO | WO-2015017527 A2 | 2/2015 |
| WO | WO-2015021080 A2 | 2/2015 |
| WO | WO-2015021280 A1 | 2/2015 |
| WO | WO-2015031689 A1 | 3/2015 |
| WO | WO-2015040075 A1 | 3/2015 |
| WO | WO-2015054292 A1 | 4/2015 |
| WO | WO-2015066174 A1 | 5/2015 |
| WO | WO-2015081114 A2 | 6/2015 |
| WO | WO-2015081142 A1 | 6/2015 |
| WO | WO-2015090879 A1 | 6/2015 |
| WO | WO-2015095404 A2 | 6/2015 |
| WO | WO-2015120403 A1 | 8/2015 |
| WO | WO-2015136072 A1 | 9/2015 |
| WO | WO-2015160004 A1 | 10/2015 |
| WO | WO-2015175832 A1 | 11/2015 |
| WO | WO-2016007604 A1 | 1/2016 |
| WO | WO-2016011080 A2 | 1/2016 |
| WO | WO-2016022557 A1 | 2/2016 |
| WO | WO-2016053883 A1 | 4/2016 |
| WO | WO-2016055956 A1 | 4/2016 |
| WO | WO-2016065056 A1 | 4/2016 |
| WO | WO-2016126882 A1 | 8/2016 |
| WO | WO-2016126987 A1 | 8/2016 |
| WO | WO-2016130868 A2 | 8/2016 |
| WO | WO-2016161244 A2 | 10/2016 |
| WO | WO-2016162127 A1 | 10/2016 |
| WO | WO-2016164779 A1 | 10/2016 |
| WO | WO-2016172377 A1 | 10/2016 |
| WO | WO-2016173719 A1 | 11/2016 |
| WO | WO-2016183100 A1 | 11/2016 |
| WO | WO-2017017423 A1 | 2/2017 |
| WO | WO-2017049231 A1 | 3/2017 |
| WO | WO-2017053450 A1 | 3/2017 |
| WO | WO-2017059399 A1 | 4/2017 |
| WO | WO-2017095958 A1 | 6/2017 |
| WO | WO-2017100441 A1 | 6/2017 |
| WO | WO-2017118761 A1 | 7/2017 |
| WO | WO-2017158103 A1 | 9/2017 |
| WO | WO-2017214574 A1 | 12/2017 |
| WO | WO-2018026920 A1 | 2/2018 |
| WO | WO-2018038772 A1 | 3/2018 |
| WO | WO-2018057526 A2 | 3/2018 |
| WO | WO-2018094263 A1 | 5/2018 |
| WO | WO-2018112426 A1 | 6/2018 |
| WO | WO-2018156792 A1 | 8/2018 |
| WO | WO-2018170164 A1 | 9/2018 |
| WO | WO-2018170169 A1 | 9/2018 |
| WO | WO-2018200380 A1 | 11/2018 |
| WO | WO-2018231872 A1 | 12/2018 |
| WO | WO-2019051501 A1 | 3/2019 |
| WO | WO-2019079769 A1 | 4/2019 |
| WO | WO-2019084500 A1 | 5/2019 |
| WO | WO-2019136175 A1 | 7/2019 |
| WO | WO-2019222706 A1 | 11/2019 |
| WO | WO-2020139871 A1 | 7/2020 |
| WO | WO-2020176362 A1 | 9/2020 |
| WO | WO-2020176678 A1 | 9/2020 |
| WO | WO-2020176680 A1 | 9/2020 |

OTHER PUBLICATIONS

Acevedo-Rocha et al. Directed evolution of stereoselective enzymes based on genetic selection as opposed to screening systems. J. Biotechnol. 191:3-10 (2014).

Adessi, et al. Solid phase DNA amplification: characterisation of primer attachment and amplification mechanisms. Nucleic Acids Res. 28(20):E87, 2000.

Alexeyev, Mikhail F. et al., Gene synthesis, bacterial expression and purification of the Rickettsia prowazekii ATP/ADP translocase, Biochimica et Biophysics Acta, 1419:299-306, 1999.

Al-Housseiny et al., Control of interfacial instabilities using flow geometry Nature Physics, 8:747-750, 2012.

Amblard, Francois et al., A magnetic manipulator for studying local rheology and micromechanical properties of biological systems, Rev. Sci. Instrum., 67(3):18-827, 1996.

Andoni and Indyk, Near-Optimal Hashing Algorithms for Approximate Nearest Neighbor in High Dimensions, Communications of the ACM, 51(1):117-122, 2008.

Arand et al. Structure of Rhodococcus erythropolis limonene-1,2-epoxide hydrolase reveals a novel active site. EMBO J. 22:2583-2592 (2003).

Arkles, et al. The Role of Polarity in the Structure of Silanes Employed in Surface Modification. Silanes and Other Coupling Agents. 5:51-64, 2009.

Arkles, Hydrophobicity, Hydrophilicity Reprinted with permission from the Oct. 2006 issue of Paint & Coatings Industry magazine, Retrieved on Mar. 19, 2016, 10 pages.

Assembly manual for the POSaM: The ISB Piezoelelctric Oligonucleotide Synthesizer and Microarrayer, The Institute for Systems Biology, May 28, 2004 (50 pages).

Assi et al. Massive-parallel adhesion and reactivity-measurements using simple and inexpensive magnetic tweezers. J. Appl. Phys. 92(9):5584-5586 (2002).

ATDBio, Nucleic Acid Structure, Nucleic Acids Book, 9 pages, published on Jan. 22, 2005. from: http://www.atdbio.com/content/5/Nucleic-acid-structure.

ATDBio, Solid-Phase Oligonucleotide Synthesis, Nucleic Acids Book, 20 pages, Published on Jul. 31, 2011. from: http://www.atdbio.com/content/17/Solid-phase-oligonucleotide-synthesis.

Au et al. Gene synthesis by a LCR-based approach: high level production of Leptin-L54 using synthetic gene in *Escherichia coli*. Biochemical and Biophysical Research Communications 248:200-203 (1998).

Baedeker, Mathias et al., Overexpression of a designed 2.2kb gene of eukaryotic phenylalanine ammonialyase in *Escherichia coli*. FEBS Letters, 457:57- 60, 1999.

(56) References Cited

OTHER PUBLICATIONS

Barbee, et al. Magnetic Assembly of High-Density DNA Arrays for Genomic Analyses. Anal Chem. 80(6):2149-2154, 2008.
Barton et al., A desk electrohydrodynamic jet printing system. Mechatronics, 20:611-616, 2010.
Beaucage, et al. Advances in the synthesis of oligonucleotides by the phosphoramidite approach. Tetrahedron. 48:2223-2311, 1992.
Beaucage, et al. Deoxynucleoside phosphoramidites—A new class of key intermediates for deoxypolynucleotide synthesis. Tetrahedron Lett. 22(20):1859-1862, 1981.
Beaucage, Serge L. et al., The Chemical synthesis of DNA/RNA Chapter 2 in: Encyclopedia of Cell Biology, 1:36-53, 2016.
Beaulieu, Martin et al., PCR candidate region mismatch scanning adaptation to quantitative, high-throughput genotyping, Nucleic Acids Research, 29(5):1114-1124, 2001.
Beigelman, et al. Base-modified phosphoramidite analogs of pyrimidine ribonucleosides for RNA structure-activity studies. Methods Enzymol. 317:39-65, 2000.
Bethge et al., Reverse synthesis and 3'-modification of RNA. Jan. 1, 2011, pp. 64-64, XP055353420. Retrieved from the Internet: URL:http://www.is3na.org/assets/events/Category%202-Medicinal %20Chemistry%20of%20oligonucleotides%20%2864-108%29.pdf.
Binkowski et al., Correcting errors in synthetic DNA through consensus shuffling. Nucleic Acids Research, 33(6):e55, 8 pages, 2005.
Biswas, Indranil et al., Identification and characterization of a thermostable MutS homolog from Thennus aquaticus, The Journal of Biological Chemistry, 271(9):5040-5048, 1996.
Biswas, Indranil et al., Interaction of MutS protein with the major and minor grooves of a heteroduplex DNA, The Journal of Biological Chemistry, 272(20):13355-13364, 1997.
Bjornson, Keith P. et al., Differential and simultaneous adenosine Di- and Triphosphate binding by MutS, The Journal of Biological Chemistry, 278(20):18557-18562, 2003.
Blanchard, et al. High-Density Oligonucleotide Arrays. Biosens. & Bioelectronics. 1996; 11:687-690.
Blanchard, in: Genetic Engineering, Principles and Methods, vol. 20, Ed. J. Sedlow, New York: Plenum Press, p. 111-124, 1979.
Blawat et al., Forward error correction for DNA data storage. Procedia Computer Science, 80:1011-1022, 2016.
Bonini and Mondino, Adoptive T-cell therapy for cancer: The era of engineered T cells. European Journal of Immunology, 45:2457-2469, 2015.
Bornholt et al., A DNA-Based Archival Storage System, in International Conference on Architectural Support for Programming Languages and Operating Systems (ASPLOS), Apr. 2-6, 2016, Atlanta, GA, 2016, 637-649.
Borovkov et al., High-quality gene assembly directly from unpurified mixtures of microassay-synthesized oligonucleotides. Nucleic Acid Research, 38(19):e180, 10 pages, 2010.
Brunet, Aims and methods of biosteganography. Journal of Biotechnology, 226:56-64, 2016.
Buermans et al., Next Generation sequencing technology: Advances and applications, Biochimica et Biophysica Acta (BBA)—Molecular Basis of Disease, 1842:1931-1941, 2014.
Butler, et al. In situ synthesis of oligonucleotide arrays by using surface tension. J Am Chem Soc. 123(37):8887-94, 2001.
Calvert, Lithographically patterned self-assembled films. In: Organic Thin Films and Surfaces: Directions for the Nineties, vol. 20, p. 109, ed. By Abraham Ulman, San Diego: Academic Press, 1995.
Cardelli, Two-Domain DNA Strand Displacement, Electron. Proc. Theor. Comput. Sci., 26:47-61, 2010.
Carlson, Time for New DNA Synthesis and Sequencing Cost Curves, 2014. [Online]. Available: http://www.synthesis.cc/synthesis/2014/02/time_for_new_cost_curves_2014. 10 pages.
Carr, et al. Protein-mediated error correction for de novo DNA synthesis. Nucleic Acids Res. 32(20):e162, 9 pages, 2004.
Carter and Friedman, DNA synthesis and Biosecurity: Lessons learned and options for the future. J. Craig Venter Institute, La Jolla, CA, 28 pages, Oct. 2015.
Caruthers, Chemical synthesis of deoxyoligonucleotides by the phosphoramidite method. In Methods in Enzymology, Chapter 15, 154:287-313, 1987.
Caruthers. Gene synthesis machines: DNA chemistry and its uses. Science 230(4723):281-285 (1985).
Caruthers, The Chemical Synthesis of DNA/RNA: Our Gift to Science. J. Biol. Chem., 288(2):1420-1427, 2013.
Casmiro, Danilo R. et al., PCR-based gene synthesis and protein NMR spectroscopy, Structure, 5(11):1407-1412, 1997.
CeGaT. Tech Note available at https://www.cegat.de/web/wp-content/uploads/2018/06/Twist-Exome-Tech-Note.pdf (4 pgs.) (2018).
Cello, et al. Chemical synthesis of poliovirus cDNA: generation of infectious virus in the absence of natural template. Science. 297(5583):1016-8, 2000.
Chalmers, et al. Scaling up the ligase chain reaction-based approach to gene synthesis. Biotechniques. 30(2):249-52, 2001.
Chan, et al. Natural and engineered nicking endonucleases—from cleavage mechanism to engineering of strand-specificity. Nucleic Acids Res. 39(1):1-18, 2011.
Chen, et al. Chemical modification of gene silencing oligonucleotides for drug discovery and development. Drug Discov Today. 10(8):587-93 2005.
Chen et al., Programmable chemical controllers made from DNA, Nat. Nanotechnol., 8(10):755-762, 2013.
Cheng, et al. High throughput parallel synthesis of oligonucleotides with 1536 channel synthesizer. Nucleic Acids Res. 30(18):e93, 2002.
Chilamakuri et al. Performance comparison of four exome capture systems for deep sequencing. BMC Genomics 15(1):449 (2014).
Cho, et al. Capillary passive valve in microfluidic systems. NSTI-Nanotech. 2004; 1:263-266.
Chrisey et al., Fabrication of patterned DNA surfaces Nucleic Acids Research, 24(15):3040-3047 (1996).
Chung et al., One-step preparation of competent*Escherichia coli*:Transformation and storage of bacterial cells in the same solution. Proc Natl Acad Sci U S A. Apr. 1989;86(7):2172-2175.
Church et al., Next-generation digital information storage in DNA. Science, 337:6102, 1628-1629, 2012.
Cleary et al. Production of complex nucleic acid libraries using highly parallel in situ oligonucleotide synthesis. Nat Methods 1(3):241-248 (2004).
Cohen et al., Human population: The next half century. Science, 302:1172-1175, 2003.
Crick. On protein synthesis. Symp Soc Exp Biol12:138-163,1958.
Cruse et al. Atlas of Immunology, Third Edition. Boca Raton:CRC Press (pp. 282-283) (2010).
Cutler, David J. et al., High-throughput variation detection and genotyping using microarrays, Genome Research, vol. 11, 1913-19 (2001).
Dahl, et al. Circle-to-circle amplification for precise and sensitive DNA analysis. Proc Natl Acad Sci U S A. Mar. 30, 2004;101(13):4548-53. Epub Mar. 15, 2004.
De Mesmaeker, et al. Backbone modifications in oligonucleotides and peptide nucleic acid systems. Curr Opin Struct Biol. Jun. 1995;5(3):343-55.
De Silva et al. New Trends of Digital Data Storage in DNA. BioMed Res Int. 2016:8072463 (2016).
Deamer, David W. et al., Characterization of nucleic acids by nanopore analysis, Acc. Cham. Res., vol. 35, No. 10, 817-825 (2002).
Deaven, The Human Genome Project: Recombinant clones for mapping and sequencing DNA. Los Alamos Science, 20:218-249, 1992.
Deng et al., Targeted bisulfite sequencing reveals changes in DNA methylation associated with nuclear reprogramming Nature Biotechnology, 27:352-360 (2009).
Dietrich, Rudiger.et al., Gene assembly based on blunt-ended double-stranded DNA-modules, Biotechnology Techniques, vol. 12, No. 1, 49-54 (Jan. 1998).
Dillon et al. Exome sequencing has higher diagnostic yield compared to simulated disease-specific panels in children with suspected monogenic disorders. Eur J Hum Genet 26(5):644-651 (2018).

(56) References Cited

OTHER PUBLICATIONS

Dormitzer et al., Synthetic generation of influenza vaccine viruses for rapid response to pandemics. Sci Translational Medicine, 5(185):185ra68, 14 pages, 2013.
Doudna et al. Genome editing. The new frontier of genome engineering with CRISPR-Cas9. Science 346(6213):1258096-1-1258096-9, 2014.
Dower et al., High efficiency transformation of *E.coli* by high voltage electroporation. Nucleic Acids Res. 16(13):6127-45 (1988).
Dressman, et al. Transforming single DNA molecules into fluorescent magnetic particles for detection and enumeration of genetic variations. Proc Natl Acad Sci U S A. Jul. 22, 2003;100(15):8817-22. Epub Jul. 11, 2003.
Drmanac, et al. Human genome sequencing using unchained base reads on self-assembling DNA nanoarrays. Science. Jan. 1, 2010;327(5961):78-81. doi: 10.1126/science.1181498. Epub Nov. 5, 2009.
Droege and Hill, The Genome Sequencer FLXTM System-Longer reads, more applications, straight forward bioinformatics and more complete data sets Journal of Biotechnology, 136:3-10, 2008.
Duffy, et al. Rapid Prototyping of Microfluidic Systems in Poly(dimethylsiloxane). Anal Chem. Dec. 1, 1998;70(23):4974-84. doi: 10.1021/ac980656z.
Duggan, et al. Expression profiling using cDNA microarrays. Nat Genet. Jan. 1999;21(1 Suppl):10-4.
Dvorsky. Living Bacteria Can Now Store Data. GIZMODO internet publication. Retrieved from https://gizmodo.com/living-bacteria-can-now-store-data-1781773517 (4 pgs) (Jun. 10, 2016).
Eadie, et al. Guanine modification during chemical DNA synthesis. Nucleic Acids Res. Oct. 26, 1987;15(20):8333-49.
Eisen, Jonathan A., A phylogenomic study of the MutS family of proteins, Nucleic Acids Research, vol. 26, No. 18, 4291-4300 (1998).
Ellis, et al. DNA assembly for synthetic biology: from parts to pathways and beyond. Integr Biol (Camb). Feb. 2011;3(2):109-18. doi: 10.1039/c0ib00070a. Epub Jan. 19, 2011.
El-Sagheer, et al. Biocompatible artificial DNA linker that is read through by DNA polymerases and is functional in *Escherichia coli*. Proc Natl Acad Sci U S A. Jul. 12, 2011;108(28):11338-43. doi: 10.1073/pnas.1101519108. Epub Jun. 27, 2011.
Elsik et al., The Genome sequence of taurine cattle: A window of ruminant biology and evolution. Science, 324:522-528, 2009.
Elsner et al., 172 nm excimer VUV-triggered photodegradation and micropatterning of aminosilane films, Thin Solid Films, 517:6772-6776 (2009).
Engler, et al. A one pot, one step, precision cloning method with high throughput capability. PLoS One. 2008;3(11):e3647. doi: 10.1371/journal.pone.0003647. Epub Nov. 5, 2008.
Engler, et al. Golden gate shuffling: a one-pot DNA shuffling method based on type IIs restriction enzymes. PLoS One. 2009;4(5):e5553. doi: 10.1371/journal.pone.0005553. Epub May 14, 2009.
Erlich and Zielinski, DNA fountain enables a robust and efficient storage architecture. Science, 355(6328):950-054, 2017.
European Patent Application No. 12827479.2 Extended European Search Report dated May 18, 2015.
European Patent Application No. 12827479.2 Partial European Search Report dated Jan. 29, 2015.
European Patent Application No. 14834665.3 Communication dated Jan. 16, 2018.
European Patent Application No. 14834665.3 extended European Search Report dated Apr. 28, 2017.
European Patent Application No. 14834665.3 Further Examination Report dated Nov. 28, 2018.
European Patent Application No. 14834665.3 Office Action dated May 2, 2018.
European Patent Application No. 16847497.1 Extended European Search Report dated Jan. 9, 2019.
European Patent Application No. 16871446.7 European Search Report dated Apr. 10, 2019.
Evans et al., DNA Repair Enzymes. Current Protocols in Molecular Biology 84:III:3.9:3.9.1-3.9.12 http://www.ncbi.nlm.nih.gov/pubmed/18972391 (Published online Oct. 1, 2008 Abstract only provided).
Fahy, et al. Self-sustained sequence replication (3SR): an isothermal transcription-based amplification system alternative to PCR. PCR Methods Appl. Aug. 1991;1(1):25-33.
Fedoryak, Olesya D. et al., Brominated hydroxyquinoline as a photolabile protecting group with sensitivity to multiphoton excitation, Org. Lett., vol. 4, No. 2 , 3419-3422 (2002).
Ferretti et al., Total synthesis of a gene for bovine rhodopsin. PNAS, 83:599-603 (1986).
Finger et al., The wonders of Flap Endonucleases: Structure, function, mechanism and regulation. Subcell Biochem., 62:301-326, 2012.
Fodor et al., Light-directed, spatially addressable parallel chemical synthesis. Science. 251(4995):767-773 (1991).
Fogg et al., Structural basis for uracil recognition by archaeal family B DNA polymerases. Nature Structural Biology, 9(12):922-927, 2002.
Foldesi, et al. The synthesis of deuterionucleosides. Nucleosides Nucleotides Nucleic Acids. Oct.-Dec. 2000;19(10-12):1615-56.
Frandsen, et al. Efficient four fragment cloning for the construction of vectors for targeted gene replacement in filamentous fungi. BMC Molecular Biology 2008, 9:70.
Frandsen. Experimental setup. Dec. 7, 2010, 3 pages. http://www.rasmusfrandsen.dk/experimental_setup.htm.
Frandsen. The USER Friendly technology. USER cloning. Oct. 7, 2010, 2 pages. http://www.rasmusfrandsen.dk/user_cloning.htm.
Fullwood et al., Next-generation DNA sequencing of paired-end tags [PET] for transcriptome and genome analysis Genome Research, 19:521-532, 2009.
Galneder. et al., Microelectrophoresis of a bilayer-coated silica bead in an optical trap: application to enzymology. Biophysical Journal, vol. 80, No. 5, 2298-2309 (May 2001).
Gao, et al. A flexible light-directed DNA chip synthesis gated by deprotection using solution photogenerated acids. Nucleic Acids Res. Nov. 15, 2001;29(22):4744-50.
Gao et al. A method for the generation of combinatorial antibody libraries using pIX phage display. PNAS 99(20):12612-12616 (2002).
Gao, et al. Thermodynamically balanced inside-out (TBIO) PCR-based gene synthesis: a novel method of primer design for high-fidelity assembly of longer gene sequences. Nucleic Acids Res. Nov. 15, 2003;31(22):e143.
Garaj, et al. Graphene as a subnanometre trans-electrode membrane. Nature. Sep. 9, 2010;467(7312):190-3. doi: 10.1038/nature09379.
Garbow, Norbert et al., Optical tweezing electroghoresis of isolated, highly charged colloidal spheres, Colloids and Surfaces A: Physiochem. Eng. Aspects, vol. 195, 227-241 (2001).
GeneArt Seamless Cloning and Assembly Kits. Life Technologies Synthetic Biology. 8 pages, available online Jun. 15, 2012.
Genomics 101. An Introduction to the Genomic Workflow. 2016 edition, 64 pages. Available at: http://www.frontlinegenomics.com/magazine/6757/genomics-101/.
Geu-Flores, et al. USER fusion: a rapid and efficient method for simultaneous fusion and cloning of multiple PCR products. Nucleic Acids Res. 2007;35(7):e55. Epub Mar. 27, 2007.
Gibson Assembly. Product Listing. Application Overview. 2 pages, available online Dec. 16, 2014.
Gibson, et al. Complete chemical synthesis, assembly, and cloning of a Mycoplasma genitalium genome. Science. Feb. 29, 2008;319(5867):1215-20. doi: 10.1126/science.1151721. Epub Jan. 24, 2008.
Gibson et al. Creation of a Bacterial Cell Controlled by a Chemically Synthesized Genome. Science 329(5989):52-56 (2010).
Goldfeder et al. Medical implications of technical accuracy in genome sequencing. Genome Med 8(1):24 (2016).
Goldman et al., Towards practical, high-capacity, low-maintenance information storage in synthesized DNA, Nature, 494(7435):77-80, 2013.
Gosse, Charlie et al. Magnetic tweezers: micromanipulation and force measurement at the molecular level, Biophysical Journal, vol. 8, 3314-3329 (Jun. 2002).

(56) References Cited

OTHER PUBLICATIONS

Grass, et al., Robust chemical preservation of digital information on DNA in silica with error-correcting codes, Angew. Chemie—Int. Ed., 54(8):2552-2555, 2015.
Greagg et al., A read-ahead function in archaeal DNA polymerases detects promutagenic template-strand uracil. Proc. Nat. Acad. Sci. USA, 96:9045-9050, 1999.
Grovenor. Microelectronic materials. Graduate Student Series in Materials Science and Engineering. Bristol, England: Adam Hilger, 1989; p. 113-123.
Gu et al., Depletion of abundant sequences by hybridization (DASH): using Cas9 to remove unwanted high-abundance species in sequencing libraries and molecular counting applications. Genome Biology, 17:41, 13 pages, 2016.
Haber, Charbel et al., Magnetic tweezers for DNA micromanipulation, Rev. Sci. Instrum., vol. 71, No. 12, 4561-4570 (Dec. 2000).
Han et al. Linking T-cell receptor sequence to functional phenotype at the single-cell level. Nat Biotechnol 32(7):684-692 (2014).
Hanahan and Cold Spring Harbor Laboratory, Studies on transformation of *Escherichia coli* with plasmids J. Mol. Biol. 166:557-580 (1983).
Hanahan et al., Plasmid transformation of *Escherichia coli* and other bacteria. Methods Enzymol, vol. 204, p. 63-113 (1991).
Harada, et al. Unexpected substrate specificity of T4 DNA ligase revealed by in vitro selection. Nucleic Acids Res. May 25, 1993;21(10):2287-91.
Heckers Karl H. et al., Error analysis of chemically synthesized polynucleotides, BioTechniques, vol. 24, No. 2, 256-260 (1998).
Herzer et al.: Fabrication of patterned silane based self-assembled monolayers by photolithography and surface reactions on silicon-oxide substrates Chem. Commun., 46:5634-5652 (2010).
Hoover et al., DNAWorks: an automated method for designing oligonucleotides for PCR-based gene synthesis, Nucleic Acids Research, vol. 30, No. 10, e43, 7 pages (2002).
Hosu, Basarab G. et al., Magnetic tweezers for intracellular applications•, Rev. Sci. Instrum., vol. 74, No. 9, 4158-4163 (Sep. 2003).
Huang, Hayden et al., Three-dimensional cellular deformation analysis with a two-photon magnetic manipulator workstation, Biophysical Journal, vol. 82, No. 4, 2211•2223 (Apr. 2002).
Hughes et al. Expression profiling using microarrays fabricated by an ink-jet oligonucleotide synthesizer Nat Biotech 4:342-347 (2001).
Hughes et al. Principles of early drug discovery. Br J Pharmacol 162(2):1239-1249, 2011.
Hutchison, et al. Cell-free cloning using phi29 DNA polymerase. Proc Natl Acad Sci U S A. Nov. 29, 2005;102(48):17332-6. Epub Nov. 14, 2005.
IMGUR: The magic of the internet. Uploaded May 10, 2012, 2 pages, retrieved from: https://imgur.com/mEWuW.
In-Fusion Cloning: Accuracy, Not Background. Cloning & Competent Cells, ClonTech Laboratories, 3 pages, available online Jul. 6, 2014.
International Application No. PCT/US2017/026232 International Preliminary Report on Patentability dated Feb. 26, 2019.
International Application No. PCT/US2017/045105 International Preliminary Report on Patentability dated Feb. 5, 2019.
International Application No. PCT/US2017/052305 International Preliminary Report on Patentability dated Apr. 30, 2019.
International Application No. PCT/US2017/062391 International Preliminary Report on Patentability dated May 21, 2019.
International Application No. PCT/US2018/050511 International Search Report and Written Opinion dated Jan. 11, 2019.
International Application No. PCT/US2018/057857 International Search Report and Written Opinion dated Mar. 18, 2019.
International Application No. PCT/US2019/012218 International Search Report and Written Opinion dated Mar. 21, 2019.
Jackson, Brian A. et al., Recognition of DNA base mismatches by a rhodium intercalator, J. Am. Chem. Soc., vol. 19, 12986•12987 (1997).
Jacobs et al. DNA glycosylases: In DNA repair and beyond. Chromosoma 121:1-20 (2012)—http://www.ncbi.nlm.nih.gov/pmc/articles/PMC3260424/.
Jacobus et al. Optimal cloning of PCR fragments by homologous recombination in *Escherichia soli*. PLoS One 10(3):e0119221 (2015).
Jager et al. Simultaneous Humoral and Cellular: Immune Response against Cancer—Testis Antigen NY-ES0-1: Definition of Human Histocompatibility LeukocyteAntigen (HLA)-A2—binding Peptide Epitopes. J. Exp. Med. 187(2):265-270 (1998).
Jinek et al., A Programmable dual-RNA-guided DNA endonuclease in adaptive bacterial immunity. Science, 337:816-821, 2012.
Karagiannis and El-Osta, RNA interference and potential therapeutic applications of short interfering RNAs Cancer Gene Therapy, 12:787-795, 2005.
Ke, Song-Hua et al., Influence of neighboring base pairs on the stability of single base bulges and base pairs in a DNA fragment, Biochemistry, Vo. 34, 4593-4600 (1995).
Kelley, Shana, et al. Single-base mismatch detection based on charge transduction through DNA, Nucleic Acids Research, vol. 27, No. 24, 4830-4837 (1999).
Kim et al., High-resolution patterns of quantum dots formed by electrohydrodynamic jet printing for light-emitting diodes. Nano Letters, 15:969-973, 2015.
Kim, Yang-Gyun et al., Chimeric restriction endonuclease, Proc. Natl. Acad. Sci. USA, vol. 91, 883-887 (Feb. 1994).
Kim, Yang-Gyun, The interaction between Z-ONA and the Zab domain of double-stranded RNA adenosine deaminase characterized using fusion nucleases, The Journal of Biological Chemistry, vol. 274, No. 27, 19081-19086 (1999).
Kim, Yan-Gyun et al., Site specific cleavage of DNA-RNA hybrids by zinc finger/Fok I cleavage domain fusions Gene, vol. 203, 43-49 (1997).
Kinde, et al. Detection and quantification of rare mutations with massively parallel sequencing. Proc Natl Acad Sci U S A. Jun. 7, 2011;108(23):9530-5. Epub May 17, 2011.
Kodumal, et al. Total synthesis of long DNA sequences: synthesis of a contiguous 32-kb polyketide synthase gene cluster. Proc Natl Acad Sci U S A. Nov. 2, 2004;101(44):15573-8. Epub Oct. 20, 2004.
Koike-Yusa et al., Genome-wide recessive genetic screening in mammalian cells with a lentiviral CRISPR-guide RNA library. Nature Biotechnology, 32:267-273, 2014 (with three pages of supplemental Online Methods).
Kong et al., Parallel gene synthesis in a microfluidic device. Nucleic Acids Res., 35(8):e61 (2007).
Kong. Microfluidic Gene Synthesis. MIT Thesis. Submitted to the program in Media Arts and Sciences, School of Architecture and Planning, in partial fulfillment of the requirements for the degree of Doctor of Philosophy in Media Arts and Sciences at the Massachusetts Institute of Technology. 143 pages Jun. 2008.
Kopp, Martin U. et al., Chemical amplification: continuous-flow PCR on a chip, Science, vol. 280, 1046-1048 (May 15, 1998).
Kosuri and Church, Large-scale de novo DNA synthesis: technologies and applications, Nature Methods, 11:499-507, 2014. Available at: http://www.nature.com/nmeth/journal/v11/n5/full/nmeth.2918.html.
Kosuri, et al. A scalable gene synthesis by selective amplification of DNA pools from high-fidelity microchips. Nature Biotechnology. 2010; 28:1295-1299.
Krayden, Inc., A Guide to Silane Solutions. Silane coupling agents. 7 pages. Published on May 31, 2005 at: http://krayden.com/pdf/xia_silane_chemistry.pdf.
Lagally, et al. Single-Molecule DNA Amplification and Analysis in an Integrated Microfluidic Device. Analytical Chemistry. 2001;73(3):565-570.
Lahue, R.S. et al., DNA mismatch correction in a defined system, Science, vol. 425; No. 4914, 160-164 (Jul. 14, 1989).
Lambrinakos, A. et al., Reactivity of potassium permanganate and tetraethylammonium chloride with mismatched bases and a simple mutation detection protocol,Nucleic Acids Research, vol. 27, No. 8, 1866-1874 (1999).
Landegren, et al. A ligase-mediated gene detection technique. Science. Aug. 26, 1988;241(4869):1077-80.

(56) References Cited

OTHER PUBLICATIONS

Lang, Matthew J. et al., An automated two-dimensional optical force clamp for single molecule studies, Biophysical Journal, vol. 83, 491•501 (Jul. 2002).
Lashkari, et al. An automated multiplex oligonucleotide synthesizer: development of high-throughput, low-cost DNA synthesis. Proc Natl Acad Sci U S A. Aug. 15, 1995;92(17):7912-5.
Lausted et al., POSaM: a fast, flexible, open-source, inkjet oligonucleotide synthesizer and microarrayer, Genome Biology, 5:R58, 17 pages, 2004. available at https://www.ncbi.nlm.nih.gov/pmc/articles/PMC507883/.
Leamon, et al. A massively parallel PicoTiterPlate based platform for discrete picoliter-scale polymerase chain reactions. Electrophoresis. Nov. 2003;24(21):3769-77.
Lee: Covalent End-Immobilization of Oligonucleotides onto Solid Surfaces; Thesis, Massachusetts Institute of Technology, Aug. 2001 (315 pages).
Lee, C.S. et al., Microelectromagnets for the control of magnetic nanoparticles, Appl. Phys. Lett., vol. 79, No. 20, 3308-3310 (Nov. 12, 2001).
Lee, et al. A microfluidic oligonucleotide synthesizer. Nucleic Acids Research 2010 vol. 38(8):2514-2521. DOI: 10.1093/nar/gkq092.
Leproust, et al. Agilent's Microarray Platform: How High-Fidelity DNA Synthesis Maximizes the Dynamic Range of Gene Expression Measurements. 2008; 1-12. http://www.miltenyibiotec.com/~/media/Files/Navigation/Genomic%20Services/Agilent_DNA_Microarray_Platform.ashx.
Leproust, et al. Synthesis of high-quality libraries of long (150mer) oligonucleotides by a novel depurination controlled process. Nucleic Acids Research. 2010; 38(8):2522-2540.
Lesnikowski, et al. Nucleic acids and nucleosides containing carboranes. J. Organometallic Chem. 1999; 581:156-169.
Leumann. DNA analogues: from supramolecular principles to biological properties. Bioorg Med Chem. Apr. 2002;10(4):841-54.
Levene, et al. Zero-mode waveguides for single-molecule analysis at high concentrations. Science. Jan. 31, 2003;299(5607):682-6.
Lewontin and Harti, Population genetics in forensic DNA typing. Science, 254:1745-1750, 1991.
Li et al., Beating bias in the directed evolution of proteins: Combining high-fidelity on-chip solid-phase gene synthesis with efficient gene assembly for combinatorial library construction. First published Nov. 24, 2017, 2 pages. retrieved from: https://doi.org/10.1002/cbic.201700540.
Li et al. Beating Bias in the Directed Evolution of Proteins: Combining High-Fidelity on-Chip Solid-Phase Gene Synthesis with Efficient Gene Assembly for Combinatorial Library Construction. ChemBioChem 19:221-228 (2018).
Light source unit for printable patterning VUV-Aligner / USHIO Inc., Link here: https://www.ushio.co.jp/en/products/1005.html, published Apr. 25, 2016, printed from the internet on Aug. 2, 2016, 3 pages.
Limbachiya et al., Natural data storage: A review on sending information from now to then via Nature. ACM Journal on Emerging Technologies in Computing Systems, V(N):Article A, May 19, 2015, 17 pages.
Link Technologies. Product Guide 2010. Nov. 27, 2009, 136 pages. XP055353191. Retrieved from the Internet: URL:http://www.linktech.co.uk/documents/517/517.pdf.
Lipshutz, Robert J. et al., High density synthetic oligonucleotide arrays, Nature Genetics Supplement, vol. 21, 20-24 (Jan. 1999).
Lishanski, Alia et al., Mutation detection by mismatch binding protein, MutS, in amplified DNA: application to the cystic fibrosis gene, Proc. Natl. Acad. Sci. USA, vol. 91, 2674-2678 (Mar. 1994).
Liu et al., Comparison of Next-Generation Sequencing Systems. Journal of Biomedicine and Biotechnology, 11 pages, 2012.
Liu, et al. Enhanced Signals and Fast Nucleic Acid Hybridization by Microfluidic Chaotic Mixing. Angew. Chem. Int. Ed. 2006; 45:3618-3623.
Liu et al., Rational design of CXCR4 specific antibodies with elongated CDRs. JACS, 136:10557-10560, 2014.
Lizardi, et al. Mutation detection and single-molecule counting using isothermal rolling-circle amplification. Nat Genet. Jul. 1998;19(3):225-32.
Li, Lin et al., Functional domains in Fok I restriction endonuclease, Proc. Natl. Acad. Sci. USA, 89:4275-4279, 1992.
Lu, A.-Lien et al., Methyl-directed repair of DNA base-pair mismatches in vitro, Proc. Natl. Acad. Sci. USA, 80:4639-4643, 1983.
Lund, et al. A validated system for ligation-free uracilexcision based assembly of expression vectors for mammalian cell engineering. DTU Systems of Biology. 2011. 1 page. http://www.lepublicsystemepco.com/files/modules/gestion_rubriques/REF-B036-Lund_Anne%20Mathilde.pdf.
Ma, et al. DNA synthesis, assembly and application in synthetic biology. Current Opinion in Chemical Biology. 16:260-267, 2012.
Ma et al., Versatile surface functionalization of cyclic olefin copolymer (COC) with sputtered SiO2 thin film for potential BioMEMS applications. Journal of Materials Chemistry, 11 pages, 2009.
Mahato et al., Modulation of gene expression by antisense and antigene oligodeoxynucleotides and small interfering RNA Expert Opin. Drug Delivery, 2(1):3-28, 2005.
Margulies, et al. Genome sequencing in open microfabricated high-density picolitre reactors. Nature. 437(7057):376-80, 2005.
Matteucci, et al. Synthesis of deoxyoligonucleotides on a polymer support. J. Am. Chem. Soc. 103(11):3185-3191, 1981.
Matzas et al., Next generation gene synthesis by targeted retrieval of bead-immobilized, sequence verified DNA clones from a high throughput pyrosequencing device. Nat. Biotechnol., 28(12):1291-1294, 2010.
Mazor et al.: Isolation of Full-Length IgG Antibodies from Combinatorial Libraries Expressed in *Escherichia coli*; Antony S. Dimitrov (ed.), Therapeutic Antibodies: Methods and Protocols, vol. 525, Chapter 11, pp. 217-239 (2009).
McBride & Caruthers, An investigation of several deoxynucleoside phosphoramidites useful for synthesizing deoxyoligonucleotides. Tetrahedron Lett. 24: 245-248, 1983.
McGall, et al. Light-directed synthesis of high-density oligonucleotide arrays using semiconductor photoresists. Proc Natl Acad Sci U S A. 93(24):13555-60, 1996.
McGall, et al. The Efficiency of Light-Directed Synthesis of DNA Arrays on Glass Substrates. J. Am. Chem. Soc. 119(22):5081-5090, 1997.
Mei et al., Cell-free protein synthesis in microfluidic array devices Biotechnol. Prog., 23(6):1305-1311, 2007.
Mendel-Hartvig. Padlock probes and rolling circle amplification. New possibilities for sensitive gene detection. Comprehensive Summaries of Uppsala Dissertations from the Faculty of Medicine 1175. Uppsala University. 2002, 39 pages. http://www.diva-portal.org/smash/get/diva2:161926/FULLTEXT01.pdf.
Meyers and Friedland, Knowledge-based simulation of genetic regulation in bacteriophage lambda. Nucl. Acids Research, 12(1):1-16, 1984.
Meynert et al. Quantifying single nucleotide variant detection sensitivity in exome sequencing. BMC Bioinformatics 14:195 (2013).
Meynert et al. Variant detection sensitivity and biases in whole genome and exome sequencing. BMC Bioinformatics 15:247 (2014).
Milo and Phillips, Numbers here reflect the number of protein coding genes and excludes tRNA and non-coding RNA. Cell Biology by the Numbers, p. 286, 2015.
Mitra, et al. In situ localized amplification and contact replication of many individual DNA molecules. Nucleic Acids Res. 27(24):e34, 1999.
Morin et al., Profiling the HeLa S3 transcriptome using randomly primed cDNA and massively parallel short-read sequencing. Biotechniques, 45:81-94, 2008.
Morris and Stauss, Optimizing T-cell receptor gene therapy for hematologic malignancies. Blood, 127(26):3305-3311, 2016.
Muller, Caroline et al. Protection and labelling of thymidine by a fluorescent photolabile group, Helvetica Chimica Acta, vol. 84, 3735-3741 (2001).
Mulligan. Commercial Gene Synthesis Technology PowerPoint presentation. BlueHeron® Biotechnology. Apr. 5, 2006 (48 pgs).

(56) References Cited

OTHER PUBLICATIONS

Nakatani, Kazuhiko et al., Recognition of a single guanine bulge by 2-Acylamino-1,8-naphthyridine, J. Am. Chem. Soc., vol. 122, 2172-2177 (2000).
Eroshenko et al.: Gene Assembly from Chip-Synthesized Oligonucleotides; Current Protocols in Chemical biology 4: 1-17 (2012).
Jo et al.: Engineering therapeutic antibodies targeting G-protein-coupled receptors; Experimental & Molecular Medicine; 48; 9 pages (2016).
Douthwaite et al.: Affinity maturation of a novel antagonistic human monoclonal antibody with a long VH CDR3 targeting the Class A GPCR formyl-peptide receptor 1; mAbs, vol. 7, Iss. 1, pp. 152-166 (Jan. 1, 2015).
Neiman M.S,. Negentropy principle in information processing systems. Radiotekhnika, 1966, N°11, p. 2-9.
Neiman M.S., on the bases of the theory of information retrieval. Radiotekhnika, 1967, N° 5, p. 2-10.
Neiman M.S., On the molecular memory systems and the directed mutations. Radiotekhnika, 1965, No. 6, pp. 1-8.
Neiman M.S., On the relationships between the reliability, performance and degree of microminiaturization at the molecular-atomic level. Radiotekhnika, 1965, No. 1, pp. 1-9.
Neiman M.S., Some fundamental issues of microminiaturization. Radiotekhnika, 1964, No. 1, pp. 3-12.
Nishikura, A short primer on RNAi: RNA-directed RNA polymerase acts as a key catalyst Cell, 107:415-418, 2001.
Nour-Eldin, et al. USER Cloning and USER Fusion: The Ideal Cloning Techniques for Small and Big Laboratories. Plant Secondary Metabolism Engineering. Methods in Molecular Biology vol. 643, 2010, pp. 185-200.
Ochman, et al. Genetic applications of an inverse polymerase chain reaction. Genetics. Nov. 1988;120(3):621-3.
Organick et al., Random access in large-scale DNA data storage. Nature Biotechnology, Advance Online Publication, 8 pages, 2018.
Organick et al., Scaling up DNA data storage and random access retrieval, bioRxiv, preprint first posted online Mar. 7, 2017, 14 pages.
Pan, et al. An approach for global scanning of single nucleotide variations. Proc Natl Acad Sci U S A. Jul. 9, 2002;99(14):9346-51.
Pankiewicz. Fluorinated nucleosides. Carbohydr Res. Jul. 10, 2000;327(1-2):87-105.
PCT/IL2012/000326 International Preliminary Report on Patentability dated Dec. 5, 2013.
PCT/IL2012/000326 International Search Report dated Jan. 29, 2013.
PCT/US14/049834 International Preliminary Report on Patentability dated Feb. 18, 2016.
PCT/US2014/049834 International Search Report and Written Opinion dated Mar. 19, 2015.
PCT/US2014/049834, Invitation to Pay Additional Fees and, where applicable, protest fee, dated Jan. 5, 2015.
PCT/US2015/043605 International Preliminary Report on Patentability dated Feb. 16, 2017.
PCT/US2015/043605 International Search Report and Written Opinion dated Jan. 6, 2016.
PCT/US2015/043605 Invitation to Pay Additional Fees dated Oct. 28, 2015.
PCT/US2016/016459 International Preliminary Report on Patentability dated Aug. 17, 2017.
PCT/US2016/016459 International Search Report and Written Opinion dated Apr. 13, 2016.
PCT/US2016/016636 International Preliminary Report on Patentability dated Aug. 17, 2017.
PCT/US2016/016636 International Search Report and Written Opinion dated May 2, 2016.
PCT/US2016/028699 International Preliminary Report on Patentability dated Nov. 2, 2017.
PCT/US2016/028699 International Search Report and Written Opinion dated Jul. 29, 2016.
PCT/US2016/031674 International Preliminary Report on Patentability dated Nov. 23, 2017.
PCT/US2016/031674 International Search Report and Written Opinion dated Aug. 11, 2016.
PCT/US2016/052336 International Preliminary Report on Patentability dated Mar. 29, 2018.
PCT/US2016/052336 International Search Report and Written Opinion dated Dec. 7, 2016.
PCT/US2016/052916 International Preliminary Report on Patentability dated Apr. 5, 2018.
PCT/US2016/052916 International Search Report and Written Opinion dated Dec. 30, 2016.
PCT/US2016/064270 International Preliminary Report on Patentability dated Jun. 14, 2018.
PCT/US2016/064270 International Search Report and Written Opinion dated Apr. 28, 2017.
PCT/US2017/026232 International Search Report and Written Opinion dated Aug. 28, 2017.
PCT/US2017/036868 International Search Report and Written Opinion dated Aug. 11, 2017.
PCT/US2017/045105 International Search Report and Written Opinion dated Oct. 20, 2017.
PCT/US2017/052305 International Search Report and Written Opinion dated Feb. 2, 2018.
PCT/US2017/062391 International Search Report and Written Opinion dated Mar. 28, 2018.
PCT/US2017/066847 International Search Report and Written Opinion dated May 4, 2018.
PCT/US2018/022487 International Search Report and Written Opinion dated Aug. 1, 2018.
PCT/US2018/022493 International Search Report and Written Opinion dated Aug. 1, 2018.
PCT/US2018/037152 International Search Report and Written Opinion dated Aug. 28, 2018.
PCT/US2018/037161 International Search Report and Written Opinion dated Oct. 22, 2018.
PCT/US2018/037161 Invitation to Pay Additional Fees dated Aug. 27, 2018.
PCT/US2018/056783 International Search Report and Written Opinion of the International Searching Authority dated Dec. 20, 2018.
PCT/US2018/19268 International Search Report and Written Opinion dated Jun. 26, 2018.
PCT/US2018/19268 Invitation to Pay Additional Fees and, where applicable, protest fee dated May 2, 2018.
PCT/US2018/22487 Invitation to Pay Additional Fees and, where applicable, protest fee dated May 31, 2018.
PCT/US2018/22493 Invitation to Pay Additional Fees and, where applicable, protest fee dated May 31, 2018.
Pease, et al. Light-generated oligonucleotide arrays for rapid DNA sequence analysis. Proc Natl Acad Sci U S A. May 24, 1994;91(11):5022-6.
Peisajovich, et al. BBF RFC 28: A method for combinatorial multi-part assembly based on the type-lis restriction enzyme aarl. Sep. 16, 2009, 7 pages.
Pellois, et al. Individually addressable parallel peptide synthesis on microchips, Nature Biotechnology, vol. 20 , 922-926 (Sep. 2002).
Petersen, et al. LNA: a versatile tool for therapeutics and genomics. Trends Biotechnol. Feb. 2003;21(2):74-81.
Pierce, et al. Linear-after-the-exponential polymerase chain reaction and allied technologies. Real-time detection strategies for rapid, reliable diagnosis from single cells. Methods Mol Med. 2007;132:65-85.
Pirrung. How to make a DNA chip. Angew. Chem. Int. Ed., 41:1276-1289, 2002.
Plesa et al., Multiplexed gene synthesis in emulsions for exploring protein functional landscapes. Science, 10.1126/science.aao5167, 10 pages, 2018.
Pon. Solid-phase supports for oligonucleotide synthesis. Methods Mol Biol. 1993;20:465-96.
Poster. Reimagine Genome Scale Research. 2016, 1 page. Available at http://www2.twistbioscience.com/Oligo_Pools_CRISPR_poster.

(56) References Cited

OTHER PUBLICATIONS

Powers et al. Optimal strategies for the chemical and enzymatic synthesis of bihelical deoxyribonucleic acids. J Am Chem Soc., 97(4):875-884, 1975.
Pray. Discovery of DNA Structure and Function: Watson and Crick, Nature Education, 2008, 6 pages. available at: http://www.nature.com/scitable/topicpage/discovery-of-dna-structure-and-function-watson-397.
Prodromou, et al. Recursive PCR: a novel technique for total gene synthesis. Protein Eng. Dec. 1992;5(8):827-9.
Puigbo. Optimizer: a web server for optimizing the codon usage of DNA sequences. Nucleic Acid Research, 35(14):126-131, 2007.
Qian and Winfree, Scaling up digital circuit computation with DNA strand displacement cascades. Science, 332(6034):196-1201, 2011.
Qian, et al., Neural network computation with DNA strand displacement cascades, Nature, 475(7356):368-372, 2011.
Quan, et al. Parallel on-chip gene synthesis and application to optimization of protein expression. Nature Biotechnology. 2011; 29:449-452.
Rafalski and Morgante, Corn and humans: recombination and linkage disequilibrium in two genomes of similar size. Trends in Genetics, 20(2):103-111, 2004.
Raje and Murma, A Review of electrohydrodynamic-inkjet printing technology. International Journal of Emerging Technology and Advanced Engineering, 4(5):174-183, 2014.
Rastegari, et al., XNOR-Net: ImageNet Classification Using Binary Convolutional Neural Networks, in ECCV 2016, Part IV, LNCS 9908, p. 525-542, 2016.
Reimagine SequenceSpace, Reimagine Research, Twist Bioscience, Product Brochure, Published Apr. 6, 2016 online at: www2.twistbioscience.com/TB_Product_Brochure_04.2016, 8 pages.
RF Electric discharge type excimer lamp. Products Catalog. Excimer lamp light source flat excimer, 16 pages dated Jan. 2016. From: http://www.hamamatsu.com/jp/en/product/category/1001/3026/index.html.
Richmond, et al. Amplification and assembly of chip-eluted DNA (AACED): a method for high-throughput gene synthesis. Nucleic Acids Res. Sep. 24, 2004;32(17):5011-8. Print 2004.
Roche. Restriction Enzymes from Roche Applied Science—A Tradition of Premium Quality and Scientific Support. FAQS and Ordering Guide. Roche Applied Science. Accessed Jan. 12, 2015, 37 pages.
Rogozin et al., Origin and evolution of spliceosomal introns. Biology Direct, 7:11, 2012.
Ruminy, et al., Long-range identification of hepatocyte nuclear factor-3 (FoxA) high and low-affinity binding Sites with a chimeric nuclease, J. Mol. Bioi., vol. 310, 523-535 (2001).
Saaem et al., In situ synthesis of DNA microarray on functionalized cyclic olefin copolymer substrate ACS Applied Materials & Interfaces, 2(2):491-497, 2010.
Saboulard, et al. High-throughput site-directed mutagenesis using oligonucleotides synthesized on DNA chips. Biotechniques. Sep. 2005;39(3):363-8.
Sacconi, L. et al., Three-dimensional magneto-optic trap for microobject manipulation, Optics Letters, vol. 26, No. 17, 1359-1361 (Sep. 1, 2001).
Saiki et al. Analysis of enzymatically amplified beta-globin and HLA-DQ alpha DNA with allele-specific oligonucleotide probes. Nature 324:163-166 (1986).
Sandhu, et al. Dual asymmetric PCR: one-step construction of synthetic genes. Biotechniques. Jan. 1992;12(1):14-6.
Sargolzaei et al., Extent of linkage disequilibrium in Holstein cattle in North America. J.Dairy Science, 91:2106-2117, 2007.
Schaller, et al. Studies on Polynucleotides. XXV.1 The Stepwise Synthesis of Specific Deoxyribopolynucleotides (5). Further Studies on the Synthesis of Internucleotide Bond by the Carbodiimide Method. The Synthesis of Suitably Protected Dinucleotides as Intermediates in the Synthesis of Higher Oligonucleotides. J. Am. Chem. Soc. 1963; 85(23):3828-3835.
Schmalzing et al. Microchip electrophoresis: a method for high-speed SNP detection. Nucleic Acids Res 28(9):E43 (2000).
Schmitt et al., New strategies in engineering T-cell receptor gene-modified T cells to more effectively target malignancies. Clinical Cancer Research, 21(23):5191-5197, 2015.
Seelig, et al., Enzyme-Free Nucleic Acid Logic Circuits, Science 314(5805):1585-1588, 2006.
Sharan et al. Recombineering: a homologous recombination-based method of genetic engineering. Nat Profile 4(2):1-37 (originally pp. 206-223) (2009).
Sharpe and Mount, Genetically modified T cells in cancer therapy: opportunities and challenges. Disease Models and Mechanisms, 8:337-350, 2015.
Simonyan and Zisserman, Very Deep Convolutional Networks for Large-Scale Image Recognition, Published as a conference paper at Int. Conf. Learn. Represent., pp. 1-14, 2015.
Singh-Gasson, Sangeet et al., Maskless fabrication of light-directed oligonucleotide microarrays using a digital micromirror array, Nature Biotechnology, vol. 17, 974-978 (Oct. 1999).
Skerra. Phosphorothioate primers improve the amplification of DNA sequences by DNA polymerases with proofreading activity. Nucleic Acids Res. Jul. 25, 1992; 20(14):3551-4.
Smith, et al. Generating a synthetic genome by whole genome assembly: phiX174 bacteriophage from synthetic oligonucleotides. Proc Natl Acad Sci U S A. Dec. 23, 2003;100(26):15440-5. Epub Dec. 2, 2003.
Smith, et al. Generation of cohesive ends on PCR products by UDG-mediated excision of dU, and application for cloning into restriction digest-linearized vectors. PCR Methods Appl. May 1993;2(4):328-32.
Smith, Jane et al., Mutation detection with MutH, MutL, and MutS mismatch repair proteins, Proc. Natl. Acad. Sci. USA, vol. 93, 4374-4379 (Apr. 1996).
Smith Jane et al., Removal of Polymerase-Produced mutant sequences from PCR products, Proc. Natl. Acad. Sci. USA, vol. 94, 6847-6850 (Jun. 1997).
Smith, Steven B. et al., Direct mechanical measurements of the elasticity of single DNA molecules using magnetic beads, Science, vol. 258, 1122-1126 (Nov. 13, 1992).
Soni, et al. Progress toward ultrafast DNA sequencing using solid-state nanopores. Clin Chem. Nov. 2007;53(11):1996-2001. Epub Sep. 21, 2007.
Southern, et al. Analyzing and comparing nucleic acid sequences by hybridization to arrays of oligonucleotides: evaluation using experimental models. Genomics. Aug. 1992;13(4):1008-17.
Martinez-Torrecuadradaet al.: Targeting the Extracellular Domain of Fibroblast Growth Factor Receptor 3 with Human Single-Chain Fv Antibodies Inhibits Bladder Carcinoma Cell Line Proliferation; Clinical Cancer Research; vol. 11; pp. 6282-6290 (2005).
Sierzchala, Agnieszka B. et al., Solid-phase oligodeoxynucleotide synthesis : a two-step cycle using peroxy anion deprotection, J. Am. Chem. Soc., vol. 125, No. 44, 13427-13441 (2003).
U.S. Appl. No. 15/187,714 Office Action dated Apr. 4, 2019.
U.S. Appl. No. 15/603,013 Office Action dated Jun. 26, 2019.
Sproat, et al. An efficient method for the isolation and purification of oligoribonucleotides. Nucleosides & Nucleotides. 1995; 14(1 &2):255-273.
Srivannavit et al., Design and fabrication of microwell array chips for a solution-based, photogenerated acid-catalyzed parallel oligonuclotide DNA synthesis. Sensors and Actuators A, 116:150-160, 2004.
Srivastava et al., RNA synthesis: phosphoramidites for Rna synthesis in the reverse direction. Highly efficient synthesis and application to convenient introduction of ligands, chromophores and modifications of synthetic RNA at the 3'-end, Nucleic Acids Symposium Series, 52(1):103-104, 2008.
Steel, The Flow-Thru Chip a Three-dimensional biochip platform. In: Schena, Microarray Biochip Technology, Chapter 5, Natick, MA: Eaton Publishing, 2000, 33 pages.
Stemmer, et al. Single-step assembly of a gene and entire plasmid from large numbers of oligodeoxyribonucleotides. Gene. Oct. 16, 1995;164(1):49-53.

(56) References Cited

OTHER PUBLICATIONS

Stryer. DNA Probes and genes can be synthesized by automated solid-phase methods. Biochemistry, 3rd edition, New York: W.H. Freeman and Company, 1988; 123-125.
Stutz, et al. Novel fluoride-labile nucleobase-protecting groups for the synthesis of 3'(2')-O-amino-acylated RNA sequences. Helv. Chim. Acta. 2000; 83(9):2477-2503.
Sullivan et al. Library construction and evaluation for site saturation mutagenesis. Enzyme Microb. Technol. 53:70-77 (2013).
Sun et al. Structure-Guided Triple-Code Saturation Mutagenesis: Efficient Tuning of the Stereoselectivity of an Epoxide Hydrolase. ACS Catal. 6:1590-1597 (2016).
Takahashi, Cell-free cloning using multiply-primed rolling circle amplification with modified RNA primers. Biotechniques. Jul. 2009;47(1):609-15. doi: 10.2144/000113155.
Tanase, M. et al., Magnetic trapping of multicomponent nanowires, The Johns Hopkins University, Baltimore, Maryland, p. 1-3 (Jun. 25, 2001).
Taylor et al., Impact of surface chemistry and blocking strategies on DNA microarrays. Nucleic Acids Research, 31(16):e87, 19 pages, 2003.
The Hood Laboratory, Beta Group. Assembly Manual for the POSaM: The ISB Piezoelelctric Oligonucleotide Synthesizer and Microarrayer, Inkjet Microarrayer Manual Version 1.2, 50 pages, May 28, 2004.
The SLIC, Gibson, CPEC and SLiCE assembly methods (and GeneArt Seamless, In-Fusion Cloning). 5 pages, available online Sep. 2, 2010.
Tian, et al. Accurate multiplex gene synthesis from programmable DNA microchips. Nature. Dec. 23, 2004;432(7020):1050-4.
Tsai et al., Dimeric CRISPR RNA-guided FokI nucleases for highly specific genome editing Nat. Biotechnol., 32(6):569-576, 2014.
Twist Bioscience | White Paper. DNA-Based Digital Storage. Retrieved from the internet, Twistbioscience.com, Mar. 27, 2018, 5 pages.
Unger, et al. Monolithic microfabricated valves and pumps by multilayer soft lithography. Science. Apr. 7, 2000;288(5463):113-6.
U.S. Appl. No. 14/241,874 Office Action dated Feb. 27, 2017.
U.S. Appl. No. 14/241,874 Office Action dated Jul. 14, 2016.
U.S. Appl. No. 14/241,874 Office Action dated May 4,2018.
U.S. Appl. No. 14/452,429 Office Action dated Oct. 21, 2015.
U.S. Appl. No. 14/452,429 Restriction Requirement dated Dec. 12, 2014.
U.S. Appl. No. 14/885,962 Notice of Allowance dated Nov. 8, 2017 and Sep. 29, 2017.
U.S. Appl. No. 14/885,962 Office Action dated Dec. 16, 2016.
U.S. Appl. No. 14/885,962 Office Action dated Sep. 8, 2016.
U.S. Appl. No. 14/885,962 Restriction Requirement dated Mar. 1, 2016.
U.S. Appl. No. 14/885,963 Notice of Allowance dated May 24, 2016.
U.S. Appl. No. 14/885,963 Office Action dated Feb. 5, 2016.
U.S. Appl. No. 14/885,965 Office Action dated Aug. 28, 2018.
U.S. Appl. No. 14/885,965 Office Action dated Aug. 30, 2017.
U.S. Appl. No. 14/885,965 Office Action dated Feb. 18, 2016.
U.S. Appl. No. 14/885,965 Office Action dated Jan. 4, 2018.
U.S. Appl. No. 14/885,965 Office Action dated Jul. 7, 2016.
U.S. Appl. No. 15/015,059 Final Office Action dated Jul. 17, 2019.
U.S. Appl. No. 15/015,059 Office Action dated Feb. 7, 2019.
U.S. Appl. No. 15/135,434 Notice of Allowance dated Feb. 9, 2018.
U.S. Appl. No. 15/135,434 Office Action dated Nov. 30, 2017.
U.S. Appl. No. 15/135,434 Restriction Requirement dated Jul. 12, 2017.
U.S. Appl. No. 15/151,316 Office Action dated Jun. 7, 2018.
U.S. Appl. No. 15/154,879 Notice of Allowance dated Feb. 1, 2017.
U.S. Appl. No. 15/156,134 Office Action dated Apr. 4, 2019.
U.S. Appl. No. 15/187,714 Restriction Requirement dated Sep. 17, 2018.
U.S. Appl. No. 15/187,721 Notice of Allowance dated Dec. 7, 2016.
U.S. Appl. No. 15/187,721 Office Action dated Oct. 14, 2016.
U.S. Appl. No. 15/233,835 Notice of Allowance dated Oct. 4, 2017.
U.S. Appl. No. 15/233,835 Office Action dated Feb. 8, 2017.
U.S. Appl. No. 15/233,835 Office Action dated Jul. 26, 2017.
U.S. Appl. No. 15/233,835 Restriction Requirement dated Nov. 4, 2016.
U.S. Appl. No. 15/245,054 Office Action dated Mar. 21, 2017.
U.S. Appl. No. 15/245,054 Office Action dated Oct. 19, 2016.
U.S. Appl. No. 15/268,422 Office Action dated Mar. 1, 2019.
U.S. Appl. No. 15/268,422 Restriction Requirement dated Oct. 4, 2018.
U.S. Appl. No. 15/377,547 Final Office Action dated Feb. 8, 2019.
U.S. Appl. No. 15/377,547 Office Action dated Jul. 27, 2018.
U.S. Appl. No. 15/377,547 Office Action dated Mar. 24, 2017.
U.S. Appl. No. 15/377,547 Office Action dated Nov. 30, 2017.
U.S. Appl. No. 15/433,909 Non-Final Office Action dated Feb. 8, 2019.
U.S. Appl. No. 15/433,909 Restriction Requirement dated Sep. 17, 2018.
U.S. Appl. No. 15/602,991 Final Office Action dated Dec. 13, 2018.
U.S. Appl. No. 15/602,991 Notice of Allowance dated Oct. 25, 2017.
U.S. Appl. No. 15/602,991 Office Action dated May 31, 2018.
U.S. Appl. No. 15/602,991 Office Action dated May 31, 2019.
U.S. Appl. No. 15/602,991 Office Action dated Sep. 21, 2017.
U.S. Appl. No. 15/603,013 Office Action dated Jan. 30, 2018.
U.S. Appl. No. 15/603,013 Office Action dated Jul. 10, 2018.
U.S. Appl. No. 15/603,013 Office Action dated Oct. 20, 2017.
U.S. Appl. No. 15/619,322 Office Action dated Aug. 14, 2019.
U.S. Appl. No. 15/682,100 Office Action dated Jan. 2, 2018.
U.S. Appl. No. 15/682,100 Restriction Requirement dated Nov. 8, 2017.
U.S. Appl. No. 15/709,274 Notice of Allowance dated Apr. 3, 2019.
U.S. Appl. No. 15/729,564 Final Office Action dated Dec. 13, 2018.
U.S. Appl. No. 15/729,564 Office Action dated Jan. 8, 2018.
U.S. Appl. No. 15/729,564 Office Action dated Jun. 6, 2018.
U.S. Appl. No. 15/729,564 Office Action dated May 30, 2019.
U.S. Appl. No. 15/816,995 Restriction Requirement dated Apr. 4, 2019.
U.S. Appl. No. 15/844,395 Restriction Requirement dated May 17, 2019.
U.S. Appl. No. 15/860,445 Final Office Action dated Dec. 13, 2018.
U.S. Appl. No. 15/860,445 Office Action dated May 30, 2018.
U.S. Appl. No. 15/921,479 Restriction Requirement dated May 24, 2019.
U.S. Appl. No. 14/452,429 Office Action mailed Apr. 9, 2015.
U.S. Appl. No. 15/151,316 Final Office Action dated Feb. 21, 2019.
Vaijayanthi, et al. Recent advances in oligonucleotide synthesis and their applications. Indian J Biochem Biophys. Dec. 2003;40(6):377-91.
Van Den Brulle, et al. A novel solid phase technology for high-throughput gene synthesis. Biotechniques. 2008; 45(3):340-343.
Van Der Werf et al. Limonene-1,2-epoxide hydrolase from Rhodococcus erythropolis DCL14 belongs to a novel class of epoxide hydrolases. J. Bacteriol. 180:5052-5057 (1998).
Van Tassell et al., SNP discovery and allele frequency estimation by deep sequencing of reduced representation libraries. Nature Methods, 5:247-252, 2008.
Vargeese, et al. Efficient activation of nucleoside phosphoramidites with 4,5-dicyanoimidazole during oligonucleotide synthesis. Nucleic Acids Res. Feb. 15, 1998;26(4):1046-50.
Verma et al. Modified oligonucleotides: synthesis and strategy for users. Annu Rev Biochem 67:99-134 (1998).
Vincent, et al. Helicase-dependent isothermal DNA amplification. EMBO Rep. Aug. 2004;5(8):795-800.
Visscher et al., Construction of multiple-beam optical traps with nanometer-resolution position sensing, IEEE Journal of Selected Topics in Quantum Electronics, vol. 2, No. 4, 1066-1076 (Dec. 1996).
Voldmans Joel et al., Holding forces of single-particle dielectrophoretic traps. Biophysical Journal, vol. 80, No. 1, 531-541 (Jan. 2001).
Vos, et al. AFLP:A new technique for DNA fingerprinting. Nucleic Acids Res. Nov. 11, 1995;23(21):4407-14.

(56) References Cited

OTHER PUBLICATIONS

Wagner et al., Nucleotides, Part LXV, Synthesis of 2'-Deoxyribonucleoside 5'-Phosphoramidites: New Building Blocks for the Inverse (5'-3')-Oligonucleotide Approach. Helvetica Chimica Acta, 83(8):2023-2035, 2000.
Wah, David A. et al., Structure of Fok I has implications for DNA cleavage, Proc. Natl. Acad. Sci. USA, vol. 95, 10564-10569 (Sep. 1998).
Wah, David A. et al., Structure of the multimodular endonuclease Fok I bound to DNA, Nature, vol. 388, 97-100 (Jul. 1997).
Walker, et al. Strand displacement amplification—an isothermal, in vitro DNA amplification technique. Nucleic Acids Res. Apr. 11, 1992;20(7):1691-6.
Wan et al., Deep Learning for Content-Based Image Retrieval: A comprehensive study. In Proceedings of the 22nd ACM International Conference on Multimedia—Nov. 3-7, 2014, Orlando, FL, p. 157-166, 2014.
Warr et al. Exome Sequencing: current and future perspectives. G3: (Bethesda) 5(8):1543-1550 (2015).
Weber, et al. A modular cloning system for standardized assembly of multigene constructs. PLoS One. Feb. 18, 2011;6(2):e16765. doi: 10.1371/journal.pone.0016765.
Welz, et al. 5-(Benzylmercapto)-1H-tetrazole as activator for 2'-O-TBDMS phosphoramidite building blocks in RNA synthesis. Tetrahedron Lett. 2002; 43(5):795-797.
Westin et al., Anchored multiplex amplification on a microelectronic chip array Nature Biotechnology, 18:199-202 (2000) (abstract only).
Whitehouse, Adrian et al. Analysis of the mismatch and insertion/deletion binding properties of Thermus thermophilus, HB8, MutS, Biochemical and Biophysical Research Communications, vol. 233, 834-837 (1997).
Wiedenheft et al., RNA-guided genetic silencing systems in bacteria and archaea. Nature, 482:331-338, 2012.
Wijshoff, Herman. Structure and fluid-dynamics in Piezo inkjet printheads. Thesis. Venio, The Netherlands, published 2008, p. 1-185.
Wirtz, Denis, Direct measurement of the transport properties of a single DNA molecule, Physical Review Letters, vol. 75, No. 12, 2436-2439 (Sep. 18, 1995).
Withers-Martinez, Chrislaine et al., PCR-based gene synthesis as an efficient approach for expression of the A+ T-rich malaria genome, Protein Engineering, vol. 12, No. 12, 1113-1120 (1999).
Wood, Richard D. et al., Human DNA repair genes, Science, vol. 291, 1284-1289 (Feb. 16, 2001).
Wosnick, et al. Rapid construction of large synthetic genes: total chemical synthesis of two different versions of the bovine prochymosin gene. Gene. 1987;60(1):115-27.
Wright and Church, An open-source oligomicroarray standard for human and mouse. Nature Biotechnology, 20:1082-1083, 2002.
Wu, et al. Sequence-Specific Capture of Protein-DNA Complexes for Mass Spectrometric Protein Identification PLoS ONE. Oct. 20, 2011, vol. 6, No. 10.
Wu, et al. RNA-mediated gene assembly from DNA arrays. Angew Chem Int Ed Engl. May 7, 2012;51(19):4628-32. doi: 10.1002/anie.201109058.
Wu, et al. Specificity of the nick-closing activity of bacteriophage T4 DNA ligase. Gene. 1989;76(2):245-54.
Wu, Xing-Zheng et al., An improvement of the on-line electrophoretic concentration method for capillary electrophoresis of proteins an experimental factors affecting he concentration effect, Analytical Sciences, vol. 16, 329-331 (Mar. 2000).
Xiong, et al. A simple, rapid, high-fidelity and cost-effective PCR-based two-step DNA synthesis method for long gene sequences. Nucleic Acids Res. 2004, 32(12):e98.
Xiong et al., Chemical gene synthesis: Strategies, softwares, error corrections, and applications. FEMS Microbiol. Rev., 32:522-540, 2008.
Xiong, et al. Non-polymerase-cycling-assembly-based chemical gene synthesis: Strategies, methods, and progress. Biotechnology Advances. 26(2):121-134, 2008.
Xu et al., Design of 240,000 orthogonal 25mer DNA barcode probes. PNAS, 106(7):2289-2294, 2009.
Yang et al. Purification, cloning, and characterization of the CEL I nuclease, Biochemistry, 39(13):3533-35, 2000.
Yazdi et al., A Rewritable, Random-Access DNA-Based Storage System, Scientific Reports, 5, Article No. 14138, 27 pagse, 2015.
Yehezkel et al., De novo DNA synthesis using single molecule PCR Nucleic Acids Research, 36(17):e107, 2008.
Yes HMDS vapor prime process application note Prepared by UC Berkeley and University of Texas at Dallas and re-printed by Yield Engineering Systems, Inc., 6 pages (http://www.yieldengineering.com/Portals/0/HMDS%20Application%20Note.pdf (Published online Aug. 23, 2013).
Youil, Rima et al., Detection of 81 of 81 known mouse Beta-Giobin promoter mutations with T4 Endonuclease VII• The EMC Method, Genomics, 32:431-435, 1996.
Young et al. Two-step total gene synthesis method. Nucleic Acids Res. 32(7):e59, 2004.
Zhang and Seelig, Dynamic DNA nanotechnology using strand-displacement reactions, Nat. Chem., 3(2):103-113, 2011.
Zheleznaya et al. Nicking endonucleases. Biochemistry (Mosc). 74(13):1457-66, 2009.
Zheng et al. Manipulating the Stereoselectivity of Limonene Epoxide Hydrolase by Directed Evolution Based on Iterative Saturation Mutagenesis. J. Am. Chem. Soc. 132:15744-15751 (2010).
Zhirnov et al., Nucleic acid memory. Nature Materials, 15:366, 2016.
Zhou et al. Establishment and application of a loop-mediated isothermal amplification (LAMP) system for detection of cry1Ac transgenic sugarcane Scientific Reports May 9, 2014, vol. 4, No. 4912.
Zhou et al., Microfluidic PicoArray synthesis of oligodeoxynucleotides and simultaneous assembling of multiple DNA sequences Nucleic Acids Research, 32(18):5409-5417, 2004.
European Patent Application No. 16871446.7 First Official Action dated Nov. 13, 2019.
Galka et al.: QuickLib, a method for building fully synthetic plasmid libraries by seamless cloning of degenerate oligonucleotides. PLOS ONE, 12, e0175146:1-9 (2017).
Galka et al.: QuickLib, a method for building fully synthetic plasmid libraries by seamless cloning of degenerate oligonucleotides. PLOS ONE, 12, e0175146:S1 figure (2017).
Galka et al.: QuickLib, a method for building fully synthetic plasmid libraries by seamless cloning of degenerate oligonucleotides. PLOS ONE, 12, e0175146:S1 Table (2017).
Galka et al.: QuickLib, a method for building fully synthetic plasmid libraries by seamless cloning of degenerate oligonucleotides. PLOS ONE, 12, e0175146:S2 figure (2017).
International Application No. PCT/US2018/019268 International Preliminary Report on Patentability dated Sep. 6, 2019.
International Application No. PCT/US2019/032992 International Search Report and Written Opinion dated Oct. 28, 2019.
International Application No. PCT/US2019/032992 Invitation to Pay Additional Fees dated Sep. 6, 2019.
U.S. Appl. No. 14/241,874 Final Office Action dated Jan. 28, 2019.
U.S. Appl. No. 14/452,429 Notice of Allowance dated Jun. 7, 2016.
U.S. Appl. No. 14/885,965 Office Action dated Feb. 10, 2017.
U.S. Appl. No. 15/015,059 Office Action dated Aug. 19, 2019.
U.S. Appl. No. 15/151,316 Office Action dated Oct. 4, 2019.
U.S. Appl. No. 15/156,134 Final Office Action dated Jan. 3, 2020.
U.S. Appl. No. 15/187,714 Final Office Action dated Sep. 17, 2019.
U.S. Appl. No. 15/268,422 Final Office Action dated Oct. 3, 2019.
U.S. Appl. No. 15/603,013 Final Office Action dated Nov. 6, 2019.
U.S. Appl. No. 15/816,995 Office Action dated Sep. 20, 2019.
U.S. Appl. No. 15/835,342 Office Action dated Dec. 2, 2019.
U.S. Appl. No. 15/835,342 Restriction Requirement dated Sep. 10, 2019.
U.S. Appl. No. 15/844,395 Office Action dated Jan. 24, 2020.
U.S. Appl. No. 15/921,479 Office Action dated Nov. 12, 2019.
U.S. Appl. No. 15/960,319 Office Action dated Aug. 16, 2019.

(56) References Cited

OTHER PUBLICATIONS

U.S. Appl. No. 16/006,581 Office Action dated Sep. 25, 2019.
U.S. Appl. No. 16/384,678 Office Action dated Jan. 21, 2020.
U.S. Appl. No. 16/409,608 Office Action dated Sep. 9, 2019.
U.S. Appl. No. 16/530,717 Office Action dated Sep. 6, 2019.
U.S. Appl. No. 16/535,777 Office Action dated Jan. 23, 2020.
Paul et al.: Acid binding and detritylation during oligonucleotide synthesis. Nucleic Acids Research. 15. pp. 3048-3052 (1996).
Pierce and Wangh, Linear-after-the-exponential polymerase chain reaction and allied technologies Real-time detection strategies for rapid, reliable diagnosis from single cells Methods Mol. Med. 132:65-85 (2007) (Abstract only).
PubChem Data Sheet Acetonitrile. Printed from website https://pubchem.ncbi.nlm.nig.gov/ pp. 1-124 (2020).
PubChem Data Sheet Methylene Chloride. Printed from website https://pubchem.ncbi.nlm.nig.gov/ pp. 1-140 (2020).
Rajpal et al.: A general method for greatly improving the affinity of antibodies by using combinatorial libraries. Proc. Natl. Acad. Sci. 102(24):8466-8471 (2005).
Solomon et al.: Genomics at Agilent: Driving Value in DNA Sequencing.https://www.agilent.com/labs/features/2010_genomics.html, 8 pages (Aug. 5, 2010).
U.S. Appl. No. 15/619,322 Final Office Action dated Mar. 30, 2020.
U.S. Appl. No. 15/991,992 Restriction Requirement dated Mar. 10, 2020.
U.S. Appl. No. 16/165,952 Office Action dated Mar. 12, 2020.
U.S. Appl. No. 16/535,779 First Action Interview dated Feb. 10, 2020.
U.S. Appl. No. 15/921,537 Office Action dated Apr. 1, 2020.
Cui et al.: Information Security Technology Based on DNA Computing. International Workshop on Anti-Counterfeiting, Security and Identification (ASID); IEEE Xplore 4 pages (2007).
European Patent Application No. 17844060.8 Extended Search Report dated Apr. 20, 2020.
European Patent Application No. 17872347.4 Extended European Search Report dated Jun. 30, 2020.
European Patent Application No. 17881617.9 European Search Report and Written Opinion dated Jul. 2, 2020.
Hopcroft et al.: What is the Young's Modulus of Silicon?. Journal of Microelectromechanical Systems. 19(2):229-238 (2010).
Hötzel et al.: A strategy for risk mitigation of antibodies with fast clearance. mAbs, 4(6), 753-760 (2012). doi:10.4161/mabs.22189 https://www.ncbi.nlm.nih.gov/pubmed/23778268.
Jaiswal et al.: An architecture for creating collaborative semantically capable scientific data sharing infrastructures. Proceeding WIDM '06 Proceedings of the 8th annual ACM international workshop on Web information and data management. ACM Digital Library pp. 75-82 (2006).
PCT/US2018/037152 International Preliminary Report on Patentability dated Dec. 17, 2019.
PCT/US2018/037161 International Preliminary Report on Patentability dated Dec. 17, 2019.
PCT/US2018/050511 International Preliminary Report on Patentability dated Mar. 17, 2020.
PCT/US2018/056783 International Preliminary Report on Patentability dated Apr. 30, 2020.
PCT/US2018/057857 International Preliminary Report on Patentability dated Apr. 28, 2020.
PCT/US2019/012218 International Preliminary Report on Patentability dated Jul. 16, 2020.
PCT/US2019/068435 International Search Report and Written Opinion dated Apr. 23, 2020.
PCT/US2020/019371 International Search Report and Written Opinion dated Jun. 25, 2020.
PCT/US2020/019986 International Search Report and Written Opinion dated Jul. 29, 2020.
PCT/US2020/019986 Invitation to Pay Additional Fees dated Jun. 5, 2020.
PCT/US2020/019988 International Search Report and Written Opinion dated Jul. 29, 2020.
PCT/US2020/019988 Invitation to Pay Additional Fees dated Jun. 8, 2020.
U.S. Appl. No. 15/151,316 Final Office Action dated Jul. 9, 2020.
U.S. Appl. No. 15/272,004 Office Action dated Jun. 12, 2020.
U.S. Appl. No. 15/816,995 Office Action dated May 19, 2020.
U.S. Appl. No. 15/835,342 Final Office Action dated Sep. 8, 2020.
U.S. Appl. No. 15/921,479 Final Office Action dated Jun. 15, 2020.
U.S. Appl. No. 15/991,992 Office Action dated May 21, 2020.
U.S. Appl. No. 16/031,784 Office Action dated May 12, 2020.
U.S. Appl. No. 16/039,256 Office Action dated Aug. 20, 2020.
U.S. Appl. No. 16/039,256 Restriction Requirement dated May 18, 2020.
U.S. Appl. No. 16/128,372 Office Action dated Oct. 8, 2020.
U.S. Appl. No. 16/128,372 Restriction Requirement dated May 18, 2020.
U.S. Appl. No. 16/530,717 Final Office Action dated Apr. 15, 2020.
Van der Velde: Thesis. Finding the Strength of Glass. Delft University of Technology. 1-16 (2015).
European Patent Application No. 18756866.2 Partial Search Report dated Nov. 24, 2020.
Geetha et al.: Survey on Security Mechanisms for Public Cloud Data. 2016 International Conference on Emerging Trends in Engineering, Technology and Science (ICETETS). 8 pages (2016).
O'Driscoll et al.: Synthetic DNA: The next generation of big data storage. Bioengineered. 4(3):123-125 (2013).
Shipman et al.: Molecular recordings by directed CRISPR spacer acquisition. Science. 353(6298):1-16 (2016).
Yazdi et al.: DNA-Based Storage: Trends and Methods. IEEE Transactions on Molecular, Biological and Multi-Scale Communications. IEEE. 1(3):230-248 (2016).

\* cited by examiner

DNA-BASED DIGITAL INFORMATION STORAGE WITH SIDEWALL ELECTRODES

CROSS-REFERENCE

This application claims the benefit of U.S. provisional patent application No. 62/613,728 filed on Jan. 4, 2018; U.S. provisional patent application No. 62/617,067 filed on Jan. 12, 2018; and U.S. provisional patent application No. 62/650,231 filed on Mar. 29, 2018, all of which are incorporated herein by reference in their entirety.

BACKGROUND

Biomolecule based information storage systems, e.g., DNA-based, have a large storage capacity and stability over time. However, there is a need for scalable, automated, highly accurate and highly efficient systems for generating biomolecules for information storage.

BRIEF SUMMARY

Provided herein are devices for storing information, comprising: a solid support, wherein the solid support comprises a plurality of wells, wherein each of the wells comprises an addressable locus comprising: a synthesis surface located in a bottom region of each of the wells; a bottom electrode in addressable communication with the synthesis surface; and at least one sidewall electrode located on a sidewall of each of the wells, wherein the at least one sidewall electrode is 50 nm to 200 nm from the bottom region. Further provided herein are devices wherein the solid support comprises addressable loci at a density of at least $100 \times 10^6$ addressable loci per $cm^2$. Further provided herein are devices wherein the solid support comprises addressable loci at a density of $100 \times 10^6$ to $100 \times 10^7$ addressable loci per $cm^2$. Further provided herein are devices wherein the addressable locus comprises a diameter up to about 750 nm. Further provided herein are devices wherein each of the wells comprises a depth up to about 1000 nm. Further provided herein are devices wherein each of the wells comprises a depth of 100 nm to 1000 nm. Further provided herein are devices wherein each of the wells comprises a longest cross-sectional diameter of 100 nm to 800 nm. Further provided herein are devices wherein each of the wells is cylindrical. Further provided herein are devices wherein the bottom electrode comprises a largest cross-sectional area of $10^4$ $nm^2$ to $10^5$ $nm^2$. Further provided herein are devices wherein the at least one sidewall electrode is 50 nm to 200 nm from the bottom region. Further provided herein are devices wherein the at least one sidewall electrode comprises a height of 5 nm to 25 nm. Further provided herein are devices comprising at least two sidewall electrodes. Further provided herein are devices wherein the at least one sidewall electrode and the bottom electrode are independently addressable.

Provided herein are devices for storing information, comprising: a solid support, wherein the solid support comprises a plurality of wells, wherein each of the wells comprises an addressable locus comprising: a synthesis surface located in a bottom region of each of the wells; a bottom electrode in addressable communication with the synthesis surface; at least one sidewall electrode located on a sidewall of each of the wells, wherein the synthesis surface at each addressable locus comprises at least one polynucleotide extending from the synthesis surface, and wherein the polynucleotides comprising different sequences on the solid support are present at a density of at least $100 \times 10^6$ polynucleotides per $cm^2$. Further provided herein are devices wherein the solid support comprises polynucleotides of different sequences at a density of at least $100 \times 10^7$ polynucleotides per $cm^2$. Further provided herein are devices wherein the solid support comprises addressable loci at a density of $100 \times 10^6$ to $100 \times 10^7$ polynucleotides per $cm^2$. Further provided herein are devices wherein each of the wells comprises a depth up to about 1000 nm. Further provided herein are devices wherein each of the wells comprises a depth of 100 nm to 1000 nm. Further provided herein are devices wherein the addressable locus comprises a diameter up to about 750 nm. Further provided herein are devices wherein each of the wells comprises a longest cross-sectional diameter of 100 nm to 800 nm. Further provided herein are devices wherein each of the wells is cylindrical. Further provided herein are devices wherein the bottom electrode comprises a largest cross-sectional area of $10^4$ $nm^2$ to $10^5$ $nm^2$. Further provided herein are devices wherein the at least one sidewall electrode is 50 nm to 200 nm from the bottom region. Further provided herein are devices wherein the at least one sidewall electrode comprises a height of 5 nm to 25 nm. Further provided herein are devices comprising at least two sidewall electrodes. Further provided herein are devices wherein the at least one sidewall electrode and the base electrode are independently addressable.

Provided herein are methods for storing information, comprising: (a) providing a device described herein; (b) providing instructions for polynucleotide synthesis; (c) depositing at least one nucleoside on the synthesis surface, wherein the at least one nucleoside couples to a polynucleotide attached to the synthesis surface; and (d) repeating step c) to synthesize a plurality of polynucleotides on the synthesis surface, wherein the instructions comprise at least one sequence encoding for the plurality of polynucleotides. Further provided herein are methods further comprising cleaving at least one polynucleotide from the surface, wherein the polynucleotide is dissolved in a droplet. Further provided herein are methods further comprising sequencing at least one polynucleotide from the surface. Further provided herein are methods wherein the nucleoside comprises a nucleoside phosphoramidite. Further provided herein are methods further comprising a cleavage step, wherein the cleavage step comprises applying an electrical potential to the bottom electrode to generate a cleavage reagent. Further provided herein are methods wherein the method further comprises drying the surface. Further provided herein are methods further comprising washing the nucleosides away from the surface. Further provided herein are methods wherein the method further comprises a capping step. Further provided herein are methods wherein the method further comprises an oxidation step. Further provided herein are methods wherein the method further comprises a deblocking step, wherein the deblocking step comprises applying an electrical potential to the at least one sidewall electrode to generate a deprotection reagent.

Provided herein are methods for storing information, comprising: (a) providing a solid support comprising a surface; (b) depositing at least one nucleoside on the surface, wherein the at least one nucleoside couples to a polynucleotide attached to the surface; and (c) repeating step b) to synthesize a plurality of polynucleotides on the surface, wherein polynucleotides having different sequences on the surface are present at a density of at least $100 \times 10^6$ polynucleotides per $cm^2$. Further provided herein are methods wherein the density of addressable loci on the solid support is at least $100 \times 10^7$ polynucleotides per $cm^2$. Further provided herein are methods wherein the density of addressable loci on the solid support is $100 \times 10^6$ to $100 \times 10^7$ polynucleotides per cm$^2$. Further provided herein are methods wherein the method further comprises cleaving at least one polynucleotide from the surface, wherein the polynucleotide is dissolved in a droplet. Further provided herein are methods wherein the method further comprises sequencing at least one polynucleotide from the surface. Further provided herein are methods wherein the nucleoside comprises a nucleoside phosphoramidite. Further provided herein are methods wherein the method further comprises drying the surface. Further provided herein are methods wherein the method further comprises washing the nucleosides away from the surface. Further provided herein are methods wherein the method further comprises a capping step. Further provided herein are methods wherein the method further comprises an oxidation step. Further provided herein are methods wherein the method further comprises a deblocking step.

Provided herein are methods for storing information, comprising: (a) providing a solid support comprising a surface; (b) depositing at droplet comprising at least one nucleoside on the surface, wherein the at least one nucleoside couples to a polynucleotide attached to the surface; and (c) repeating step b) to synthesize a plurality of polynucleotides on the surface, wherein the droplet has a volume of less than about 100 femtoliters. Further provided herein are methods wherein the droplet has a volume of less than about 50 femtoliters. Further provided herein are methods wherein the droplet has a volume of less than about 25 femtoliters to 100 femtoliters. Further provided herein are methods wherein the method further comprises cleaving at least one polynucleotide from the surface, wherein the polynucleotide is dissolved in a droplet. Further provided herein are methods wherein the method further comprises sequencing at least one polynucleotide from the surface. Further provided herein are methods wherein the nucleoside comprises a nucleoside phosphoramidite. Further provided herein are methods wherein the method further comprises drying the surface. Further provided herein are methods wherein the method further comprises washing the nucleosides away from the surface. Further provided herein are methods wherein the method further comprises a capping step. Further provided herein are methods wherein the method further comprises an oxidation step. Further provided herein are methods wherein the method further comprises a deblocking step.

Provided herein are methods for storing information, comprising: (a) providing a solid support comprising a surface; (b) depositing at least one nucleoside on the surface, wherein the at least one nucleoside couples to a polynucleotide attached to the surface; and (c) repeating step b) to synthesize a plurality of polynucleotides on the surface, wherein the time to repeat step b) using four different nucleotides is less than about 100 milliseconds. Further provided herein are methods wherein the time to repeat step b) using four different nucleotides is less than about 50 milliseconds. Further provided herein are methods wherein the time to repeat step b) using four different nucleotides is 25 milliseconds to 100 milliseconds. Further provided herein are methods wherein the method further comprises cleaving at least one polynucleotide from the surface, wherein the polynucleotide is dissolved in a droplet. Further provided herein are methods further comprising sequencing at least one polynucleotide from the surface. Further provided herein are methods wherein the nucleoside comprises a nucleoside phosphoramidite. Further provided herein are methods wherein the method further comprises drying the surface. Further provided herein are methods wherein the method further comprises washing the nucleosides away from the surface. Further provided herein are methods wherein the method further comprises a capping step. Further provided herein are methods wherein the method further comprises an oxidation step. Further provided herein are methods wherein the method further comprises a deblocking step.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
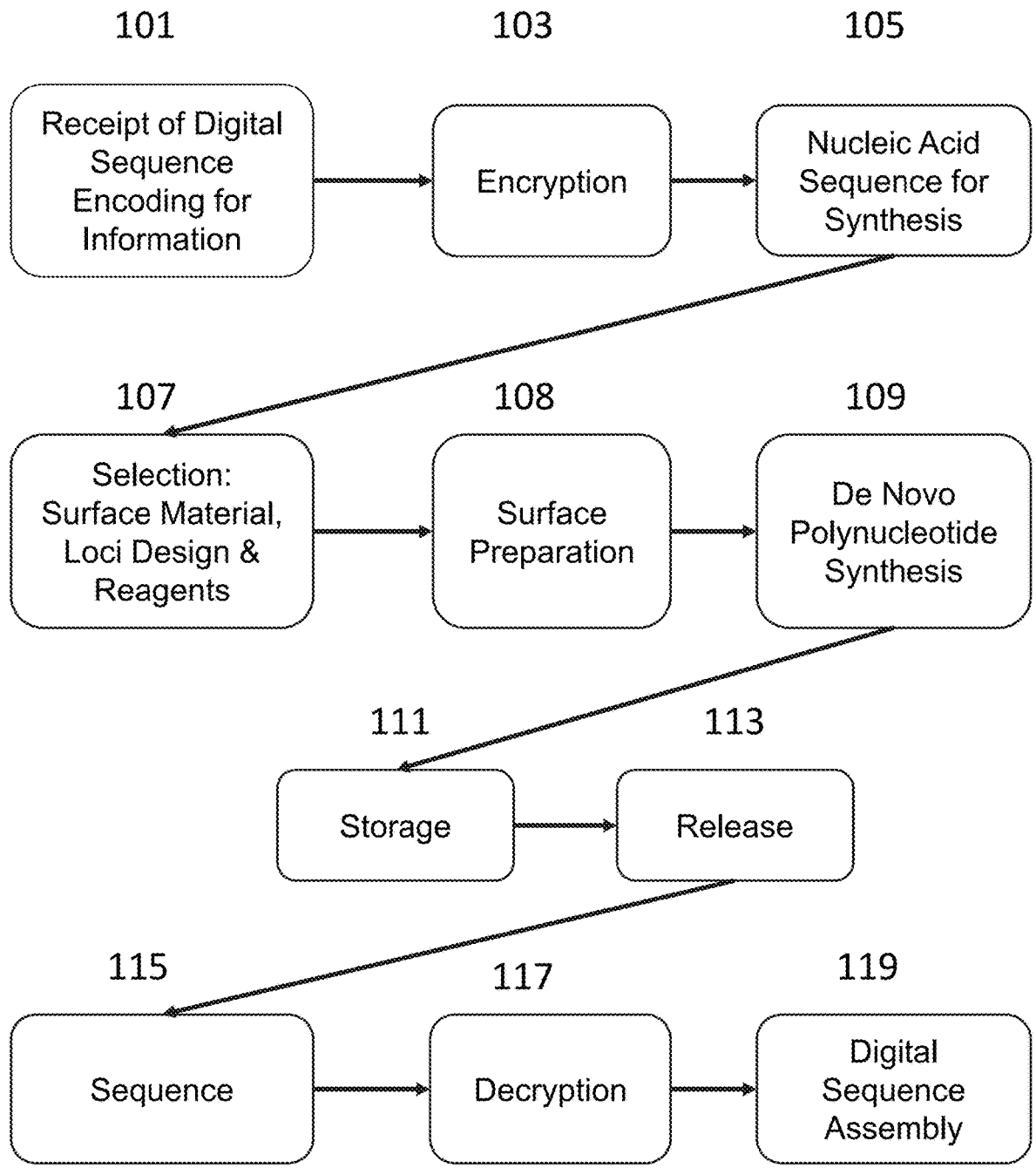
FIG. 1 illustrates an exemplary workflow for nucleic acid-based data storage.

There is a need for larger capacity storage systems as the amount of information generated and stored is increasing exponentially. Traditional storage media have a limited capacity and require specialized technology that changes with time, requiring constant transfer of data to new media, often at a great expense. A biomolecule such as a DNA molecule provides a suitable host for information storage in-part due to its stability over time and capacity for four bit information coding, as opposed to traditional binary information coding. Thus, large amounts of data are encoded in the DNA in a relatively smaller amount of physical space than used by commercially available information storage devices. Provided herein are methods to increase DNA synthesis throughput through increased sequence density and decreased turn-around time.

Definitions

Unless defined otherwise, all technical and scientific terms used herein have the same meaning as is commonly understood by one of ordinary skill in the art to which these inventions belong.

Throughout this disclosure, numerical features are presented in a range format. It should be understood that the description in range format is merely for convenience and brevity and should not be construed as an inflexible limitation on the scope of any embodiments. Accordingly, the description of a range should be considered to have specifically disclosed all the possible subranges as well as individual numerical values within that range to the tenth of the unit of the lower limit unless the context clearly dictates otherwise. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual values within that range, for example, 1.1, 2, 2.3, 5, and 5.9. This applies regardless of the breadth of the range. The upper and lower limits of these intervening ranges may independently be included in the smaller ranges, and are also encompassed within the invention, subject to any specifically excluded limit in the stated range. Where the stated range includes one or both of the limits, ranges excluding either or both of those included limits are also included in the invention, unless the context clearly dictates otherwise.

The terminology used herein is for the purpose of describing particular embodiments only and is not intended to be limiting of any embodiment. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers +/−10% thereof, or 10% below the lower listed limit and 10% above the higher listed limit for the values listed for a range.

As used herein, the terms "preselected sequence", "predefined sequence" or "predetermined sequence" are used interchangeably. The terms mean that the sequence of the polymer is known and chosen before synthesis or assembly of the polymer. In particular, various aspects of the invention are described herein primarily with regard to the preparation of nucleic acids molecules, the sequence of the polynucleotide being known and chosen before the synthesis or assembly of the nucleic acid molecules.

Provided herein are methods and compositions for production of synthetic (i.e. de novo synthesized or chemically synthesized) polynucleotides. Polynucleotides may also be referred to as oligonucleotides or oligos. Polynucleotide sequences described herein may be, unless stated otherwise, comprise DNA or RNA.

Solid Support Based Nucleic Acid Synthesis and Storage

Described herein are devices, compositions, systems and methods for chip based nucleic acid synthesis and storage. In some instances, polynucleotides are de novo synthesized using solid support based methods as described herein. In some instances, polynucleotides are stored on a solid support following synthesis. In some instances, solid support based methods as described herein are used for storage only.

Described herein are devices, compositions, systems and methods for solid support based nucleic acid synthesis and storage, wherein one or more nucleic acid synthesizer components are integrated into a solid support. Components or functional equivalents of components may comprise temperature control units, addressable electrodes, semiconducting surfaces, fluid reservoirs, fluidics, synthesis surfaces, power sources, or other component used to synthesize polynucleotides. Any combination of integrated components is suitable for use with the devices, compositions, systems and methods described herein. In some instances, one or more components is external (non-integrated) to the solid support.

Figure 15:
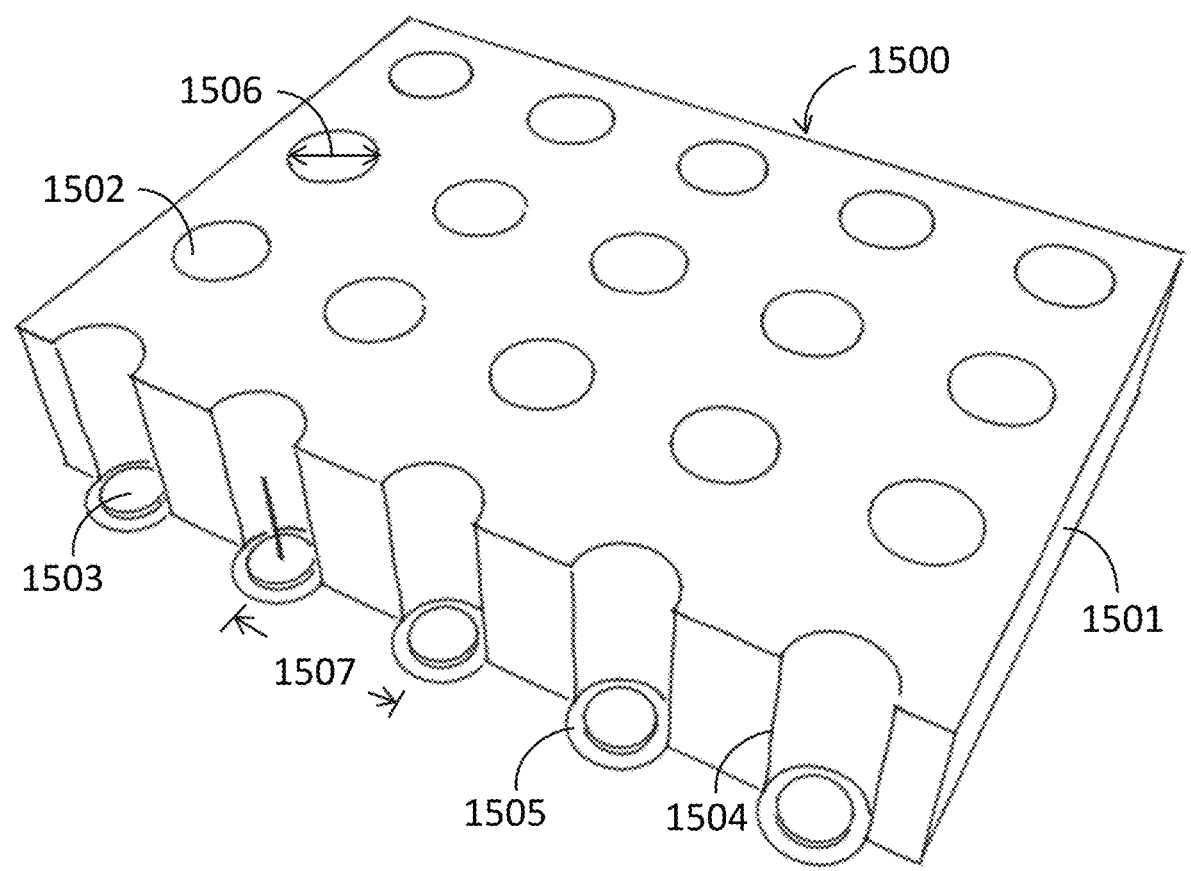
FIG. 15 depicts a solid support comprising addressable regions for nucleic acid synthesis or storage.
Figure 19:
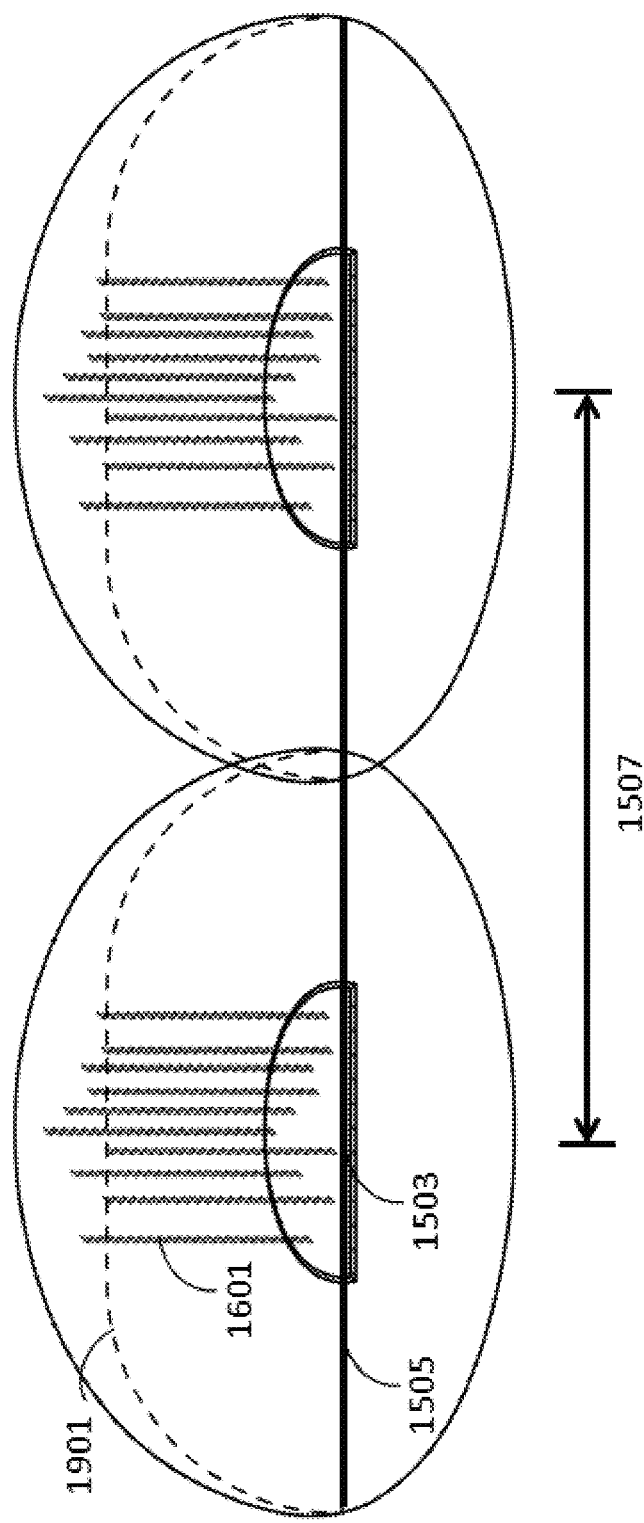
FIG. 19 illustrates an example of a solid support array, wherein the pitch approximates the length of a 240 mer polynucleotide.

The density of unique loci for polynucleotide synthesis on a surface is often controlled by the spatial resolution achievable by reagent deposition. Additionally, reagent deposition at unique sites requires movement of either the deposition device or the receiving surface to move the site of reagent deposition from one site to another. Alternatively, coupling of bases is locally controlled at defined sites on a synthesis surface without movement of the surface or a reagent deposition device. Local control is achieved through an array of addressable electrodes 1503, wherein each electrode controls nucleoside (nucleoside phosphoramidite) coupling through electrochemistry at a specific loci on the surface 1505. In some instances, an electrode is a base electrode (or bottom electrode), located at a bottom region in addressable communication with the synthesis surface. In some instances, electrodes are sidewall electrodes, located in the side of a well. However, the conventional process of electrochemistry on a flat array in some instances is limited by the pitch distance (See FIG. 19). At high densities (e.g., short pitch distance 1507), the length of growing DNA oligos 1601 can reach from one synthesis site to the adjacent ones, mixing discrete reaction products. To avoid mixing of adjacent reaction products, the pitch distance 1507 in some embodiments is increased. Diffusion through the liquid reaction medium 1901 is an additional factor which influences spatial control of polynucleotide synthesis. Thus, it is advantageous to isolate active sites to achieve higher array densities. Nucleoside coupling is controlled by local electrodes through any number of manipulations such as generation of local chemical reagents, local removal of reagents, repulsion of reagents, restriction of solvent, attraction of solvent, or other electrochemical or physical manipulation that influences one or more steps in base coupling. In a some instances, a device 1500 comprising a plate 1501 with wells 1502 is used to synthesize polynucleotides (See FIG. 15). The bottom of each well 1505 comprises an electrode 1503 from which polynucleotides are synthesized. Each well has a cross-sectional diameter 1506, and a pitch distance between any two wells 1507. The sidewalls 1504 of the electrode in some instances comprise one or more sidewall electrodes (not shown).

Figure 16A:
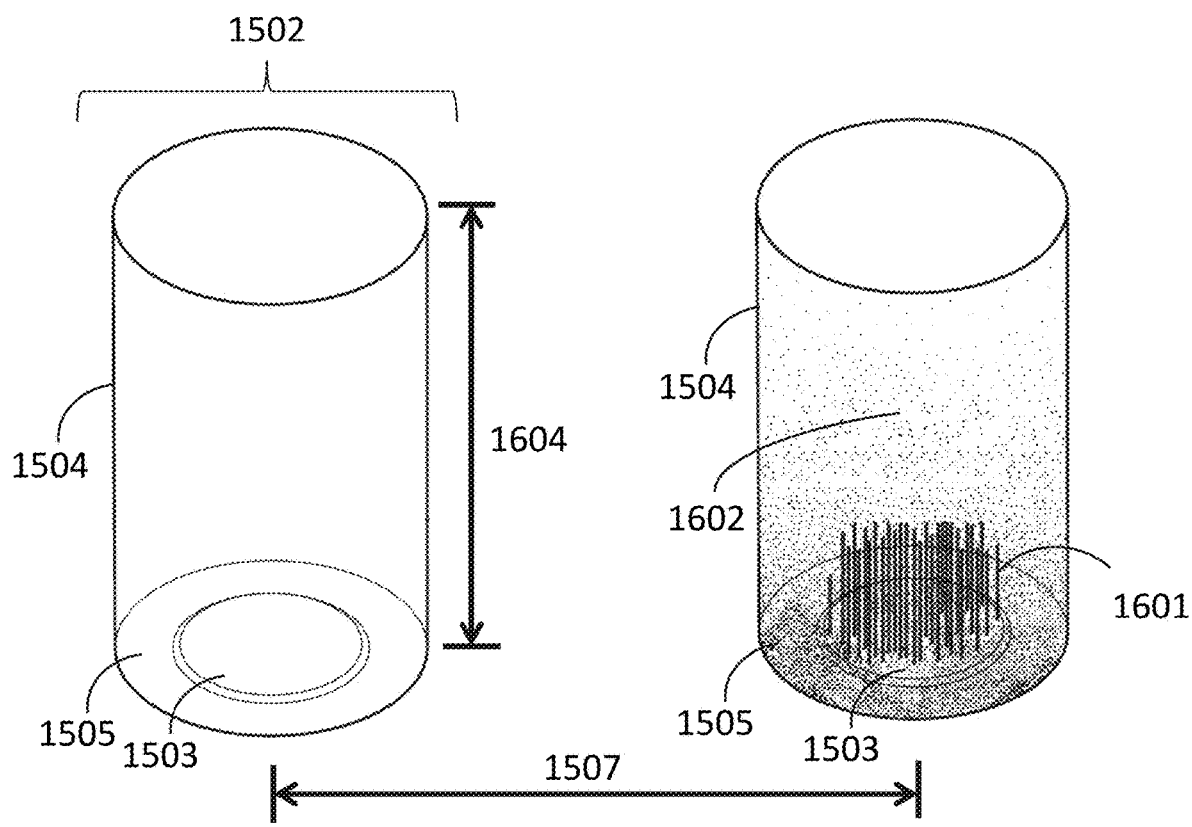
FIG. 16A depicts an array for synthesis using electrochemistry.

Coupling in some instances is controlled directly by control of the nucleoside addition step, a deprotection step, or other step that affects the efficiency of a nucleoside coupling reaction. In some instances, a pattern of electrodes are charged to generate a gradient of $H^+$ ions 1602 on defined sites near the synthesis surface (See FIG. 16A); the polynucleotides 1601 at these sites are unblocked (wherein the polynucleotide is blocked with an acid-cleavable blocking group) and will be available for coupling to nucleosides.

Figure 16B:
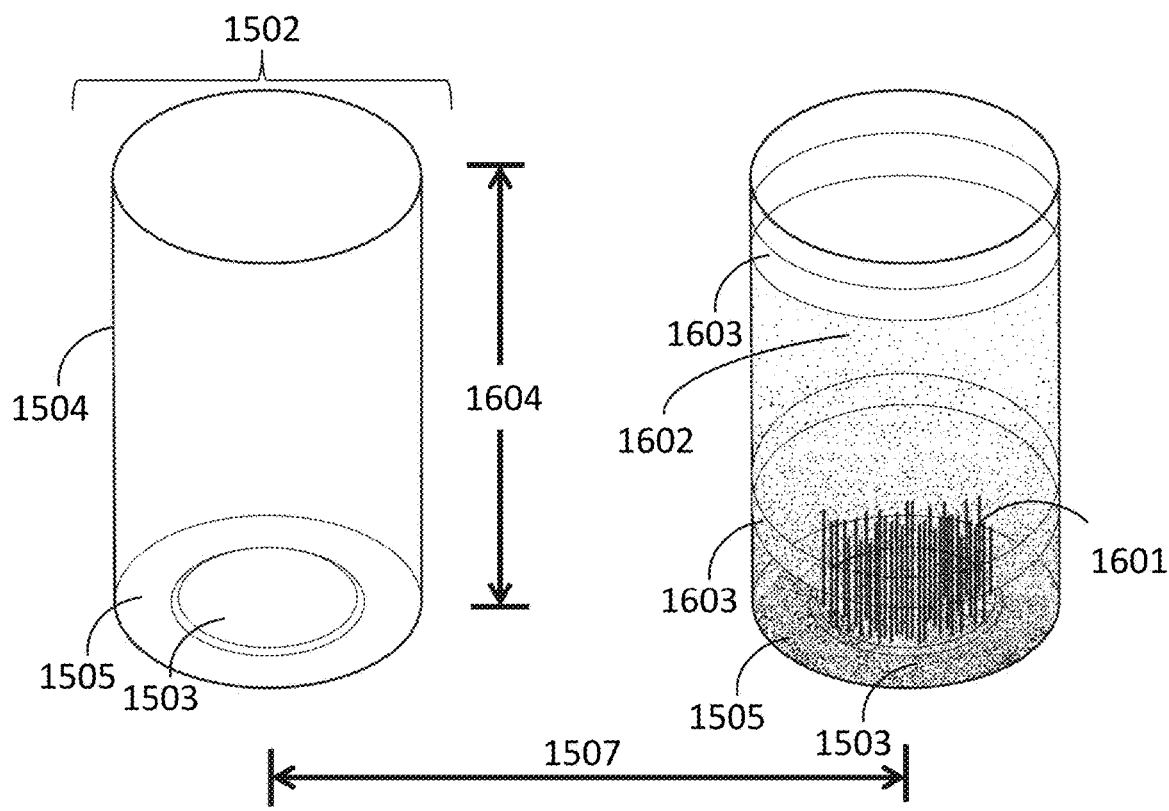
FIG. 16B depicts an array for synthesis using electrochemistry.

Described herein are devices comprising a solid support, wherein the solid support comprises a plurality of wells, wherein each of the wells comprises an addressable locus comprising: a synthesis surface located in a bottom region of each of the wells; and at least one sidewall electrode located on a sidewall of each of the wells, wherein the electrochemical generation of reagents is spatially separated from a polynucleotide attachment point to the synthesis surface. In some instances, devices described herein further comprise a bottom electrode in addressable communication with the synthesis surface. For example, sidewall electrodes 1603 can be used to control adhesion of substrates or reagents (See FIG. 16B). In some instances, reagents comprise protons or other acid molecule. In some instances, sidewall electrodes 1603 are located at positions around the edges of the well surface (See FIG. 16B) of a well having depth 1604. In some instances, sidewall electrodes control chemical reactions occurring near the synthesis surface. For example, if acid or other reagent is generated near the synthesis surface, the portion of a polynucleotide 1601 bound to this surface will be contacted with a higher concentration of acid than the portion of the polynucleotide that is distal to the site of acid generation. This may lead to degradation of the portion of the polynucleotide which is exposed to higher concentrations of acid. Sidewall electrodes 1603 in some instances produce or control a proton gradient 1602 which results in uniform or targeted exposure of a portion of the polynucleotide 1601 to acid. Sites near uncharged electrodes do not couple with nucleosides deposited over the synthesis surface, and the pattern of charged electrodes is altered before addition of the next nucleoside. By applying a series of electrode-controlled masks to the surface, the desired polynucleotides are synthesized at exact locations on the surface. Additionally, local control of coupling in some instances reduces synthetic steps, reduces reagents/materials (due to higher polynucleotide density and reduced scale), and reduces synthesis time (no movement of the synthesis surface). Wells in some instances comprise one, two, three, four, or more than four sidewall electrodes. In some instances, wells comprise two sidewall electrodes. In some instances, each sidewall electrode is independently addressable. For example, different voltages are independently applied to two or more different sidewall electrodes. Such arrangements in some instances facilitate diffusion of reagents or polynucleotides in a defined plane between the two sidewall electrodes. Such sidewall electrodes in some instances are ring-shaped or continuous around the circumference of the well cross-section. In some instances, sidewall electrodes are discontinuous, or only partially cover a portion of a sidewall surface. For example, a sidewall electrode is continuous over about 5%, 10% 15%, 30%, 50%, 75%, or about 90% of the circumference of the well cross-section. Such sidewall electrodes in some instances have a height about equal to the well height, or about 5%, 10% 15%, 30%, 50%, 75%, or about 90% of the well height. In some instances, application of different voltages independently to two or more discontinuous sidewall electrodes causes diffusion of reagents or polynucleotides in a horizontal plane. In some instances, application of different voltages independently to two or more discontinuous sidewall electrodes causes diffusion of reagents or polynucleotides in a vertical plane.

Polynucleotide synthesis generally requires repeated deposition and removal of liquids (fluidics) on the synthesis surface. Bulk movement of fluids is some instances results in fluid loss (wetting, volume of transport lines or reaction wells), which results in low efficiency of reagent usage and higher cycle times for moving fluids. An alternative to bulk fluidics during synthesis is the use of digital fluidics, wherein reagents or reaction vessels are packaged as discrete droplets. Droplets in some instances are mixed, moved (merged, reacted), split, stored, added, removed or analyzed in discrete volumes by manipulation through a surface comprising insulated (or semiconductor-coated) electrodes, or electrowetting. Electrowetting allows for local control of fluid-surface interaction; for example energizing an electrode near a droplet results in splitting of the droplet. In some instances, droplets as described herein comprise a small volume. For example, the volume of a droplet is up to 10, 20, 50, 75, 100, 125, 150, 200, 300, 500, 800, or more than 1000 femtoliters. In some instances, the volume of a droplet is about 50 to about 200 femtoliters. In some instances, digital fluidics results in at least a 2, 3, 4, 7, 10 or more than 10× decrease in cycle times relative to bulk fluidics. In some instances, digital fluidics results in about 2× to 10× decrease in cycle times relative to bulk fluidics. In some instances, the time to complete one cycle (sequential coupling of 4 bases, including washes) is about 1, 2, 3, 5, 7, 10, 12, 15, 17, 20, 30, 50, 100, or about 200 milliseconds (ms). In some instances, the time to complete one cycle is up to 1, 2, 3, 5, 7, 10, 12, 15, 17, 20, 30, 50, 100, or up to 200 ms. In some instances, the time to complete one cycle is about 10 to about 50 ms.

Movement of fluids in or out of surfaces described herein may comprise modifications or conditions that prevent unwanted fluid movement or other phenomenon. For example, fluid movement in some instances results in the formation of bubbles or pockets of gas, which limits contact of fluids with components such as surfaces or polynucleotides. Various methods to control or minimize bubble formation are contemplated by the methods, systems, and compositions described herein. Such methods include control of fluid pressure, well geometry, or surface materials/coatings. Well geometry can be implemented to minimize bubbles. For example, tapering the well, channels, or other surface can reduce or eliminate bubble formation during fluid flow. Surface materials possessing specific wetting properties can be implemented to reduce or eliminate bubble formation. For example, surfaces described herein comprise hydrophobic materials. In some instances, surfaces described herein comprise hydrophilic materials. Pressure can be used to control bubble formation during fluid movement. Pressure in some instances is applied locally to a component, an area of a surface, a capillary/channel, or applied to an entire system. Pressure is in some instances applied either behind the direction of fluid movement, or in front of it. In some instances, back pressure is applied to prevent the formation of bubbles. Suitable pressures used for preventing bubble formation can range depending on fluid, the scale, flow geometry, and the materials used. For example, 5 to 10 atmospheres of pressure are maintained in the system. In some instances, at least 2, 3, 4, 5, 6, 7, 8, 9, 10, 11, 12, 15, 20 or more than 50 atmospheres of pressure are applied. In some instances, up to 2, 3, 4, 5, 6, 7, 8, 9, 10, 11, 12, 15, 20 or up to 50 atmospheres of pressure are applied. In some instances, about 2 to about 10, about 2 to about 8, about 2 to about 5, about 4 to about 10, about 4 to about 12, about 5 to about 15, about 5 to about 7, about 7 to about 20, about 8 to about 15, or about 10 to about 20 atmospheres of pressure are applied.

Devices described herein may utilize control units for the purpose of regulating environmental conditions, such as temperature. Temperature control units are often used to prepare or maintain conditions for storing solid supports comprising polynucleotides. Storage conditions of nucleic acids can affect their long term stability, which directly influences the quality of the digital storage information that is retrieved. Polynucleotides are optionally stored at low temperature (for example, 10 degrees C., 4 degrees C., 0 degrees C., or lower) on a solid support, wherein a temperature control unit maintains this solid support temperature. The storage medium for polynucleotides on a solid support, such as solvated or dry also influences storage stability. In some instances, polynucleotides are stored in solution, such as an aqueous solution or buffer in droplets. In some instances, polynucleotides are stored lyophilized (dry). Temperature control units in some instances increase the chip temperature to facilitate drying of polynucleotides attached thereto. Temperature control units also provide for local control of heating at addressable locations on the solid support in some instances. In some instances, following addition of the droplets comprising the polynucleotides to the solid support, the solid support is dried. In some instances, the dried solid support is later resolvated. In some instances, the solid support is stored for later use. In some instances, the solid support further comprises an index map of the polynucleotides. In some instances, the solid support further comprises metadata.

Devices described herein can comprise power sources used to energize various components of the device. Synthesis components in the solid support are optionally powered by an external power source, or a power source integrated into the solid support. Power sources may comprise batteries, solar cells, thermoelectric generators, inductive (wireless) power units, kinetic energy charger, cellular telephones, tablets, or other power source suitable for use with the synthesis components or devices described herein. In some instances, synthesis components, surfaces, or devices described herein are portable.

Fluids comprising reagents, wash solvents, or other synthesis components are deposited on the synthesis surface. Unused fluid (prior to contact with the synthesis surface) or waste fluid (after contact with the synthesis surface) is in some instances stored in one or more compartments integrated into the solid support. Alternately or in combination, polynucleotides are moved in or out of the solid support for external analysis or storage. For example, synthesized polynucleotides are cleaved from loci on the solid support in a droplet, the resulting droplet moved externally to the synthesis area of the solid support. The droplet is optionally dried for storage. In some instances, fluids are stored externally from the solid support. In some instances, a device described herein comprises a solid support with a plurality of fluidics ports which allow movement of fluids in and out of the solid support. In some instances, ports are oriented on the sides of the solid support, by other configurations are also suitable for delivery of fluids to the synthesis surface. Such a device often comprises, for example, at least 1, 2, 5, 10, 20, 50, 100, 200, 500, 1000, 2000, 5000, or at least 10,000 ports per mm length of a solid support. In some instances, a device described herein comprises about 100 to about 5000 ports per mm per length of a solid support.

Described herein are addressable electrodes integrated into a solid support. Electrodes comprise without limitation conductors, insulators, or semi-conductors, and are fabricated of materials well known in the art. Materials may comprise metals, non-metals, mixed-metal oxides, nitrides, carbides, silicon-based materials, or other material. In some instances, metal oxides include $TiO_2$, $Ta_2O_5$, $Nb_2O_5$, $Al_2O_3$, BaO, $Y_2O_3$, $HfO_2$, SrO or other metal oxide known in the art. In some instances, metal carbides include TiC, WC, $ThC_2$, ThC, VC, $W_2C$, ZrC, HfC, NbC, TaC, $Ta_2C$, or other metal carbide known in the art. In some instances, metal nitrides include GaN, InN, BN, $Be_3N_2$, $Cr_2N$, MoN, $Si_3N_4$, TaN, $Th_2N_2$, VN, ZrN, TiN, HfN, NbC, WN, TaN, or other metal nitride known in the art. In some instances, a device disclosed herein is manufactured with a combination of materials listed herein or any other suitable material known in the art. Electrodes can possess any shape, including discs, rods, wells, posts, a substantially planar shape, or any other form suited for nucleic acid synthesis. The or cross-sectional area of each electrode varies as a function of the size of the loci for polynucleotide synthesis, but in some instances is up to 500 um$^2$, 200 um$^2$, 100 um$^2$, 75 um$^2$, 50 um$^2$, 25 um$^2$, 10 um$^2$, less than 5 um$^2$. In some instances, the cross-sectional area of each electrode is about 500 um$^2$ to 10 um$^2$, about 100 um$^2$ to 25 um$^2$, or about 150 um$^2$ to 50 um$^2$. In some instances, the cross-sectional area of each electrode is about 150 um$^2$ to 50 um$^2$. Devices provide herein include electrodes having a diameter that varies as a function of the size of the loci for polynucleotide synthesis. Exemplary electrode diameters include, without limitation, up to 500 um, 200 um, 100 um, 75 um, 50 um, 25 um, 10 um, less than 5 um. In some instances, the diameter of each electrode is about 500 um to 10 um, about 100 um to 25 um, about 100 um to about 200 um, about 50 um to about 200 um, or about 150 um to 50 um. In some instances, the diameter of each electrode is about 200 um to 50 um. In some instances, the diameter of each electrode is about 200 um to 100 um. In some instances, the diameter of each electrode is up to 500 nm, 200 nm, 100 nm, 75 nm, 50 nm, 25 nm, 10 nm, less than 5 nm. In some instances, the diameter of each electrode is about 500 nm to 10 nm, about 100 nm to 25 nm, about 100 nm to about 200 nm, about 50 nm to about 200 nm, or about 150 nm to 50 nm. In some instances, the diameter of each electrode is about 200 nm to 50 nm. In some instances, the diameter of each electrode is about 200 nm to 100 nm. The thickness of each electrode varies as a function of the size of the loci for polynucleotide synthesis, but in some instances is about 50 nm, 100 nm, 200 nm, 500 nm, 750 nm, 1000 nm, 1200 nm, 1500 nm, 2000 nm, 2500 nm, 3000 nm, or about 3500 nm. In some instances the thickness of the electrode is at least 50 nm, 100 nm, 200 nm, 500 nm, 750 nm, 1000 nm, 1200 nm, 1500 nm, 2000 nm, 2500 nm, 3000 nm, or at least 3500 nm. In some instances the thickness of the electrode is at least 1 um, 2 um, 3 um, 5 um, 10 um, 15 um, 20 um, 30 um, 50 um or at least 75 um. In some instances the thickness of the electrode is about 1 um, 2 um, 3 um, 5 um, 10 um, 15 um, 20 um, 30 um, 50 um or about 75 um. In some instances the thickness of the electrode is up to 1 um, 2 um, 3 um, 5 um, 10 um, 15 um, 20 um, 30 um, 50 um or up to 75 um. In some instances the thickness of the electrode is up to 50 nm, 100 nm, 200 nm, 500 nm, 750 nm, 1000 nm, 1200 nm, 1500 nm, 2000 nm, 2500 nm, 3000 nm, or up to 3500 nm. In some instances the thickness of the electrode is about 20 nm to 3000 nm, about 50 nm to 2500, about 100 nm to 750 nm, about 400 nm to 750 nm, about 500 nm to 3000 nm, or about 1000 nm to 3000 nm. In some instances the thickness of the electrode is about 10 um to about 20 um. In some instances the thickness of the electrode is about 5 um to about 50 um, about 10 um to about 30 um, about 15 um to about 25 um, or about 30 um to about 50 um. In some instances, electrodes are coated with additional materials such as semiconductors or insulators. In some instances, electrodes are coated with materials for polynucleotide attachment and synthesis. The size, shape, pattern, or orientation of electrodes is in some instances chosen to minimize deleterious side reactions caused by electrochemically generated reagents. In some instances combinations of electrodes are used, such as a grid of addressable electrodes and a common electrode. Electrodes are in some instances cathodes or anodes. Electrodes or arrays of electrodes can be positioned anywhere on or near the polynucleotide surface. In some instances, electrodes are placed on the bottom of loci for synthesis, such as the bottom of a well or channel. In some instances, electrodes are placed in the sidewalls of a well or channel ("sidewall electrodes"). A plurality of sidewall electrodes are in some instances present on the sides of a well. Electrodes positioned at different locations in the device can have different functions, and are independently or simultaneously addressable. In some instances, an electrode in the bottom of a well is used to cleave polynucleotides from the surface at one or more loci, and a sidewall electrode is used to generate acid to deprotect polynucleotides. In some instances, an electrode in the bottom of a well is used to cleave polynucleotides from the surface at one or more loci, and a first sidewall electrode is used to generate acid to deprotect polynucleotides, and a second sidewall electrode is used to move polynucleotides out of the well after cleavage. In exemplary configurations, sidewall electrodes are located about 10 nm, about 25 nm, about 50 nm, about 75 nm, about 100 nm, about 125 nm, or about 200 nm above the synthesis surface. In some instances, sidewall electrodes are located about 10 nm to about 100 nm, about 50 nm to about 150 nm, about 40 nm to 100 nm, about 75 nm to about 125 nm, about 100 to 300 nm above the synthesis surface. In some instances, multiple sidewall electrodes are located at different heights above the synthesis surface. For example, a locus comprises at least one sidewall electrode, at least 2 sidewall electrodes, at least 3 sidewall electrodes, or more than 3 sidewall electrodes. In exemplary configurations, sidewall electrodes have a height of about 1 nm, about 5 nm, about 10 nm, about 20 nm, about 25 nm about 30 nm, about 40 nm, or about 50 nm. In some instances, sidewall electrodes have a height of 1 nm to 20 nm, 2 nm to 30 nm, 5 nm to 20 nm, 10 nm to 40 nm, or 5 nm to 25 nm.

Electrode surfaces can support the movement, conformation, synthesis, growth, and release of polynucleotides. In some instances, electrodes are coated with one or more layers. In some instances, the layer is a monolayer which facilities attachment of a linker. In some instances, the electrode is charged to influence the area of the monolayer to be functionalized with a linker. This allows for masking of specific areas for chemical functionalization, such as modifying the surface with hydrophobic or hydrophilic chemical groups. In some instances, the electrode is charged to influence the area of the monolayer to be extended with a nucleoside monomer. This in some instances includes generation of reagents to facilitate or prevent coupling of monomers to synthesis surfaces in the vicinity of an electrode. In some instances, the electrode is charged to influence the area of the monolayer which releases polynucleotides. Such controlled release of specific polynucleotides in a specific order in some instances is used to control the assembly of synthesized monomers into larger polynucleotides. For example, an iterative polynucleotide assembly process is optimized by exploring which various combinations of polynucleotides that are released and allowed to hybridize for overlap PCR assembly.

Each electrode can control one, or a plurality of different loci for synthesis, wherein each locus for synthesis has a density of polynucleotides. In some instances, the density is at least 1 oligo per 10 $nm^2$, 20, 50, 100, 200, 500, 1,000, 2,000, 5,000 or at least 1 oligo per 10,000 $nm^2$. In some instances, the density is about 1 oligo per 10 $nm^2$ to about 1 oligo per 5,000 $nm^2$, about 1 oligo per 50 $nm^2$ to about 1 oligo per 500 $nm^2$, or about 1 oligo per 25 $nm^2$ to about 1 oligo per 75 $nm^2$. In some instances, the density of polynucleotides is about 1 oligo per 25 $nm^2$ to about 1 oligo per 75 $nm^2$.

Provided herein are devices for polynucleotide synthesis having various types of electrodes. In some instances, the device comprises a reference electrode. Reference electrodes are placed near the synthesis surface or in the case of a well or channel, for example, above a well or channel. In some instances, a reference electrode is about 1 to about 50 um above the synthesis surface, about 2 um to about 40 um, about 3 um to about 30 um, about 5 um to about 20 um, about 10 to about 20 um, about 15 um to about 50 um, about 30 to about 50 um, about 5 um to about 30 um or about 7 um to about 25 um. In some instances a reference electrode is about 1, 2, 5, 7, 8, 9, 10, 12, 14, 16, 18, 20, 22, 24, 26 um or more than 26 um above the synthesis surface. In some instances a reference electrode is up to 1, 2, 5, 7, 8, 9, 10, 12, 14, 16, 18, 20, 22, 24, 26 um or up to 26 um above the synthesis surface. In some instances a reference electrode is at least 1, 2, 5, 7, 8, 9, 10, 12, 14, 16, 18, 20, 22, 24, 26 um or at least 26 um above the synthesis surface. Reference electrodes in some instances are adjacent to synthesis surfaces, such as adjacent to a well or channel. Each locus in some instances has one corresponding reference electrode. In some instances, each locus shares a common reference electrode with one or more adjacent loci. The devices described herein may comprise any number of reference electrodes. In some instances the reference electrode is a single, uniform plate. In some instances, devices comprise a plurality of reference electrodes. A reference electrode can address a plurality of loci, for example 2, 3, 4, 5, 10 or more loci.

Described herein are devices, compositions, systems and methods for solid support based nucleic acid synthesis and storage, wherein the solid support has varying dimensions. In some instances, a size of the solid support is between about 40 and 120 mm by between about 25 and 100 mm. In some instances, a size of the solid support is about 80 mm by about 50 mm. In some instances, a width of a solid support is at least or about 10 mm, 20 mm, 40 mm, 60 mm, 80 mm, 100 mm, 150 mm, 200 mm, 300 mm, 400 mm, 500 mm, or more than 500 mm. In some instances, a height of a solid support is at least or about 10 mm, 20 mm, 40 mm, 60 mm, 80 mm, 100 mm, 150 mm, 200 mm, 300 mm, 400 mm, 500 mm, or more than 500 mm. In some instances, the solid support has a planar surface area of at least or about 100 mm$^2$; 200 mm$^2$; 500 mm$^2$; 1,000 mm$^2$; 2,000 mm$^2$; 4,500 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some instances, the thickness of the solid support is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples thickness of the solid support include 275 mm, 375 mm, 525 mm, 625 mm, 675 mm, 725 mm, 775 mm and 925 mm. In some instances, the thickness of the solid support is at least or about 0.5 mm, 1.0 mm, 1.5 mm, 2.0 mm, 2.5 mm, 3.0 mm, 3.5 mm, 4.0 mm, or more than 4.0 mm.

Figure 14:
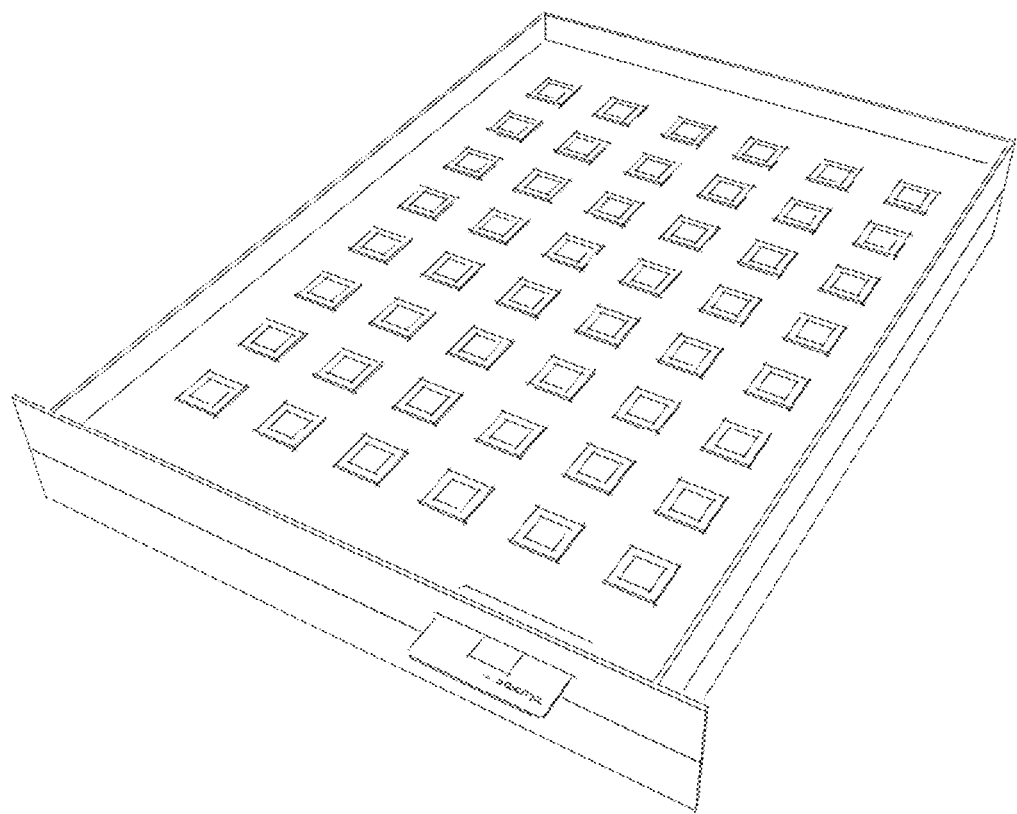
FIG. 14 is an example of rack-style instrument.

Described herein are devices wherein two or more solid supports are assembled. In some instances, solid supports are interfaced together on a larger unit. Interfacing may comprise exchange of fluids, electrical signals, or other medium of exchange between solid supports. This unit is capable of interface with any number of servers, computers, or networked devices. For example, a plurality of solid support is integrated onto a rack unit, which is conveniently inserted or removed from a server rack. The rack unit may comprise any number of solid supports. In some instances the rack unit comprises at least 1, 2, 5, 10, 20, 50, 100, 200, 500, 1000, 2000, 5000, 10,000, 20,000, 50,000, 100,000 or more than 100,000 solid supports. In some instances, two or more solid supports are not interfaced with each other. Nucleic acids (and the information stored in them) present on solid supports can be accessed from the rack unit. See e.g., FIG. 14. Access includes removal of polynucleotides from solid supports, direct analysis of polynucleotides on the solid support, or any other method which allows the information stored in the nucleic acids to be manipulated or identified. Information in some instances is accessed from a plurality of racks, a single rack, a single solid support in a rack, a portion of the solid support, or a single locus on a solid support. In various instances, access comprises interfacing nucleic acids with additional devices such as mass spectrometers, HPLC, sequencing instruments, PCR thermocyclers, or other device for manipulating nucleic acids. Access to nucleic acid information in some instances is achieved by cleavage of polynucleotides from all or a portion of a solid support. Cleavage in some instances comprises exposure to chemical reagents (ammonia or other reagent), electrical potential, radiation, heat, light, acoustics, or other form of energy capable of manipulating chemical bonds. In some instances, cleavage occurs by charging one or more electrodes in the vicinity of the polynucleotides. In some instances, electromagnetic radiation in the form of UV light is used for cleavage of polynucleotides. In some instances, a lamp is used for cleavage of polynucleotides, and a mask mediates exposure locations of the UV light to the surface. In some instances, a laser is used for cleavage of polynucleotides, and a shutter opened/closed state controls exposure of the UV light to the surface. In some instances, access to nucleic acid information (including removal/addition of racks, solid supports, reagents, nucleic acids, or other component) is completely automated.

Solid supports as described herein comprise an active area. In some instances, the active area comprises addressable regions or loci for nucleic acid synthesis. In some instances, the active area comprises addressable regions or loci for nucleic acid storage.

Figure 13:
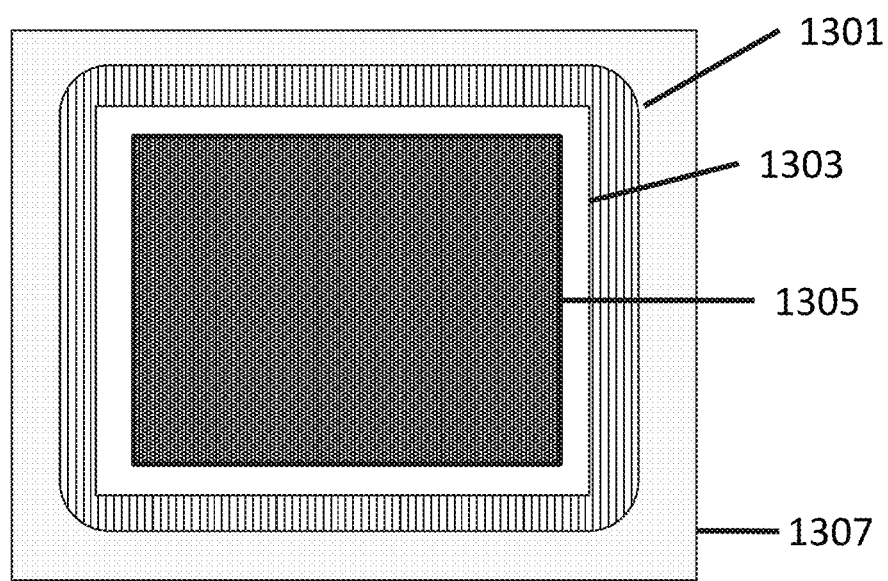
FIG. 13 is a schema of solid support comprising an active area and fluidics interface.

The active area comprises varying dimensions. For example, the dimension of the active area is between about 1 mm to about 50 mm by about 1 mm to about 50 mm. In some instances, the active area comprises a width of at least or about 0.5, 1, 1.5, 2, 2.5, 3, 5, 5, 10, 12, 14, 16, 18, 20, 25, 30, 35, 40, 45, 50, 60, 70, 80, or more than 80 mm. In some instances, the active area comprises a height of at least or about 0.5, 1, 1.5, 2, 2.5, 3, 5, 5, 10, 12, 14, 16, 18, 20, 25, 30, 35, 40, 45, 50, 60, 70, 80, or more than 80 mm. An exemplary active area within a solid support is seen in FIG. 13. A package 1307 comprises an active area 1305 within a solid support 1303. The package 1307 also comprises a fluidics interface 1301.

Described herein are devices, compositions, systems and methods for solid support based nucleic acid synthesis and storage, wherein the solid support has a number of sites (e.g., spots) or positions for synthesis or storage. In some instances, the solid support comprises up to or about 10,000 by 10,000 positions in an area. In some instances, the solid support comprises between about 1000 and 20,000 by between about 1000 and 20,000 positions in an area. In some instances, the solid support comprises at least or about 10, 30, 50, 75, 100, 200, 300, 400, 500, 1000, 2000, 3000, 4000, 5000, 6000, 7000, 8000, 9000, 10,000, 12,000, 14,000, 16,000, 18,000, 20,000 positions by least or about 10, 30, 50, 75, 100, 200, 300, 400, 500, 1000, 2000, 3000, 4000, 5000, 6000, 7000, 8000, 9000, 10,000, 12,000, 14,000, 16,000, 18,000, 20,000 positions in an area. In some instances the area is up to 0.25, 0.5, 0.75, 1.0, 1.25, 1.5, or 2.0 inches squared. In some instances, the solid support comprises addressable loci having a pitch of at least or about 0.1, 0.2, 0.25, 0.3, 0.4, 0.5, 1.0, 1.5, 2.0, 2.5, 3.0, 3.5, 4.0, 4.5, 5, 6, 7, 8, 9, 10, or more than 10 um. In some instances, the solid support comprises addressable loci having a pitch of about 5 um. In some instances, the solid support comprises addressable loci having a pitch of about 2 um. In some instances, the solid support comprises addressable loci having a pitch of about 1 um. In some instances, the solid support comprises addressable loci having a pitch of about 0.2 um. In some instances, the solid support comprises addressable loci having a pitch of about 0.2 um to about 10 um, about 0.2 to about 8 um, about 0.5 to about 10 um, about 1 um to about 10 um, about 2 um to about 8 um, about 3 um to about 5 um, about 1 um to about 3 um or about 0.5 um to about 3 um. In some instances, the solid support comprises addressable loci having a pitch of about 0.1 um to about 3 um. See e.g. FIG. 15, FIG. 16A, and FIG. 16B.

The solid support for nucleic acid synthesis or storage as described herein comprises a high capacity for storage of data. For example, the capacity of the solid support is at least or about 1, 2, 3, 4, 5, 6, 7, 8, 9, 10, 20, 50, 100, 200, 300, 400, 500, 600, 700, 800, 900, 1000, or more than 1000 petabytes. In some instances, the capacity of the solid support is between about 1 to about 10 petabytes or between about 1 to about 100 petabytes. In some instances, the capacity of the solid support is about 100 petabytes. In some instances, the data is stored as addressable arrays of packets as droplets. In some instances, the data is stored as addressable arrays of packets as droplets on a spot. In some instances, the data is stored as addressable arrays of packets as dry wells. In some instances, the addressable arrays comprise at least or about 1, 2, 3, 4, 5, 6, 7, 8, 9, 10, 20, 50, 100, 200, or more than 200 gigabytes of data. In some instances, the addressable arrays comprise at least or about 1, 2, 3, 4, 5, 6, 7, 8, 9, 10, 20, 50, 100, 200, or more than 200 terabytes of data. In some instances, an item of information is stored in a background of data. For example, an item of information encodes for about 10 to about 100 megabytes of data and is stored in 1 petabyte of background data. In some instances, an item of information encodes for at least or about 1, 10, 20, 30, 40, 50, 60, 70, 80, 90, 100, 150, 200, 300, 400, 500, or more than 500 megabytes of data and is stored in 1, 10, 20, 30, 40, 50, 60, 70, 80, 90, 100, 150, 200, 300, 400, 500, or more than 500 petabytes of background data.

Provided herein are devices, compositions, systems and methods for solid support based nucleic acid synthesis and storage, wherein following synthesis, the polynucleotides are collected in packets as one or more droplets. In some instances, the polynucleotides are collected in packets as one or more droplets and stored. In some instances, a number of droplets is at least or about 1, 10, 20, 50, 100, 200, 300, 500, 1000, 2500, 5000, 75000, 10,000, 25,000, 50,000, 75,000, 100,000, 1 million, 5 million, 10 million, 25 million, 50 million, 75 million, 100 million, 250 million, 500 million, 750 million, or more than 750 million droplets. In some instances, a droplet volume comprises 5, 10, 15, 20, 25, 30, 35, 40, 45, 50, 55, 60, 65, 70, 75, 80, 85, 90, 95, 100, or more than 100 um (micrometer) in diameter. In some instances, a droplet volume comprises 1-100 um, 10-90 um, 20-80 um, 30-70 um, or 40-50 um in diameter.

In some instances, the polynucleotides that are collected in the packets comprise a similar sequence. In some instances, the polynucleotides further comprise a non-identical sequence to be used as a tag or barcode. For example, the non-identical sequence is used to index the polynucleotides stored on the solid support and to later search for specific polynucleotides based on the non-identical sequence. Exemplary tag or barcode lengths include barcode sequences comprising, without limitation, about 1, 2, 3, 4, 5, 6, 7, 8, 9, 10, 15, 20, 25 or more bases in length. In some instances, the tag or barcode comprise at least or about 10, 50, 75, 100, 200, 300, 400, or more than 400 base pairs in length.

Provided herein are devices, compositions, systems and methods for solid support based nucleic acid synthesis and storage, wherein the polynucleotides are collected in packets comprising redundancy. For example, the packets comprise about 100 to about 1000 copies of each polynucleotide. In some instances, the packets comprise at least or about 50, 75, 100, 200, 300, 400, 500, 600, 700, 800, 900, 1000, 1200, 1400, 1600, 1800, 2000, or more than 2000 copies of each polynucleotide. In some instances, the packets comprise about 1000× to about 5000× synthesis redundancy. Synthesis redundancy in some instances is at least or about 500×, 1000×, 1500×, 2000×, 2500×, 3000×, 3500×, 4000×, 5000×, 6000×, 7000×, 8000×, or more than 8000×. The polynucleotides that are synthesized using solid support based methods as described herein comprise various lengths. In some instances, the polynucleotides are synthesized and further stored on the solid support. In some instances, the polynucleotide length is in between about 100 to about 1000 bases. In some instances, the polynucleotides comprise at least or about 10, 20, 30, 40, 50, 60, 70, 80, 90, 100, 125, 150, 175, 200, 225, 250, 275, 300, 325, 350, 375, 400, 425, 450, 475, 500, 600, 700, 800, 900, 1000, 1100, 1200, 1300, 1400, 1500, 1600, 1700, 1800, 1900, 2000, or more than 2000 bases in length.

Nucleic Acid Based Information Storage

Provided herein are devices, compositions, systems and methods for nucleic acid-based information (data) storage. An exemplary workflow is provided in FIG. 1. In a first step, a digital sequence encoding an item of information (i.e., digital information in a binary code for processing by a computer) is received 101. An encryption 103 scheme is applied to convert the digital sequence from a binary code to a nucleic acid sequence 105. A surface material for nucleic acid extension, a design for loci for nucleic acid extension (aka, arrangement spots), and reagents for nucleic acid synthesis are selected 107. The surface of a structure is prepared for nucleic acid synthesis 108. De novo polynucleotide synthesis is performed 109. The synthesized polynucleotides are stored 111 and available for subsequent release 113, in whole or in part. Once released, the polynucleotides, in whole or in part, are sequenced 115, subject to decryption 117 to convert nucleic sequence back to digital sequence. The digital sequence is then assembled 119 to obtain an alignment encoding for the original item of information.

Items of Information

Optionally, an early step of data storage process disclosed herein includes obtaining or receiving one or more items of information in the form of an initial code. Items of information include, without limitation, text, audio and visual information. Exemplary sources for items of information include, without limitation, books, periodicals, electronic databases, medical records, letters, forms, voice recordings, animal recordings, biological profiles, broadcasts, films, short videos, emails, bookkeeping phone logs, internet activity logs, drawings, paintings, prints, photographs, pixelated graphics, and software code. Exemplary biological profile sources for items of information include, without limitation, gene libraries, genomes, gene expression data, and protein activity data. Exemplary formats for items of information include, without limitation, .txt, .PDF, .doc, .docx, .ppt, .pptx, .xls, .xlsx, .rtf, .jpg, .gif, .psd, .bmp, .tiff, .png, and .mpeg. The amount of individual file sizes encoding for an item of information, or a plurality of files encoding for items of information, in digital format include, without limitation, up to 1024 bytes (equal to 1 KB), 1024 KB (equal to 1 MB), 1024 MB (equal to 1 GB), 1024 GB (equal to 1 TB), 1024 TB (equal to 1 PB), 1 exabyte, 1 zettabyte, 1 yottabyte, 1 xenottabyte or more. In some instances, an amount of digital information is at least 1 gigabyte (GB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 gigabytes. In some instances, the amount of digital information is at least 1 terabyte (TB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 terabytes. In some instances, the amount of digital information is at least 1 petabyte (PB). In some instances, the amount of digital information is at least 1, 2, 3, 4, 5, 6, 7, 8, 9, 10, 20, 50, 100, 200, 300, 400, 500, 600, 700, 800, 900, 1000 or more than 1000 petabytes.

Structures for Polynucleotide Synthesis

Figure 2:
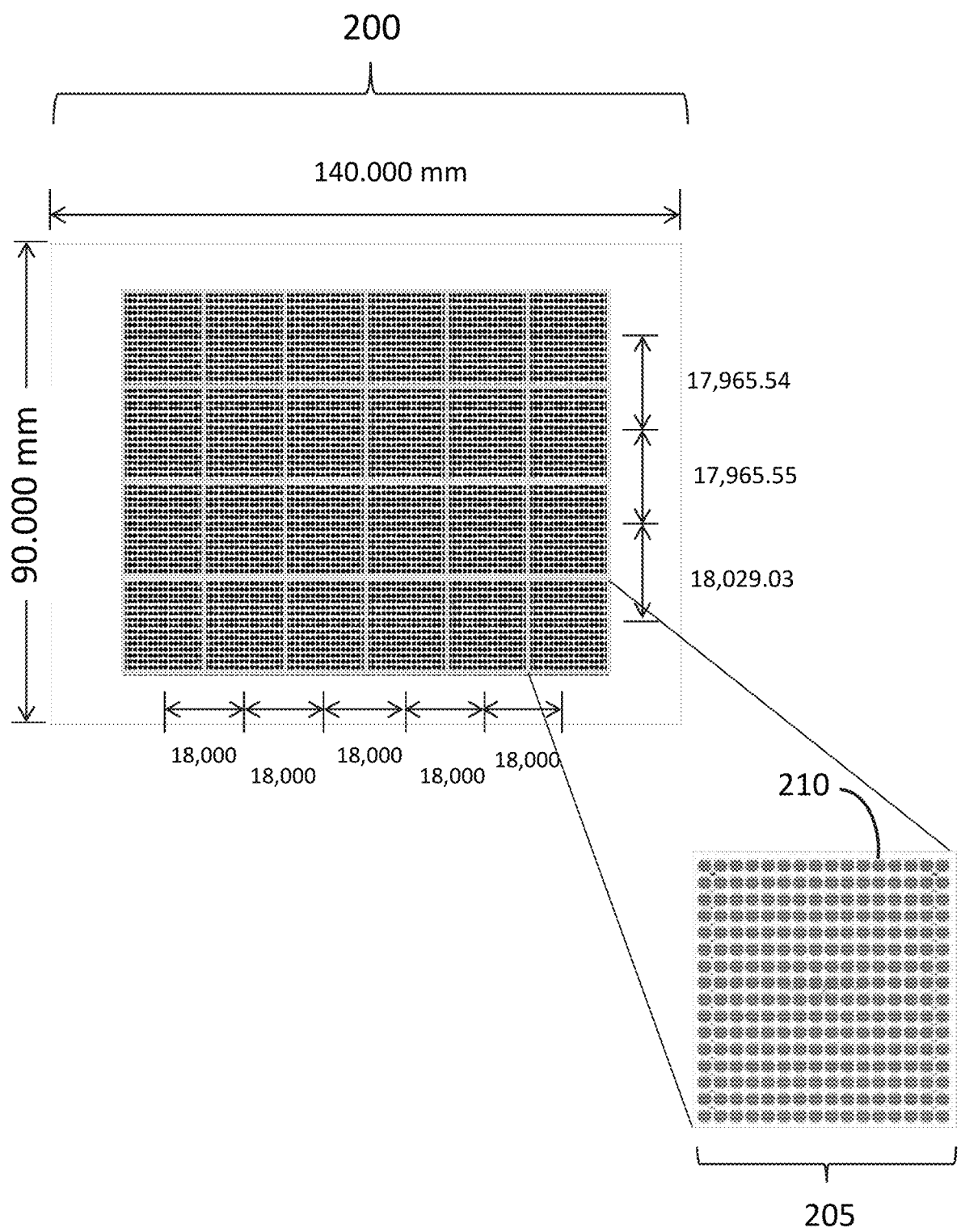
FIG. 2 illustrates a plate configured for polynucleotide synthesis comprising 24 regions, or sub-fields, each having an array of 256 clusters.
Figure 3:
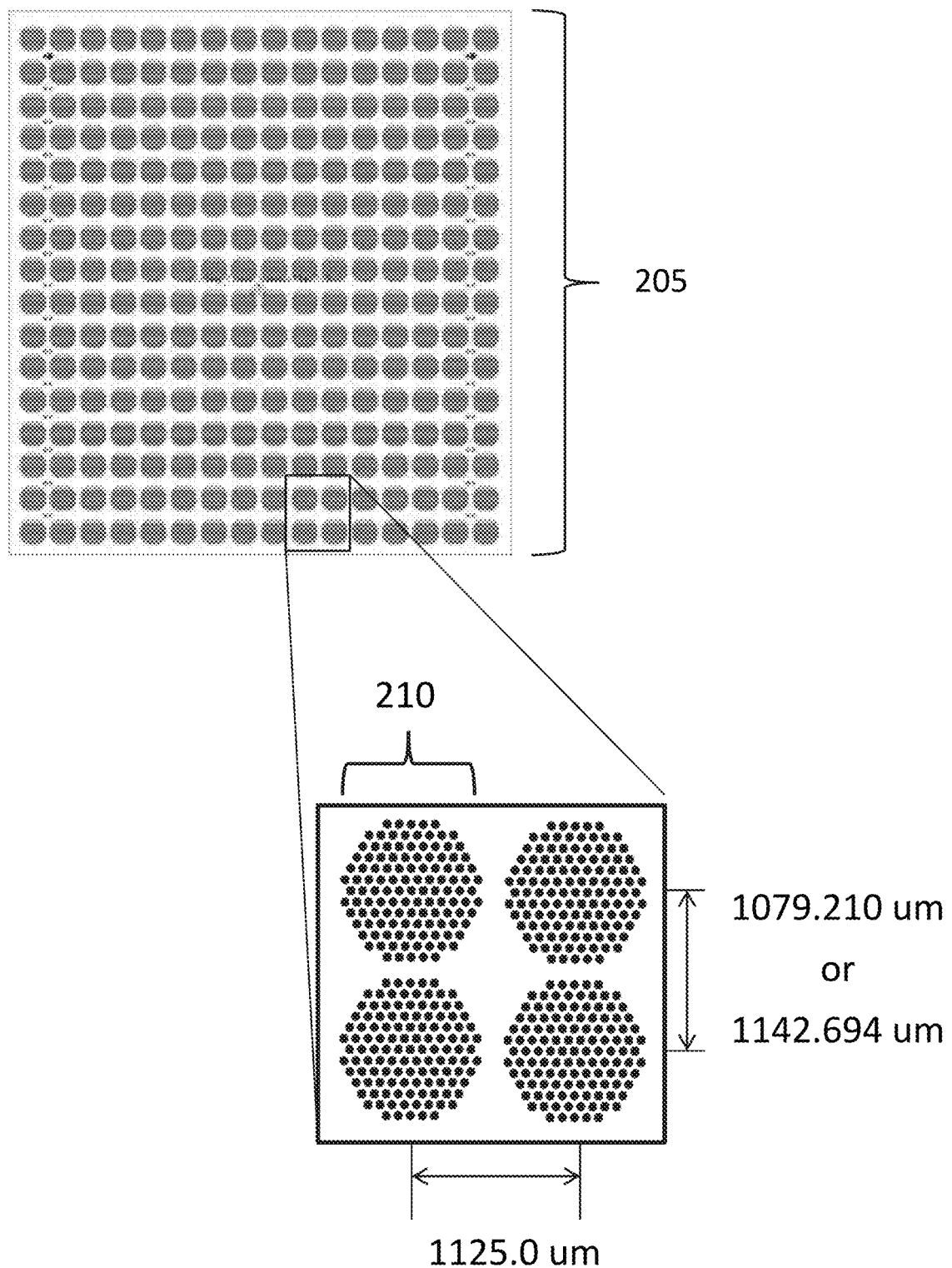
FIG. 3 illustrates a closer view of the sub-field in FIG. 2 having 16×16 of clusters, each cluster having 121 individual loci.
Figure 4:
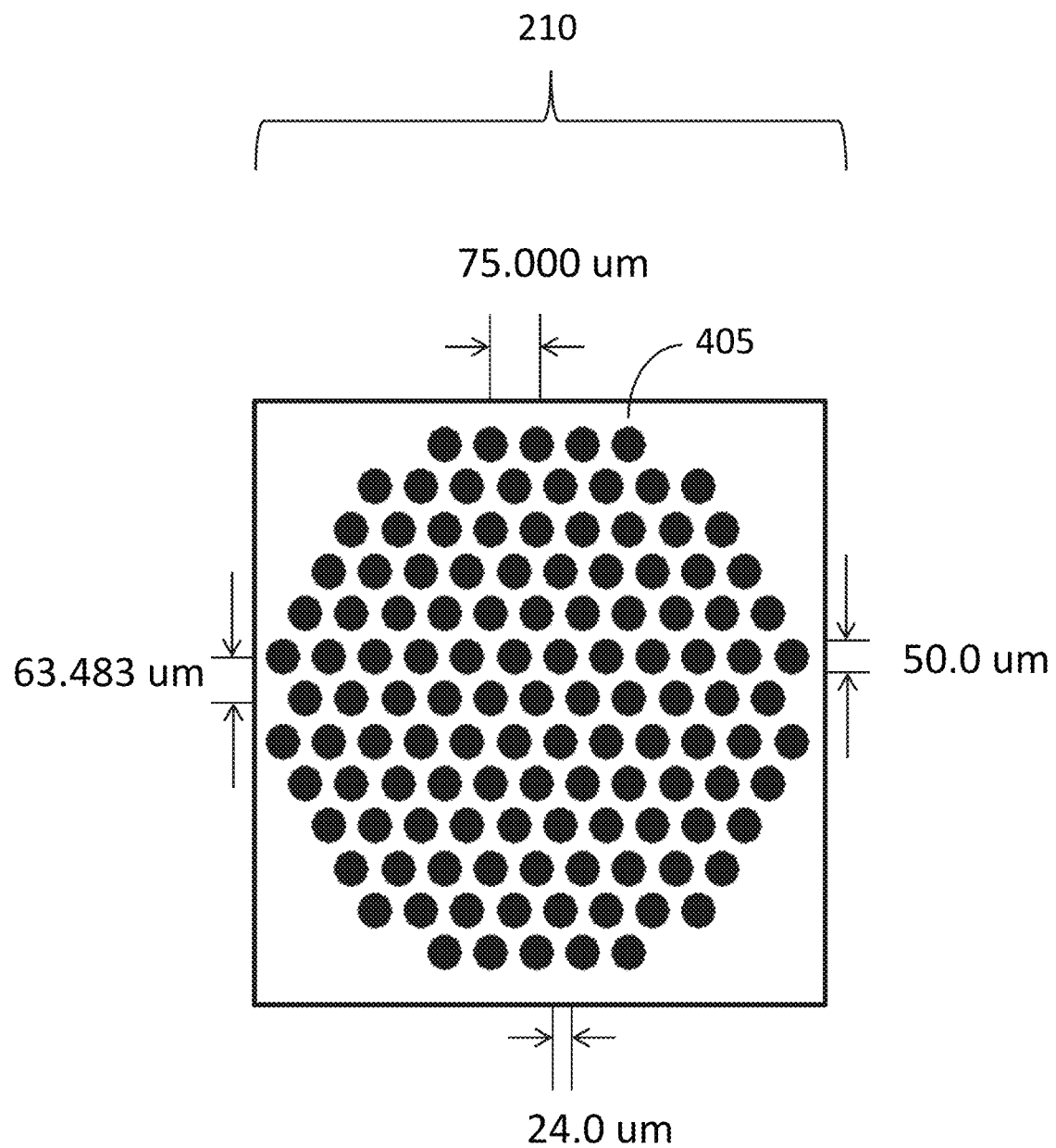
FIG. 4 illustrates a detailed view of the cluster in FIG. 2, where the cluster has 121 loci.
Figure 5A:
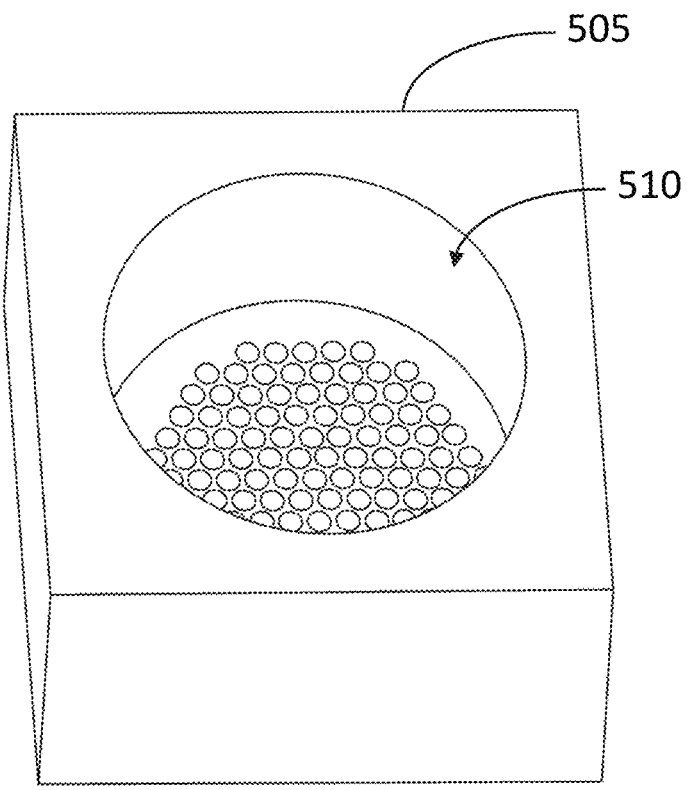
FIG. 5A illustrates a front view of a plate with a plurality of channels.
Figure 5B:
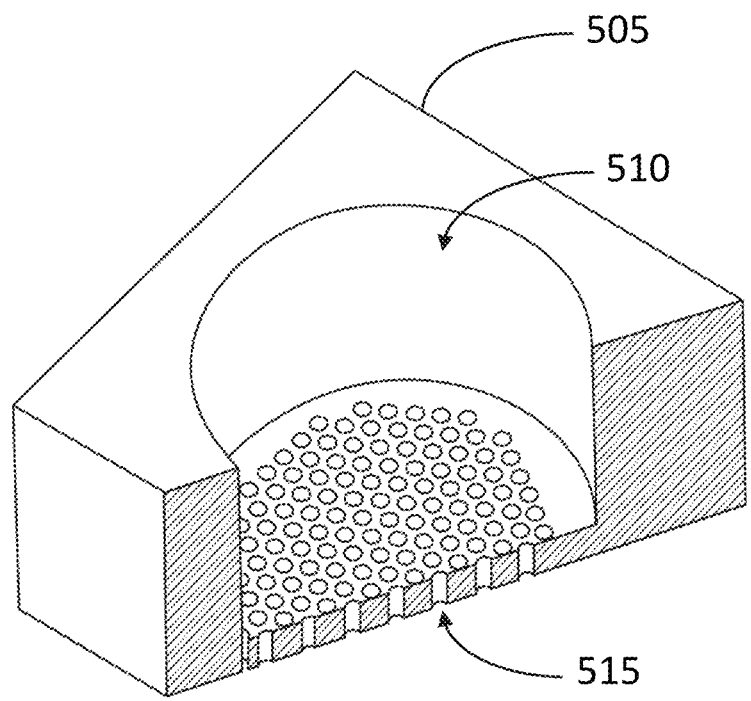
FIG. 5B illustrates a sectional view of plate with a plurality of channels.

Provided herein are rigid or flexibles structures for polynucleotide synthesis. In the case of rigid structures, provided herein are devices having a structure for the generation of a library of polynucleotides. In some instances, the structure comprises a plate. An exemplary structure 200 is illustrated in FIG. 2, wherein the structure 200 has about the same size dimensions as a standard 96 well plate: 140 mm by 90 mm. The structure 200 comprises clusters grouped in 24 regions or sub-fields 205, each sub-field 205 comprising an array of 256 clusters 210. An expanded view of an exemplary sub-field 205 is shown in FIG. 3. In the expanded view of four clusters (FIG. 3), a single cluster 210, has a Y axis cluster pitch (distance from center to center of adjacent clusters) of 1079.210 um or 1142.694 um, and an X axis cluster pitch of 1125 um. An illustrative cluster 210 is depicted in FIG. 4, where the Y axis loci pitch (distance from center to center of adjacent loci) is 63.483 um, and an X axis loci pitch is 75 um. The locus width at the longest part, e.g., diameter for a circular locus, is 50 um and the distance between loci is 24 um. The number of loci 405 in the exemplary cluster in FIG. 4 is 121. The loci may be flat, wells, or channels. An exemplary channel arrangement is illustrated in FIGS. 5A-5B where a plate 505 is illustrated comprising a main channel 510 and a plurality of channels 515 connected to the main channel 510. The connection between the main channel 510 and the plurality of channels 515 provides for a fluid communication for flow paths from the main channel 510 to the each of the plurality of channels 515. A plate 505 described herein can comprise multiple main channels 510. The plurality of channels 515 collectively forms a cluster within the main channel 510.

Figure 6A:
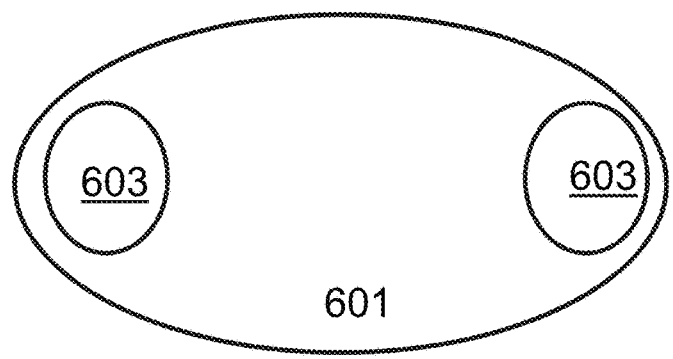
FIGS. 6A-6B depict a continuous loop and reel-to-reel arrangements for flexible structures.
Figure 6B:
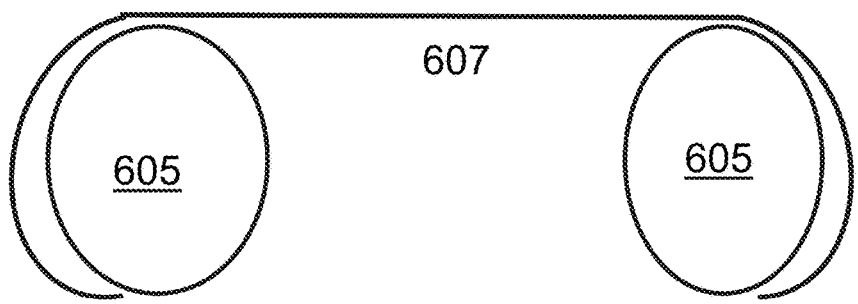
Figure 6C:
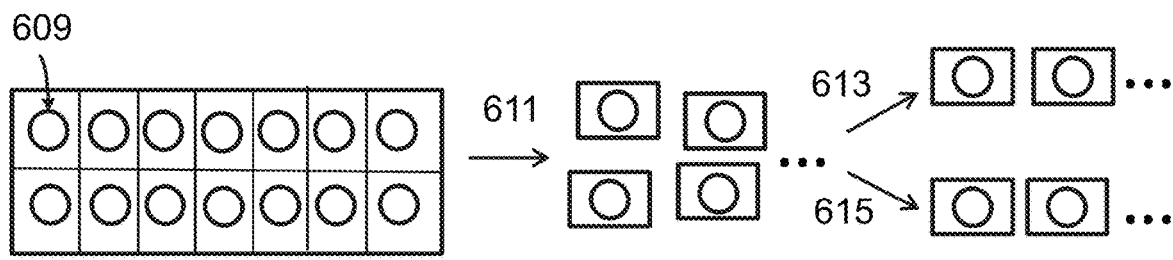
FIGS. 6C-6D depict schemas for release and extraction of synthesized polynucleotides.
Figure 6D:
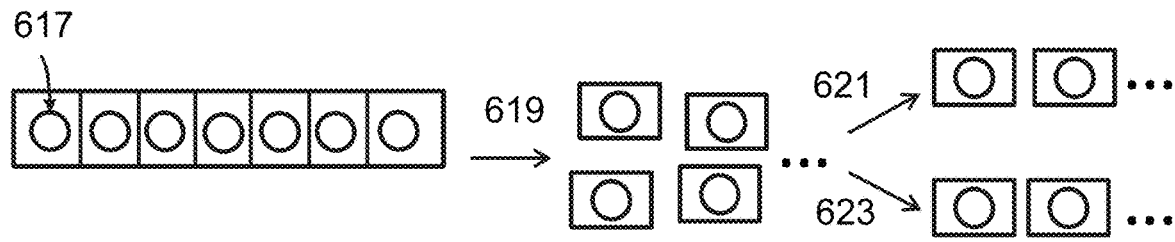
Figure 7A:
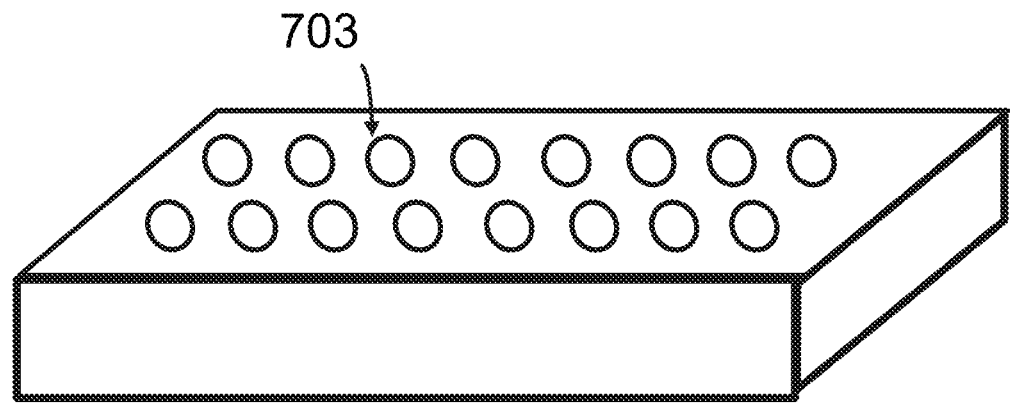
FIGS. 7A-7C depict a zoom in of a flexible structure, having spots, channels, or wells, respectively.
Figure 7B:
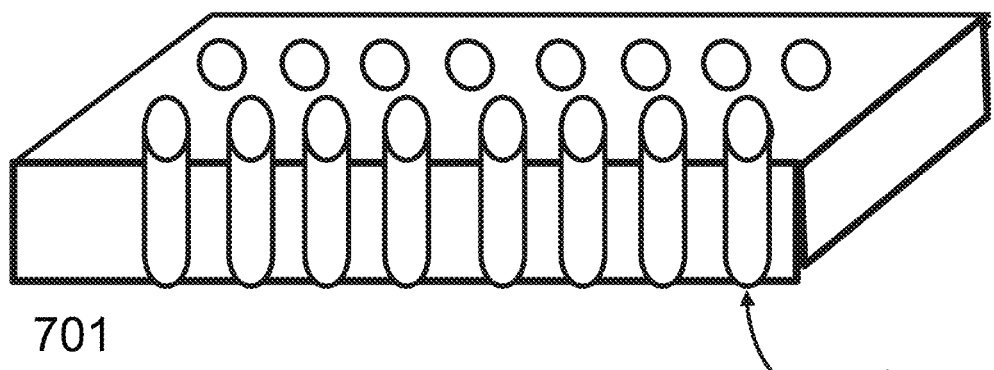
Figure 7C:
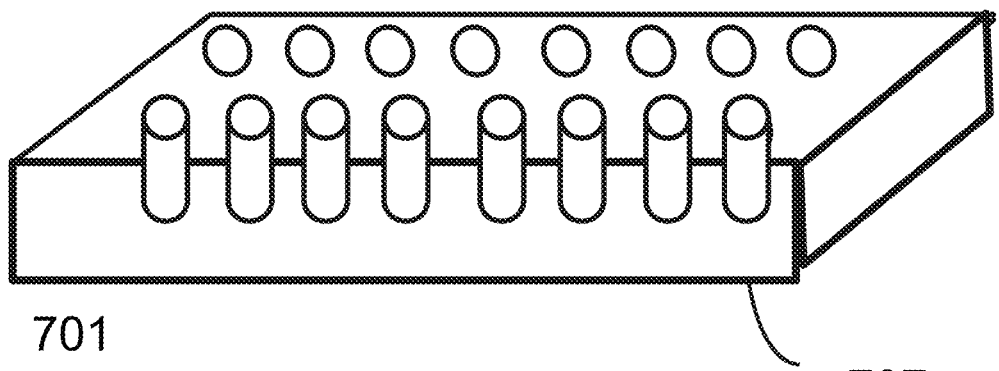

In the case of flexible structures, provided herein are devices wherein the flexible structure comprises a continuous loop 601 wrapped around one or more fixed structures, e.g., a pair of rollers 603 or a non-continuous flexible structure 607 wrapped around separate fixed structures, e.g., a pair reels 605. See FIGS. 6A-6B. In some instances, the structures comprise multiple regions for polynucleotide synthesis. An exemplary structure is illustrated in FIG. 6C where a plate comprises distinct regions 609 for polynucleotide synthesis. The distinct regions 609 may be separated 611 by breaking or cutting. Each of the distinct regions may be further released, sequenced, decrypted, and read 613 or stored 615. An alternative structure is illustrated in FIG. 6D in which a tape comprises distinct regions 617 for polynucleotide synthesis. The distinct regions 617 may be separated 619 by breaking or cutting. Each of the distinct regions may be further released, sequenced, decrypted, and read 621 or stored 623. Provided herein are flexible structures having a surface with a plurality of loci for polynucleotide extension. FIGS. 7A-7C show a zoom in of the locus in the flexible structure. Each locus in a portion of the flexible structure 701, may be a substantially planar spot 703 (e.g., flat), a channel 705, or a well 707. In some instances, each locus of the structure has a width of about 10 um and a distance between the center of each structure of about 21 um. Loci may comprise, without limitation, circular, rectangular, tapered, or rounded shapes. Alternatively or in combination, the structures are rigid. In some instances, the rigid structures comprise loci for polynucleotide synthesis. In some instances, the rigid structures comprise substantially planar regions, channels, or wells for polynucleotide synthesis.

In some instances, a well described herein has a width to depth (or height) ratio of 1 to 0.01, wherein the width is a measurement of the width at the narrowest segment of the well. In some instances, a well described herein has a width to depth (or height) ratio of 0.5 to 0.01, wherein the width is a measurement of the width at the narrowest segment of the well. In some instances, a well described herein has a width to depth (or height) ratio of about 0.01, 0.05, 0.1, 0.15, 0.16, 0.2, 0.5, or 1. Provided herein are structures for polynucleotide synthesis comprising a plurality of discrete loci for polynucleotide synthesis. Exemplary structures for the loci include, without limitation, substantially planar regions, channels, wells or protrusions. Structures described herein are may comprise a plurality of clusters, each cluster comprising a plurality of wells, loci or channels. Alternatively, described herein are may comprise a homogenous arrangement of wells, loci or channels. Structures provided herein may comprise wells having a height or depth from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some instances, the height of a well is less than 100 um, less than 80 um, less than 60 um, less than 40 um or less than 20 um. In some instances, well height is about 10, 20, 30, 40, 50, 60, 70, 80, 90, 100, 200, 300, 400, 500 um or more. In some instances, the height or depth of the well is at least 10, 25, 50, 75, 100, 200, 300, 400, 500, 600, 700, 800, 900, 1000, or more than 1000 nm. In some instances, the height or depth of the well is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the height or depth of the well is in a range of about 50 nm to about 1 um. In some instances, well height is about 10, 20, 30, 40, 50, 60, 70, 80, 90, 100, 200, 300, 400, 500, 700, 800, 900 or about 1000 nm.

Structures for polynucleotide synthesis provided herein may comprise channels. The channels may have a width to depth (or height) ratio of 1 to 0.01, wherein the width is a measurement of the width at the narrowest segment of the microchannel. In some instances, a channel described herein has a width to depth (or height) ratio of 0.5 to 0.01, wherein the width is a measurement of the width at the narrowest segment of the microchannel. In some instances, a channel described herein has a width to depth (or height) ratio of about 0.01, 0.05, 0.1, 0.15, 0.16, 0.2, 0.5, or 1.

Described herein are structures for polynucleotide synthesis comprising a plurality of discrete loci. Structures comprise, without limitation, substantially planar regions, channels, protrusions, or wells for polynucleotide synthesis. In some instances, structures described herein are provided comprising a plurality of channels, wherein the height or depth of the channel is from about 5 um to about 500 um, from about 5 um to about 400 um, from about 5 um to about 300 um, from about 5 um to about 200 um, from about 5 um to about 100 um, from about 5 um to about 50 um, or from about 10 um to about 50 um. In some cases, the height of a channel is less than 100 um, less than 80 um, less than 60 um, less than 40 um or less than 20 um. In some cases, channel height is about 10, 20, 30, 40, 50, 60, 70, 80, 90, 100, 200, 300, 400, 500 um or more. In some instances, the height or depth of the channel is at least 10, 25, 50, 75, 100, 200, 300, 400, 500, 600, 700, 800, 900, 1000, or more than 1000 nm. In some instances, the height or depth of the channel is in a range of about 10 nm to about 1000 nm, about 25 nm to about 900 nm, about 50 nm to about 800 nm, about 75 nm to about 700 nm, about 100 nm to about 600 nm, or about 200 nm to about 500. Channels described herein may be arranged on a surface in clusters or as a homogenous field.

The width of a locus on the surface of a structure for polynucleotide synthesis described herein may be from about 0.1 um to about 500 um, from about 0.5 um to about 500 um, from about 1 um to about 200 um, from about 1 um to about 100 um, from about 5 um to about 100 um, or from about 0.1 um to about 100 um, for example, about 90 um, 80 um, 70 um, 60 um, 50 um, 40 um, 30 um, 20 um, 10 um, 5 um, 1 um or 0.5 um. In some instances, the width of a locus is less than about 100 um, 90 um, 80 um, 70 um, 60 um, 50 um, 40 um, 30 um, 20 um or 10 um. In some instances, the width of a locus is at least 10, 25, 50, 75, 100, 200, 300, 400, 500, 600, 700, 800, 900, 1000, or more than 1000 nm. In some instances, the width of a locus is in a range of about 10 nm to about 1000 nm, about 25 nm to about 900 nm, about 50 nm to about 800 nm, about 75 nm to about 700 nm, about 100 nm to about 600 nm, or about 200 nm to about 500. In some instances, the width of a locus is in a range of about 50 nm to about 1000 nm. In some instances, the distance between the center of two adjacent loci is from about 0.1 um to about 500 um, 0.5 um to about 500 um, from about 1 um to about 200 um, from about 1 um to about 100 um, from about 5 um to about 200 um, from about 5 um to about 100 um, from about 5 um to about 50 um, or from about 5 um to about 30 um, for example, about 20 um. In some instances, the total width of a locus is about 5 um, 10 um, 20 um, 30 um, 40 um, 50 um, 60 um, 70 um, 80 um, 90 um, or 100 um. In some instances, the total width of a locus is about 1 um to 100 um, 30 um to 100 um, or 50 um to 70 um. In some instances, the distance between the center of two adjacent loci is from about 0.5 um to about 2 um, 0.5 um to about 2 um, from about 0.75 um to about 2 um, from about 1 um to about 2 um, from about 0.2 um to about 1 um, from about 0.5 um to about 1.5 um, from about 0.5 um to about 0.8 um, or from about 0.5 um to about 1 um, for example, about 1 um. In some instances, the total width of a locus is about 50 nm, 0.1 um, 0.2 um, 0.3 um, 0.4 um, 0.5 um, 0.6 um, 0.7 um, 0.8 um, 0.9 um, 1 um, 1.1 um, 1.2 um, 1.3 um, 1.4 um, or 1.5 um. In some instances, the total width of a locus is about 0.5 um to 2 um, 0.75 um to 1 um, or 0.9 um to 2 um.

In some instances, each locus supports the synthesis of a population of polynucleotides having a different sequence than a population of polynucleotides grown on another locus. Provided herein are surfaces which comprise at least 10, 100, 256, 500, 1000, 2000, 3000, 4000, 5000, 6000, 7000, 8000, 9000, 10000, 11000, 12000, 13000, 14000, 15000, 20000, 30000, 40000, 50000 or more clusters. Provided herein are surfaces which comprise more than 2,000; 5,000; 10,000; 20,000; 30,000; 50,000; 100,000; 200,000; 300,000; 400,000; 500,000; 600,000; 700,000; 800,000; 900,000; 1,000,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150, 200, 500 or more loci. In some cases, each cluster includes 50 to 500, 50 to 200, 50 to 150, or 100 to 150 loci. In some cases, each cluster includes 100 to 150 loci. In some instances, each cluster includes 109, 121, 130 or 137 loci.

Provided herein are loci having a width at the longest segment of 5 to 100 um. In some cases, the loci have a width at the longest segment of about 30, 35, 40, 45, 50, 55 or 60 um. In some cases, the loci are channels having multiple segments, wherein each segment has a center to center distance apart of 5 to 50 um. In some cases, the center to center distance apart for each segment is about 5, 10, 15, 20 or 25 um.

In some instances, the number of distinct polynucleotides synthesized on the surface of a structure described herein is dependent on the number of distinct loci available in the substrate. In some instances, the density of loci within a cluster of a substrate is at least or about 1 locus per $mm^2$, 10 loci per $mm^2$, 25 loci per $mm^2$, 50 loci per $mm^2$, 65 loci per $mm^2$, 75 loci per $mm^2$, 100 loci per $mm^2$, 130 loci per $mm^2$, 150 loci per $mm^2$, 175 loci per $mm^2$, 200 loci per $mm^2$, 300 loci per $mm^2$, 400 loci per $mm^2$, 500 loci per $mm^2$, 1,000 loci per $mm^2$, $10^4$ loci per $mm^2$, $10^5$ loci per $mm^2$, $10^6$ loci per $mm^2$, or more. In some cases, a substrate comprises from about 10 loci per $mm^2$ to about 500 $mm^2$, from about 25 loci per $mm^2$ to about 400 $mm^2$, from about 50 loci per $mm^2$ to about 500 $mm^2$, from about 100 loci per $mm^2$ to about 500 $mm^2$, from about 150 loci per $mm^2$ to about 500 $mm^2$, from about 10 loci per $mm^2$ to about 250 $mm^2$, from about 50 loci per $mm^2$ to about 250 $mm^2$, from about 10 loci per $mm^2$ to about 200 $mm^2$, or from about 50 loci per $mm^2$ to about 200 $mm^2$. In some cases, a substrate comprises from about $10^4$ loci per $mm^2$ to about $10^5$ $mm^2$. In some cases, a substrate comprises from about $10^5$ loci per $mm^2$ to about $10^7$ $mm^2$. In some cases, a substrate comprises at least $10^5$ loci per $mm^2$. In some cases, a substrate comprises at least $10^6$ loci per $mm^2$. In some cases, a substrate comprises at least $10^7$ loci per $mm^2$. In some cases, a substrate comprises from about $10^4$ loci per $mm^2$ to about $10^5$ $mm^2$. In some instances, the density of loci within a cluster of a substrate is at least or about 1 locus per $um^2$, 10 loci per $um^2$, 25 loci per $um^2$, 50 loci per $um^2$, 65 loci per $um^2$, 75 loci per $um^2$, 100 loci per $um^2$, 130 loci per $um^2$, 150 loci per $um^2$, 175 loci per $um^2$, 200 loci per $um^2$, 300 loci per $um^2$, 400 loci per $um^2$, 500 loci per $um^2$, 1,000 loci per $um^2$ or more. In some cases, a substrate comprises from about 10 loci per $um^2$ to about 500 $um^2$, from about 25 loci per $um^2$ to about 400 $um^2$, from about 50 loci per $um^2$ to about 500 $um^2$, from about 100 loci per $um^2$ to about 500 $um^2$, from about 150 loci per $um^2$ to about 500 $um^2$, from about 10 loci per $um^2$ to about 250 $um^2$, from about 50 loci per $um^2$ to about 250 $um^2$, from about 10 loci per $um^2$ to about 200 $um^2$, or from about 50 loci per $um^2$ to about 200 $um^2$.

In some instances, the distance between the centers of two adjacent loci within a cluster is from about 10 um to about 500 um, from about 10 um to about 200 um, or from about 10 um to about 100 um. In some cases, the distance between two centers of adjacent loci is greater than about 10 um, 20 um, 30 um, 40 um, 50 um, 60 um, 70 um, 80 um, 90 um or 100 um. In some cases, the distance between the centers of two adjacent loci is less than about 200 um, 150 um, 100 um, 80 um, 70 um, 60 um, 50 um, 40 um, 30 um, 20 um or 10 um. In some cases, the distance between the centers of two adjacent loci is less than about 10000 nm, 8000 nm, 6000 nm, 4000 nm, 2000 nm 1000 nm, 800 nm, 600 nm, 400 nm, 200 nm, 150 nm, 100 nm, 80 um, 70 nm, 60 nm, 50 nm, 40 nm, 30 nm, 20 nm or 10 nm. In some instances, each square meter of a structure described herein allows for at least $10^7$, $10^8$, $10^9$, $10^{10}$, $10^{11}$ loci, where each locus supports one polynucleotide. In some instances, $10^9$ polynucleotides are supported on less than about 6, 5, 4, 3, 2 or 1 $m^2$ of a structure described herein.

In some instances, a structure described herein provides support for the synthesis of more than 2,000; 5,000; 10,000; 20,000; 30,000; 50,000; 100,000; 200,000; 300,000; 400, 000; 500,000; 600,000; 700,000; 800,000; 900,000; 1,000, 000; 1,200,000; 1,400,000; 1,600,000; 1,800,000; 2,000, 000; 2,500,000; 3,000,000; 3,500,000; 4,000,000; 4,500, 000; 5,000,000; 10,000,000 or more non-identical polynucleotides. In some cases, the structure provides support for the synthesis of more than 2,000; 5,000; 10,000; 20,000; 50,000; 100,000; 200,000; 300,000; 400,000; 500, 000; 600,000; 700,000; 800,000; 900,000; 1,000,000; 1,200, 000; 1,400,000; 1,600,000; 1,800,000; 2,000,000; 2,500, 000; 3,000,000; 3,500,000; 4,000,000; 4,500,000; 5,000, 000; 10,000,000 or more polynucleotides encoding for distinct sequences. In some instances, at least a portion of the polynucleotides have an identical sequence or are configured to be synthesized with an identical sequence. In some instances, the structure provides a surface environment for the growth of polynucleotides having at least 50, 60, 70, 75, 80, 85, 90, 95, 100, 110, 120, 130, 140, 150, 160, 175, 200, 225, 250, 275, 300, 325, 350, 375, 400, 425, 450, 475, 500 bases or more. In some arrangements, structures for polynucleotide synthesis described herein comprise sites for polynucleotide synthesis in a uniform arrangement.

In some instances, polynucleotides are synthesized on distinct loci of a structure, wherein each locus supports the synthesis of a population of polynucleotides. In some cases, each locus supports the synthesis of a population of polynucleotides having a different sequence than a population of polynucleotides grown on another locus. In some instances, the loci of a structure are located within a plurality of clusters. In some instances, a structure comprises at least 10, 500, 1000, 2000, 3000, 4000, 5000, 6000, 7000, 8000, 9000, 10000, 11000, 12000, 13000, 14000, 15000, 20000, 30000, 40000, 50000 or more clusters. In some instances, a structure comprises more than 2,000; 5,000; 10,000; 100,000; 200,000; 300,000; 400,000; 500,000; 600,000; 700,000; 800,000; 900,000; 1,000,000; 1,100,000; 1,200,000; 1,300,000; 1,400,000; 1,500,000; 1,600,000; 1,700,000; 1,800,000; 1,900,000; 2,000,000; 300,000; 400,000; 500,000; 600,000; 700,000; 800,000; 900,000; 1,000,000; 1,200,000; 1,400,000; 1,600,000; 1,800,000; 2,000,000; 2,500,000; 3,000,000; 3,500,000; 4,000,000; 4,500,000; 5,000,000; or 10,000,000 or more distinct loci. In some cases, each cluster includes 1, 2, 3, 4, 5, 6, 7, 8, 9, 10, 20, 30, 40, 50, 60, 70, 80, 90, 100, 120, 130, 150 or more loci. In some instances, each cluster includes 50 to 500, 100 to 150, or 100 to 200 loci. In some instances, each cluster includes 109, 121, 130 or 137 loci. In some instances, each cluster includes 5, 6, 7, 8, 9, 10, 11 or 12 loci. In some instances, polynucleotides from distinct loci within one cluster have sequences that, when assembled, encode for a contiguous longer polynucleotide of a predetermined sequence.

Structure Size

In some instances, a structure described herein is about the size of a plate (e.g., chip), for example between about 40 and 120 mm by between about 25 and 100 mm. In some instances, a structure described herein has a diameter less than or equal to about 1000 mm, 500 mm, 450 mm, 400 mm, 300 mm, 250 nm, 200 mm, 150 mm, 100 mm or 50 mm. In some instances, the diameter of a substrate is between about 25 mm and 1000 mm, between about 25 mm and about 800 mm, between about 25 mm and about 600 mm, between about 25 mm and about 500 mm, between about 25 mm and about 400 mm, between about 25 mm and about 300 mm, or between about 25 mm and about 200. Non-limiting examples of substrate size include about 300 mm, 200 mm, 150 mm, 130 mm, 100 mm, 84 mm, 76 mm, 54 mm, 51 mm and 25 mm. In some instances, a substrate has a planar surface area of at least 100 mm$^2$; 200 mm$^2$; 500 mm$^2$; 1,000 mm$^2$; 2,000 mm$^2$; 4,500 mm$^2$; 5,000 mm$^2$; 10,000 mm$^2$; 12,000 mm$^2$; 15,000 mm$^2$; 20,000 mm$^2$; 30,000 mm$^2$; 40,000 mm$^2$; 50,000 mm$^2$ or more. In some instances, the thickness is between about 50 mm and about 2000 mm, between about 50 mm and about 1000 mm, between about 100 mm and about 1000 mm, between about 200 mm and about 1000 mm, or between about 250 mm and about 1000 mm. Non-limiting examples thickness include 275 mm, 375 mm, 525 mm, 625 mm, 675 mm, 725 mm, 775 mm and 925 mm. In some instances, the thickness is at least or about 0.5 mm, 1.0 mm, 1.5 mm, 2.0 mm, 2.5 mm, 3.0 mm, 3.5 mm, 4.0 mm, or more than 4.0 mm. In some cases, the thickness of varies with diameter and depends on the composition of the substrate. For example, a structure comprising materials other than silicon may have a different thickness than a silicon structure of the same diameter. Structure thickness may be determined by the mechanical strength of the material used and the structure must be thick enough to support its own weight without cracking during handling. In some instances, a structure is more than about 1, 2, 3, 4, 5, 10, 15, 30, 40, 50 feet in any one dimension.

Materials

Provided herein are devices comprising a surface, wherein the surface is modified to support polynucleotide synthesis at predetermined locations and with a resulting low error rate, a low dropout rate, a high yield, and a high oligo representation. In some instances, surfaces of devices for polynucleotide synthesis provided herein are fabricated from a variety of materials capable of modification to support a de novo polynucleotide synthesis reaction. In some cases, the devices are sufficiently conductive, e.g., are able to form uniform electric fields across all or a portion of the devices. Devices described herein may comprise a flexible material. Exemplary flexible materials include, without limitation, modified nylon, unmodified nylon, nitrocellulose, and polypropylene. Devices described herein may comprise a rigid material. Exemplary rigid materials include, without limitation, glass, fuse silica, silicon, silicon dioxide, silicon nitride, plastics (for example, polytetrafluoroethylene, polypropylene, polystyrene, polycarbonate, and blends thereof, and metals (for example, gold, platinum). Devices disclosed herein may be fabricated from a material comprising silicon, polystyrene, agarose, dextran, cellulosic polymers, polyacrylamides, polydimethylsiloxane (PDMS), glass, or any combination thereof. In some cases, devices disclosed herein are manufactured with a combination of materials listed herein or any other suitable material known in the art.

Devices described herein may comprise material having a range of tensile strength. Exemplary materials having a range of tensile strengths include, but are not limited to, nylon (70 MPa), nitrocellulose (1.5 MPa), polypropylene (40 MPa), silicon (268 MPa), polystyrene (40 MPa), agarose (1-10 MPa), polyacrylamide (1-10 MPa), polydimethylsiloxane (PDMS) (3.9-10.8 MPa). Solid supports described herein can have a tensile strength from 1 to 300, 1 to 40, 1 to 10, 1 to 5, or 3 to 11 MPa. Solid supports described herein can have a tensile strength of about 1, 1.5, 2, 3, 4, 5, 6, 7, 8, 9, 10, 11, 20, 25, 40, 50, 60, 70, 80, 90, 100, 150, 200, 250, 270, or more MPa. In some instances, a device described herein comprises a solid support for polynucleotide synthesis that is in the form of a flexible material capable of being stored in a continuous loop or reel, such as a tape or flexible sheet.

Young's modulus measures the resistance of a material to elastic (recoverable) deformation under load. Exemplary materials having a range of Young's modulus stiffness include, but are not limited to, nylon (3 GPa), nitrocellulose (1.5 GPa), polypropylene (2 GPa), silicon (150 GPa), polystyrene (3 GPa), agarose (1-10 GPa), polyacrylamide (1-10 GPa), polydimethylsiloxane (PDMS) (1-10 GPa). Solid supports described herein can have a Young's moduli from 1 to 500, 1 to 40, 1 to 10, 1 to 5, or 3 to 11 GPa. Solid supports described herein can have a Young's moduli of about 1, 1.5, 2, 3, 4, 5, 6, 7, 8, 9, 10, 11, 20, 25, 40, 50, 60, 70, 80, 90, 100, 150, 200, 250, 400, 500 GPa, or more. As the relationship between flexibility and stiffness are inverse to each other, a flexible material has a low Young's modulus and changes its shape considerably under load. In some instances, a solid support described herein has a surface with a flexibility of at least nylon.

In some cases, devices disclosed herein comprise a silicon dioxide base and a surface layer of silicon oxide. Alternatively, the devices may have a base of silicon oxide. Surface of the devices provided here may be textured, resulting in an increase overall surface area for polynucleotide synthesis. Devices disclosed herein in some instances comprise at least 5%, 10%, 25%, 50%, 80%, 90%, 95%, or 99% silicon. Devices disclosed herein in some instances are fabricated from silicon on insulator (SOI) wafer.

The structure may be fabricated from a variety of materials, suitable for the methods and compositions of the invention described herein. In instances, the materials from which the substrates/solid supports of the comprising the invention are fabricated exhibit a low level of polynucleotide binding. In some situations, material that are transparent to visible and/or UV light can be employed. Materials that are sufficiently conductive, e.g. those that can form uniform electric fields across all or a portion of the substrates/solids support described herein, can be utilized. In some instances, such materials may be connected to an electric ground. In some cases, the substrate or solid support can be heat conductive or insulated. The materials can be chemical resistant and heat resistant to support chemical or biochemical reactions such as a series of polynucleotide synthesis reactions. For flexible materials, materials of interest can include: nylon, both modified and unmodified, nitrocellulose, polypropylene, and the like.

For rigid materials, specific materials of interest include: glass; fuse silica; silicon, plastics (for example polytetrafluoroethylene, polypropylene, polystyrene, polycarbonate, and blends thereof, and the like); metals (for example, gold, platinum, and the like). The structure can be fabricated from a material selected from the group consisting of silicon, polystyrene, agarose, dextran, cellulosic polymers, polyacrylamides, polydimethylsiloxane (PDMS), and glass. The substrates/solid supports or the microstructures, reactors therein may be manufactured with a combination of materials listed herein or any other suitable material known in the art.

In some instances, a substrate disclosed herein comprises a computer readable material. Computer readable materials include, without limitation, magnetic media, reel-to-reel tape, cartridge tape, cassette tape, flexible disk, paper media, film, microfiche, continuous tape (e.g., a belt) and any media suitable for storing electronic instructions. In some cases, the substrate comprises magnetic reel-to-reel tape or a magnetic belt. In some instances, the substrate comprises a flexible printed circuit board.

Structures described herein may be transparent to visible and/or UV light. In some instances, structures described herein are sufficiently conductive to form uniform electric fields across all or a portion of a structure. In some instances, structures described herein are heat conductive or insulated. In some instances, the structures are chemical resistant and heat resistant to support a chemical reaction such as a polynucleotide synthesis reaction. In some instances, the substrate is magnetic. In some instances, the structures comprise a metal or a metal alloy.

Structures for polynucleotide synthesis may be over 1, 2, 5, 10, 30, 50 or more feet long in any dimension. In the case of a flexible structure, the flexible structure is optionally stored in a wound state, e.g., in a reel. In the case of a large rigid structure, e.g., greater than 1 foot in length, the rigid structure can be stored vertically or horizontally.

Surface Preparation

Provided herein are methods to support the immobilization of a biomolecule on a substrate, where a surface of a structure described herein comprises a material and/or is coated with a material that facilitates a coupling reaction with the biomolecule for attachment. To prepare a structure for biomolecule immobilization, surface modifications may be employed that chemically and/or physically alter the substrate surface by an additive or subtractive process to change one or more chemical and/or physical properties of a substrate surface or a selected site or region of the surface. For example, surface modification involves (1) changing the wetting properties of a surface, (2) functionalizing a surface, i.e. providing, modifying or substituting surface functional groups, (3) defunctionalizing a surface, i.e. removing surface functional groups, (4) otherwise altering the chemical composition of a surface, e.g., through etching, (5) increasing or decreasing surface roughness, (6) providing a coating on a surface, e.g., a coating that exhibits wetting properties that are different from the wetting properties of the surface, and/or (7) depositing particulates on a surface. In some instances, the surface of a structure is selectively functionalized to produce two or more distinct areas on a structure, wherein at least one area has a different surface or chemical property that another area of the same structure. Such properties include, without limitation, surface energy, chemical termination, surface concentration of a chemical moiety, and the like.

In some instances, a surface of a structure disclosed herein is modified to comprise one or more actively functionalized surfaces configured to bind to both the surface of the substrate and a biomolecule, thereby supporting a coupling reaction to the surface. In some instances, the surface is also functionalized with a passive material that does not efficiently bind the biomolecule, thereby preventing biomolecule attachment at sites where the passive functionalization agent is bound. In some cases, the surface comprises an active layer only defining distinct loci for biomolecule support.

In some instances, the surface is contacted with a mixture of functionalization groups which are in any different ratio. In some instances, a mixture comprises at least 2, 3, 4, 5 or more different types of functionalization agents. In some cases, the ratio of the at least two types of surface functionalization agents in a mixture is about 1:1, 1:2, 1:5, 1:10, 2:10, 3:10, 4:10, 5:10, 6:10, 7:10, 8:10, 9:10, or any other ratio to achieve a desired surface representation of two groups. In some instances, desired surface tensions, wettabilities, water contact angles, and/or contact angles for other suitable solvents are achieved by providing a substrate surface with a suitable ratio of functionalization agents. In some cases, the agents in a mixture are chosen from suitable reactive and inert moieties, thus diluting the surface density of reactive groups to a desired level for downstream reactions. In some instances, the mixture of functionalization reagents comprises one or more reagents that bind to a biomolecule and one or more reagents that do not bind to a biomolecule. Therefore, modulation of the reagents allows for the control of the amount of biomolecule binding that occurs at a distinct area of functionalization.

In some instances, a method for substrate functionalization comprises deposition of a silane molecule onto a surface of a substrate. The silane molecule may be deposited on a high energy surface of the substrate. In some instances the high surface energy region includes a passive functionalization reagent. Methods described herein provide for a silane group to bind the surface, while the rest of the molecule provides a distance from the surface and a free hydroxyl group at the end to which a biomolecule attaches. In some instances, the silane is an organofunctional alkoxysilane molecule. Non-limiting examples of organofunctional alkoxysilane molecules include dimethylchloro-octodecyl-silane, methyldichloro-octodecyl-silane, trichloro-octodecyl-silane, and trimethyl-octodecyl-silane, triethyl-octodecyl-silane. In some instances, the silane is an amino silane. Examples of amino silanes include, without limitation, 11-acetoxyundecyltriethoxysilane, n-decyltriethoxysilane, (3-aminopropyl)trimethoxysilane, (3-aminopropyl)triethoxysilane, glycidyloxypropyl/trimethoxysilane and N-(3-triethoxysilylpropyl)-4-hydroxybutyramide. In some instances, the silane comprises 11-acetoxyundecyltriethoxysilane, n-decyltriethoxysilane, (3-aminopropyl)trimethoxysilane, (3-aminopropyl)triethoxysilane, glycidyloxypropyl/trimethoxysilane, N-(3-triethoxysilylpropyl)-4-hydroxybutyramide, or any combination thereof. In some instances, an active functionalization agent comprises 11-acetoxyundecyltriethoxysilane. In some instances, an active functionalization agent comprises n-decyltriethoxysilane. In some cases, an active functionalization agent comprises glycidyloxypropyltriethoxysilane (GOPS). In some instances, the silane is a fluorosilane. In some instances, the silane is a hydrocarbon silane. In some cases, the silane is 3-iodo-propyltrimethoxysilane. In some cases, the silane is octylchlorosilane.

In some instances, silanization is performed on a surface through self-assembly with organofunctional alkoxysilane molecules. The organofunctional alkoxysilanes are classified according to their organic functions. Non-limiting examples of siloxane functionalizing reagents include hydroxyalkyl siloxanes (silylate surface, functionalizing with diborane and oxidizing the alcohol by hydrogen peroxide), diol (dihydroxyalkyl) siloxanes (silylate surface, and hydrolyzing to diol), aminoalkyl siloxanes (amines require no intermediate functionalizing step), glycidoxysilanes (3-glycidoxypropyl-dimethyl-ethoxysilane, glycidoxy-trimethoxysilane), mercaptosilanes (3-mercaptopropyl-trimethoxysilane, 3-4 epoxycyclohexyl-ethyltrimethoxysilane or 3-mercaptopropyl-methyl-dimethoxysilane), bicyclohepthenyl-trichlorosilane, butyl-aldehydr-trimethoxysilane, or dimeric secondary aminoalkyl siloxanes. Exemplary hydroxyalkyl siloxanes include allyl trichlorochlorosilane turning into 3-hydroxypropyl, or 7-oct-1-enyl trichlorochlorosilane turning into 8-hydroxyoctyl. The diol (dihydroxyalkyl) siloxanes include glycidyl trimethoxysilane-derived (2,3-dihydroxypropyloxy)propyl (GOPS). The aminoalkyl siloxanes include 3-aminopropyl trimethoxysilane turning into 3-aminopropyl (3-aminopropyl-triethoxysilane, 3-aminopropyl-diethoxy-methylsilane, 3-aminopropyl-dimethyl-ethoxysilane, or 3-aminopropyl-trimethoxysilane). In some cases, the dimeric secondary aminoalkyl siloxanes is bis(3-trimethoxysilylpropyl) amine turning into bis(silyloxypropyl)amine.

Active functionalization areas may comprise one or more different species of silanes, for example, 1, 2, 3, 4, 5, 6, 7, 8, 9, 10 or more silanes. In some cases, one of the one or more silanes is present in the functionalization composition in an amount greater than another silane. For example, a mixed silane solution having two silanes comprises a 99:1, 98:2, 97:3, 96:4, 95:5, 94:6, 93:7, 92:8, 91:9, 90:10, 89:11, 88:12, 87:13, 86:14, 85:15, 84:16, 83:17, 82:18, 81:19, 80:20, 75:25, 70:30, 65:35, 60:40, 55:45 ratio of one silane to another silane. In some instances, an active functionalization agent comprises 11-acetoxyundecyltriethoxysilane and n-decyltriethoxysilane. In some instances, an active functionalization agent comprises 11-acetoxyundecyltriethoxysilane and n-decyltriethoxysilane in a ratio from about 20:80 to about 1:99, or about 10:90 to about 2:98, or about 5:95.

In some instances, functionalization comprises deposition of a functionalization agent to a structure by any deposition technique, including, but not limiting to, chemical vapor deposition (CVD), atomic layer deposition (ALD), plasma enhanced CVD (PECVD), plasma enhanced ALD (PEALD), metal organic CVD (MOCVD), hot wire CVD (HWCVD), initiated CVD (iCVD), modified CVD (MCVD), vapor axial deposition (VAD), outside vapor deposition (OVD), physical vapor deposition (e.g., sputter deposition, evaporative deposition), and molecular layer deposition (MLD).

Any step or component in the following functionalization process be omitted or changed in accordance with properties desired of the final functionalized substrate. In some cases, additional components and/or process steps are added to the process workflows embodied herein. In some instances, a substrate is first cleaned, for example, using a piranha solution. An example of a cleaning process includes soaking a substrate in a piranha solution (e.g., 90% $H_2SO_4$, 10% $H_2O_2$) at an elevated temperature (e.g., 120° C.) and washing (e.g., water) and drying the substrate (e.g., nitrogen gas). The process optionally includes a post piranha treatment comprising soaking the piranha treated substrate in a basic solution (e.g., $NH_4OH$) followed by an aqueous wash (e.g., water). In some instances, a surface of a structure is plasma cleaned, optionally following the piranha soak and optional post piranha treatment. An example of a plasma cleaning process comprises an oxygen plasma etch. In some instances, the surface is deposited with an active functionalization agent following by vaporization. In some instances, the substrate is actively functionalized prior to cleaning, for example, by piranha treatment and/or plasma cleaning.

The process for surface functionalization optionally comprises a resist coat and a resist strip. In some instances, following active surface functionalization, the substrate is spin coated with a resist, for example, SPR™ 3612 positive photoresist. The process for surface functionalization, in various instances, comprises lithography with patterned functionalization. In some instances, photolithography is performed following resist coating. In some instances, after lithography, the surface is visually inspected for lithography defects. The process for surface functionalization, in some instances, comprises a cleaning step, whereby residues of the substrate are removed, for example, by plasma cleaning or etching. In some instances, the plasma cleaning step is performed at some step after the lithography step.

In some instances, a surface coated with a resist is treated to remove the resist, for example, after functionalization and/or after lithography. In some cases, the resist is removed with a solvent, for example, with a stripping solution comprising N-methyl-2-pyrrolidone. In some cases, resist stripping comprises sonication or ultrasonication. In some instances, a resist is coated and stripped, followed by active functionalization of the exposed areas to create a desired differential functionalization pattern.

In some instances, the methods and compositions described herein relate to the application of photoresist for the generation of modified surface properties in selective areas, wherein the application of the photoresist relies on the fluidic properties of the surface defining the spatial distribution of the photoresist. Without being bound by theory, surface tension effects related to the applied fluid may define the flow of the photoresist. For example, surface tension and/or capillary action effects may facilitate drawing of the photoresist into small structures in a controlled fashion before the resist solvents evaporate. In some instances, resist contact points are pinned by sharp edges, thereby controlling the advance of the fluid. The underlying structures may be designed based on the desired flow patterns that are used to apply photoresist during the manufacturing and functionalization processes. A solid organic layer left behind after solvents evaporate may be used to pursue the subsequent steps of the manufacturing process. Structures may be designed to control the flow of fluids by facilitating or inhibiting wicking effects into neighboring fluidic paths. For example, a structure is designed to avoid overlap between top and bottom edges, which facilitates the keeping of the fluid in top structures allowing for a particular disposition of the resist. In an alternative example, the top and bottom edges overlap, leading to the wicking of the applied fluid into bottom structures. Appropriate designs may be selected accordingly, depending on the desired application of the resist.

In some instances, a structure described herein has a surface that comprises a material having thickness of at least or at least 0.1 nm, 0.5 nm, 1 nm, 2 nm, 5 nm, 10 nm or 25 nm that comprises a reactive group capable of binding nucleosides. Exemplary include, without limitation, glass and silicon, such as silicon dioxide and silicon nitride. In some cases, exemplary surfaces include nylon and PMMA.

In some instances, electromagnetic radiation in the form of UV light is used for surface patterning. In some instances, a lamp is used for surface patterning, and a mask mediates exposure locations of the UV light to the surface. In some instances, a laser is used for surface patterning, and a shutter opened/closed state controls exposure of the UV light to the surface. The laser arrangement may be used in combination with a flexible structure that is capable of moving. In such an arrangement, the coordination of laser exposure and flexible structure movement is used to create patterns of one or more agents having differing nucleoside coupling capabilities.

Described herein are surfaces for polynucleotide synthesis that are reusable. After synthesis and/or cleavage of polynucleotides, a surface may be bathed, washed, cleaned, baked, etched, or otherwise functionally restored to a condition suitable for subsequent polynucleotide synthesis. The number of times a surface is reused and the methods for recycling/preparing the surface for reuse vary depending on subsequent applications. Surfaces prepared for reuse are in some instances reused at least 1, 2, 3, 5, 10, 20, 50, 100, 1,000 or more times. In some instances, the remaining "life" or number of times a surface is suitable for reuse is measured or predicted.

Material Deposition Systems

In some cases, the synthesized polynucleotides are stored on the substrate, for example a solid support. Nucleic acid reagents may be deposited on the substrate surface in a non-continuous, or drop-on-demand method. Examples of such methods include the electromechanical transfer method, electric thermal transfer method, and electrostatic attraction method. In the electromechanical transfer method, piezoelectric elements deformed by electrical pulses cause the droplets to be ejected. In the electric thermal transfer method, bubbles are generated in a chamber of the device, and the expansive force of the bubbles causes the droplets to be ejected. In the electrostatic attraction method, electrostatic force of attraction is used to eject the droplets onto the substrate. In some cases, the drop frequency is from about 5 KHz to about 500 KHz; from about 5 KHz to about 100 KHz; from about 10 KHz to about 500 KHz; from about 10 KHz to about 100 KHz; or from about 50 KHz to about 500 KHz. In some cases, the frequency is less than about 500 KHz, 200 KHz, 100 KHz, or 50 KHz.

The size of the droplets dispensed correlates to the resolution of the device. In some instances, the devices deposit droplets of reagents at sizes from about 0.01 pl to about 20 pl, from about 0.01 pl to about 10 pl, from about 0.01 pl to about 1 pl, from about 0.01 pl to about 0.5 pl, from about 0.01 pl to about 0.01 pl, or from about 0.05 pl to about 1 pl. In some instances, the droplet size is less than about 1 pl, 0.5 pl, 0.2 pl, 0.1 pl, or 0.05 pl.

In some arrangements, the configuration of a polynucleotide synthesis system allows for a continuous polynucleotide synthesis process that exploits the flexibility of a substrate for traveling in a reel-to-reel type process. This synthesis process operates in a continuous production line manner with the substrate travelling through various stages of polynucleotide synthesis using one or more reels to rotate the position of the substrate. In an exemplary instance, a polynucleotide synthesis reaction comprises rolling a substrate: through a solvent bath, beneath a deposition device for phosphoramidite deposition, through a bath of oxidizing agent, through an acetonitrile wash bath, and through a deblock bath. Optionally, the tape is also traversed through a capping bath. A reel-to-reel type process allows for the finished product of a substrate comprising synthesized polynucleotides to be easily gathered on a take-up reel, where it can be transported for further processing or storage.

In some arrangements, polynucleotide synthesis proceeds in a continuous process as a continuous flexible tape is conveyed along a conveyor belt system. Similar to the reel-to-reel type process, polynucleotide synthesis on a continuous tape operates in a production line manner, with the substrate travelling through various stages of polynucleotide synthesis during conveyance. However, in a conveyor belt process, the continuous tape revisits a polynucleotide synthesis step without rolling and unrolling of the tape, as in a reel-to-reel process. In some arrangements, polynucleotide synthesis steps are partitioned into zones and a continuous tape is conveyed through each zone one or more times in a cycle. For example, a polynucleotide synthesis reaction may comprise (1) conveying a substrate through a solvent bath, beneath a deposition device for phosphoramidite deposition, through a bath of oxidizing agent, through an acetonitrile wash bath, and through a block bath in a cycle; and then (2) repeating the cycles to achieve synthesized polynucleotides of a predetermined length. After polynucleotide synthesis, the flexible substrate is removed from the conveyor belt system and, optionally, rolled for storage. Rolling may be around a reel, for storage. In some instances, a flexible substrate comprising thermoplastic material is coated with nucleoside coupling reagent. The coating is patterned into loci such that each locus has diameter of about 10 um, with a center-to-center distance between two adjacent loci of about 21 um. In this instance, the locus size is sufficient to accommodate a sessile drop volume of 0.2 pl during a polynucleotide synthesis deposition step. In some cases, the locus density is about 2.2 billion loci per $m^2$ (1 locus/441× $10^{-12}$ $m^2$). In some cases, a 4.5 $m^2$ substrate comprise about 10 billion loci, each with a 10 um diameter.

In some arrangements, a device for application of one or more reagents to a substrate during a synthesis reaction is configured to deposit reagents and/or nucleoside monomers for nucleoside phosphoramidite based synthesis. Reagents for polynucleotide synthesis include reagents for polynucleotide extension and wash buffers. As non-limiting examples, the device deposits cleaning reagents, coupling reagents, capping reagents, oxidizers, de-blocking agents, acetonitrile, gases such as nitrogen gas, and any combination thereof. In addition, the device optionally deposits reagents for the preparation and/or maintenance of substrate integrity. In some instances, the polynucleotide synthesizer deposits a drop having a diameter less than about 200 um, 100 um, or 50 um in a volume less than about 1000, 500, 100, 50, or 20 pl. In some cases, the polynucleotide synthesizer deposits between about 1 and 10000, 1 and 5000, 100 and 5000, or 1000 and 5000 droplets per second.

Described herein are devices, methods, systems and compositions where reagents for polynucleotide synthesis are recycled or reused. Recycling of reagents may comprise collection, storage, and usage of unused reagents, or purification/transformation of used reagents. For example, a reagent bath is recycled and used for a polynucleotide synthesis step on the same or a different surface. Reagents described herein may be recycled 1, 2, 3, 4, 5, 6, 7, 8, 9, 10 or more times. Alternatively or in combination, a reagent solution comprising a reaction byproduct is filtered to remove the byproduct, and the reagent solution is used for additional polynucleotide synthesis reactions.

Many integrated or non-integrated elements are often used with polynucleotide synthesis systems. In some instances, a polynucleotide synthesis system comprises one or more elements useful for downstream processing of synthesized polynucleotides. As an example, the system comprises a temperature control element such as a thermal cycling device. In some instances, the temperature control element is used with a plurality of resolved reactors to perform nucleic acid assembly such as PCA and/or nucleic acid amplification such as PCR.

De Novo Polynucleotide Synthesis

Provided herein are systems and methods for synthesis of a high density of polynucleotides on a substrate in a short amount of time. In some instances, the substrate is a flexible substrate. In some instances, at least $10^{10}$, $10^{11}$, $10^{12}$, $10^{13}$, $10^{14}$, or $10^{15}$ bases are synthesized in one day. In some instances, at least $10 \times 10^8$, $10 \times 10^9$, $10 \times 10^{10}$, $10 \times 10^{11}$, or $10 \times 10^{12}$ polynucleotides are synthesized in one day. In some cases, each polynucleotide synthesized comprises at least 20, 50, 100, 200, 300, 400 or 500 nucleobases. In some cases, these bases are synthesized with a total average error rate of less than about 1 in 100; 200; 300; 400; 500; 1000; 2000; 5000; 10000; 15000; 20000 bases. In some instances, these error rates are for at least 50%, 60%, 70%, 80%, 90%, 95%, 98%, 99%, 99.5%, or more of the polynucleotides synthesized. In some instances, these at least 90%, 95%, 98%, 99%, 99.5%, or more of the polynucleotides synthesized do not differ from a predetermined sequence for which they encode. In some instances, the error rate for synthesized polynucleotides on a substrate using the methods and systems described herein is less than about 1 in 200. In some instances, the error rate for synthesized polynucleotides on a substrate using the methods and systems described herein is less than about 1 in 1,000. In some instances, the error rate for synthesized polynucleotides on a substrate using the methods and systems described herein is less than about 1 in 2,000. In some instances, the error rate for synthesized polynucleotides on a substrate using the methods and systems described herein is less than about 1 in 3,000. In some instances, the error rate for synthesized polynucleotides on a substrate using the methods and systems described herein is less than about 1 in 5,000. Individual types of error rates include mismatches, deletions, insertions, and/or substitutions for the polynucleotides synthesized on the substrate. The term "error rate" refers to a comparison of the collective amount of synthesized polynucleotide to an aggregate of predetermined polynucleotide sequences. In some instances, synthesized polynucleotides disclosed herein comprise a tether of 12 to 25 bases. In some instances, the tether comprises 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more bases.

Described herein are methods, systems, devices, and compositions wherein chemical reactions used in polynucleotide synthesis are controlled using electrochemistry. Electrochemical reactions in some instances are controlled by any source of energy, such as light, heat, radiation, or electricity. For example, electrodes are used to control chemical reactions as all or a portion of discrete loci on a surface. Electrodes in some instances are charged by applying an electrical potential to the electrode to control one or more chemical steps in polynucleotide synthesis. In some instances, these electrodes are addressable. Any number of the chemical steps described herein is in some instances controlled with one or more electrodes. Electrochemical reactions may comprise oxidations, reductions, acid/base chemistry, or other reaction that is controlled by an electrode. In some instances, electrodes generate electrons or protons that are used as reagents for chemical transformations. Electrodes in some instances directly generate a reagent such as an acid. In some instances, an acid is a proton. Electrodes in some instances directly generate a reagent such as a base. Acids or bases are often used to cleave protecting groups, or influence the kinetics of various polynucleotide synthesis reactions, for example by adjusting the pH of a reaction solution. Electrochemically controlled polynucleotide synthesis reactions in some instances comprise redox-active metals or other redox-active organic materials. In some instances, metal or organic catalysts are employed with these electrochemical reactions. In some instances, acids are generated from oxidation of quinones.

Control of chemical reactions with is not limited to the electrochemical generation of reagents; chemical reactivity may be influenced indirectly through biophysical changes to substrates or reagents through electric fields (or gradients) which are generated by electrodes. In some instances, substrates include but are not limited to nucleic acids. In some instances, electrical fields which repel or attract specific reagents or substrates towards or away from an electrode or surface are generated. Such fields in some instances are generated by application of an electrical potential to one or more electrodes. For example, negatively charged nucleic acids are repelled from negatively charged electrode surfaces. Such repulsions or attractions of polynucleotides or other reagents caused by local electric fields in some instances provides for movement of polynucleotides or other reagents in or out of region of the synthesis device or structure. In some instances, electrodes generate electric fields which repel polynucleotides away from a synthesis surface, structure, or device. In some instances, electrodes generate electric fields which attract polynucleotides towards a synthesis surface, structure, or device. In some instances, protons are repelled from a positively charged surface to limit contact of protons with substrates or portions thereof. In some instances, repulsion or attractive forces are used to allow or block entry of reagents or substrates to specific areas of the synthesis surface. In some instances, nucleoside monomers are prevented from contacting a polynucleotide chain by application of an electric field in the vicinity of one or both components. Such arrangements allow gating of specific reagents, which may obviate the need for protecting groups when the concentration or rate of contact between reagents and/or substrates is controlled. In some instances, unprotected nucleoside monomers are used for polynucleotide synthesis. Alternatively, application of the field in the vicinity of one or both components promotes contact of nucleoside monomers with a polynucleotide chain. Additionally, application of electric fields to a substrate can alter the substrates reactivity or conformation. In an exemplary application, electric fields generated by electrodes are used to prevent polynucleotides at adjacent loci from interacting. In some instances, the substrate is a polynucleotide, optionally attached to a surface. Application of an electric field in some instances alters the three-dimensional structure of a polynucleotide. Such alterations comprise folding or unfolding of various structures, such as helices, hairpins, loops, or other 3-dimensional nucleic acid structure. Such alterations are useful for manipulating nucleic acids inside of wells, channels, or other structures. In some instances, electric fields are applied to a nucleic acid substrate to prevent secondary structures. In some instances, electric fields obviate the need for linkers or attachment to a solid support during polynucleotide synthesis.

A suitable method for polynucleotide synthesis on a substrate of this disclosure is a phosphoramidite method comprising the controlled addition of a phosphoramidite building block, i.e. nucleoside phosphoramidite, to a growing polynucleotide chain in a coupling step that forms a phosphite triester linkage between the phosphoramidite building block and a nucleoside bound to the substrate. In some instances, the nucleoside phosphoramidite is provided to the substrate activated. In some instances, the nucleoside phosphoramidite is provided to the substrate with an activator. In some instances, nucleoside phosphoramidites are provided to the substrate in a 1.5, 2, 3, 4, 5, 6, 7, 8, 9, 10, 11, 12, 13, 14, 15, 16, 17, 18, 19, 20, 25, 30, 35, 40, 50, 60, 70, 80, 90, 100-fold excess or more over the substrate-bound nucleosides. In some instances, the addition of nucleoside phosphoramidite is performed in an anhydrous environment, for example, in anhydrous acetonitrile. Following addition and linkage of a nucleoside phosphoramidite in the coupling step, the substrate is optionally washed. In some instances, the coupling step is repeated one or more additional times, optionally with a wash step between nucleoside phosphoramidite additions to the substrate. In some instances, a polynucleotide synthesis method used herein comprises 1, 2, 3 or more sequential coupling steps. Prior to coupling, in many cases, the nucleoside bound to the substrate is deprotected by removal of a protecting group, where the protecting group functions to prevent polymerization. Protecting groups may comprise any chemical group that prevents extension of the polynucleotide chain. In some instances, the protecting group is cleaved (or removed) in the presence of an acid. In some instances, the protecting group is cleaved in the presence of a base. In some instances, the protecting group is removed with electromagnetic radiation such as light, heat, or other energy source. In some instances, the protecting group is removed through an oxidation or reduction reaction. In some instances, a protecting group comprises a triarylmethyl group. In some instances, a protecting group comprises an aryl ether. In some instances, a protecting comprises a disulfide. In some instances a protecting group comprises an acid-labile silane. In some instances, a protecting group comprises an acetal. In some instances, a protecting group comprises a ketal. In some instances, a protecting group comprises an enol ether. In some instances, a protecting group comprises a methoxybenzyl group. In some instances, a protecting group comprises an azide. In some instances, a protecting group is 4,4'-dimethoxytrityl (DMT). In some instances, a protecting group is a tert-butyl carbonate. In some instances, a protecting group is a tert-butyl ester. In some instances, a protecting group comprises a base-labile group.

Following coupling, phosphoramidite polynucleotide synthesis methods optionally comprise a capping step. In a capping step, the growing polynucleotide is treated with a capping agent. A capping step generally serves to block unreacted substrate-bound 5'-OH groups after coupling from further chain elongation, preventing the formation of polynucleotides with internal base deletions. Further, phosphoramidites activated with 1H-tetrazole often react, to a small extent, with the O6 position of guanosine. Without being bound by theory, upon oxidation with $I_2$/water, this side product, possibly via O6-N7 migration, undergoes depurination. The apurinic sites can end up being cleaved in the course of the final deprotection of the polynucleotide thus reducing the yield of the full-length product. The O6 modifications may be removed by treatment with the capping reagent prior to oxidation with $I_2$/water. In some instances, inclusion of a capping step during polynucleotide synthesis decreases the error rate as compared to synthesis without capping. As an example, the capping step comprises treating the substrate-bound polynucleotide with a mixture of acetic anhydride and 1-methylimidazole. Following a capping step, the substrate is optionally washed.

Following addition of a nucleoside phosphoramidite, and optionally after capping and one or more wash steps, a substrate described herein comprises a bound growing nucleic acid that may be oxidized. The oxidation step comprises oxidizing the phosphite triester into a tetracoordinated phosphate triester, a protected precursor of the naturally occurring phosphate diester internucleoside linkage. In some instances, phosphite triesters are oxidized electrochemically. In some instances, oxidation of the growing polynucleotide is achieved by treatment with iodine and water, optionally in the presence of a weak base such as a pyridine, lutidine, or collidine. Oxidation is sometimes carried out under anhydrous conditions using tert-Butyl hydroperoxide or (1S)-(+)-(10-camphorsulfonyl)-oxaziridine (CSO). In some methods, a capping step is performed following oxidation. A second capping step allows for substrate drying, as residual water from oxidation that may persist can inhibit subsequent coupling. Following oxidation, the substrate and growing polynucleotide is optionally washed. In some instances, the step of oxidation is substituted with a sulfurization step to obtain polynucleotide phosphorothioates, wherein any capping steps can be performed after the sulfurization. Many reagents are capable of the efficient sulfur transfer, including, but not limited to, 3-(Dimethylaminomethylidene)amino)-3H-1,2,4-dithiazole-3-thione, DDTT, 3H-1,2-benzodithiol-3-one 1,1-dioxide, also known as Beaucage reagent, and N,N,N'N'-Tetraethylthiuram disulfide (TETD).

For a subsequent cycle of nucleoside incorporation to occur through coupling, a protected 5' end (or 3' end, if synthesis is conducted in a 5' to 3' direction) of the substrate bound growing polynucleotide is be removed so that the primary hydroxyl group can react with a next nucleoside phosphoramidite. In some instances, the protecting group is DMT and deblocking occurs with trichloroacetic acid in dichloromethane. In some instances, the protecting group is DMT and deblocking occurs with electrochemically generated protons. Conducting detritylation for an extended time or with stronger than recommended solutions of acids may lead to increased depurination of solid support-bound polynucleotide and thus reduces the yield of the desired full-length product. Methods and compositions described herein provide for controlled deblocking conditions limiting undesired depurination reactions. In some instances, the substrate bound polynucleotide is washed after deblocking. In some cases, efficient washing after deblocking contributes to synthesized polynucleotides having a low error rate.

Methods for the synthesis of polynucleotides on a substrate described herein may involve an iterating sequence of the following steps: application of a protected monomer to a surface of a substrate feature to link with either the surface, a linker or with a previously deprotected monomer; deprotection of the applied monomer so that it can react with a subsequently applied protected monomer; and application of another protected monomer for linking. One or more intermediate steps include oxidation and/or sulfurization. In some instances, one or more wash steps precede or follow one or all of the steps.

Methods for the synthesis of polynucleotides on a substrate described herein may comprise an oxidation step. For example, methods involve an iterating sequence of the following steps: application of a protected monomer to a surface of a substrate feature to link with either the surface, a linker or with a previously deprotected monomer; deprotection of the applied monomer so that it can react with a subsequently applied protected monomer; application of another protected monomer for linking, and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; and oxidation and/or sulfurization. In some instances, one or more wash steps precede or follow one or all of the steps.

Methods for the synthesis of polynucleotides on a substrate described herein may further comprise an iterating sequence of the following steps: application of a protected monomer to a surface of a substrate feature to link with either the surface, a linker or with a previously deprotected monomer; deprotection of the applied monomer so that it can react with a subsequently applied protected monomer; and oxidation and/or sulfurization. In some instances, one or more wash steps precede or follow one or all of the steps.

In some instances, polynucleotides are synthesized with photolabile protecting groups, where the hydroxyl groups generated on the surface are blocked by photolabile-protecting groups. When the surface is exposed to UV light, such as through a photolithographic mask, a pattern of free hydroxyl groups on the surface may be generated. These hydroxyl groups can react with photoprotected nucleoside phosphoramidites, according to phosphoramidite chemistry. A second photolithographic mask can be applied and the surface can be exposed to UV light to generate second pattern of hydroxyl groups, followed by coupling with 5'-photoprotected nucleoside phosphoramidite. Likewise, patterns can be generated and oligomer chains can be extended. Without being bound by theory, the lability of a photocleavable group depends on the wavelength and polarity of a solvent employed and the rate of photocleavage may be affected by the duration of exposure and the intensity of light. This method can leverage a number of factors such as accuracy in alignment of the masks, efficiency of removal of photo-protecting groups, and the yields of the phosphoramidite coupling step. Further, unintended leakage of light into neighboring sites can be minimized. The density of synthesized oligomer per spot can be monitored by adjusting loading of the leader nucleoside on the surface of synthesis.

The surface of a substrate described herein that provides support for polynucleotide synthesis may be chemically modified to allow for the synthesized polynucleotide chain to be cleaved from the surface. In some instances, the polynucleotide chain is cleaved at the same time as the polynucleotide is deprotected. In some cases, the polynucleotide chain is cleaved after the polynucleotide is deprotected. In an exemplary scheme, a trialkoxysilyl amine such as $(CH_3CH_2O)_3Si—(CH_2)_2—NH_2$ is reacted with surface SiOH groups of a substrate, followed by reaction with succinic anhydride with the amine to create an amide linkage and a free OH on which the nucleic acid chain growth is supported. Cleavage includes gas cleavage with ammonia or methylamine. In some instances cleavage includes linker cleavage with electrically generated reagents such as acids or bases. In some instances, once released from the surface, polynucleotides are assembled into larger nucleic acids that are sequenced and decoded to extract stored information.

The surfaces described herein can be reused after polynucleotide cleavage to support additional cycles of polynucleotide synthesis. For example, the linker can be reused without additional treatment/chemical modifications. In some instances, a linker is non-covalently bound to a substrate surface or a polynucleotide. In some embodiments, the linker remains attached to the polynucleotide after cleavage from the surface. Linkers in some embodiments comprise reversible covalent bonds such as esters, amides, ketals, beta substituted ketones, heterocycles, or other group that is capable of being reversibly cleaved. Such reversible cleavage reactions are in some instances controlled through the addition or removal of reagents, or by electrochemical processes controlled by electrodes. Optionally, chemical linkers or surface-bound chemical groups are regenerated after a number of cycles, to restore reactivity and remove unwanted side product formation on such linkers or surface-bound chemical groups.

Assembly

Polynucleotides may be designed to collectively span a large region of a predetermined sequence that encodes for information. In some instances, larger polynucleotides are generated through ligation reactions to join the synthesized polynucleotides. One example of a ligation reaction is polymerase chain assembly (PCA). In some instances, at least of a portion of the polynucleotides are designed to include an appended region that is a substrate for universal primer binding. For PCA reactions, the presynthesized polynucleotides include overlaps with each other (e.g., 4, 20, 40 or more bases with overlapping sequence). During the polymerase cycles, the polynucleotides anneal to complementary fragments and then are filled in by polymerase. Each cycle thus increases the length of various fragments randomly depending on which polynucleotides find each other. Complementarity amongst the fragments allows for forming a complete large span of double-stranded DNA. In some cases, after the PCA reaction is complete, an error correction step is conducted using mismatch repair detecting enzymes to remove mismatches in the sequence. Once larger fragments of a target sequence are generated, they can be amplified. For example, in some cases, a target sequence comprising 5' and 3' terminal adapter sequences is amplified in a polymerase chain reaction (PCR) which includes modified primers that hybridize to the adapter sequences. In some cases, the modified primers comprise one or more uracil bases. The use of modified primers allows for removal of the primers through enzymatic reactions centered on targeting the modified base and/or gaps left by enzymes which cleave the modified base pair from the fragment. What remains is a double-stranded amplification product that lacks remnants of adapter sequence. In this way, multiple amplification products can be generated in parallel with the same set of primers to generate different fragments of double-stranded DNA.

Error correction may be performed on synthesized polynucleotides and/or assembled products. An example strategy for error correction involves site-directed mutagenesis by overlap extension PCR to correct errors, which is optionally coupled with two or more rounds of cloning and sequencing. In certain instances, double-stranded nucleic acids with mismatches, bulges and small loops, chemically altered bases and/or other heteroduplexes are selectively removed from populations of correctly synthesized nucleic acids. In some instances, error correction is performed using proteins/ enzymes that recognize and bind to or next to mismatched or unpaired bases within double-stranded nucleic acids to create a single or double-strand break or to initiate a strand transfer transposition event. Non-limiting examples of proteins/enzymes for error correction include endonucleases (T7 Endonuclease I, *E. coli* Endonuclease V, T4 Endonuclease VII, mung bean nuclease, Cell, *E. coli* Endonuclease IV, UVDE), restriction enzymes, glycosylases, ribonucleases, mismatch repair enzymes, resolvases, helicases, ligases, antibodies specific for mismatches, and their variants. Examples of specific error correction enzymes include T4 endonuclease 7, T7 endonuclease 1, S1, mung bean endonuclease, MutY, MutS, MutH, MutL, cleavase, CELI, and HINF1. In some cases, DNA mismatch-binding protein MutS (*Therms aquaticus*) is used to remove failure products from a population of synthesized products. In some instances, error correction is performed using the enzyme Correctase. In some cases, error correction is performed using SURVEYOR endonuclease (Transgenomic), a mismatch-specific DNA endonuclease that scans for known and unknown mutations and polymorphisms for heteroduplex DNA.

Sequencing

After extraction and/or amplification of polynucleotides from the surface of the structure, suitable sequencing technology may be employed to sequence the polynucleotides. In some cases, the DNA sequence is read on the substrate or within a feature of a structure. In some cases, the polynucleotides stored on the substrate are extracted is optionally assembled into longer nucleic acids and then sequenced.

Polynucleotides synthesized and stored on the structures described herein encode data that can be interpreted by reading the sequence of the synthesized polynucleotides and converting the sequence into binary code readable by a computer. In some cases the sequences require assembly, and the assembly step may need to be at the nucleic acid sequence stage or at the digital sequence stage.

Provided herein are detection systems comprising a device capable of sequencing stored polynucleotides, either directly on the structure and/or after removal from the main structure. In cases where the structure is a reel-to-reel tape of flexible material, the detection system comprises a device for holding and advancing the structure through a detection location and a detector disposed proximate the detection location for detecting a signal originated from a section of the tape when the section is at the detection location. In some instances, the signal is indicative of a presence of a polynucleotide. In some instances, the signal is indicative of a sequence of a polynucleotide (e.g., a fluorescent signal). In some instances, information encoded within polynucleotides on a continuous tape is read by a computer as the tape is conveyed continuously through a detector operably connected to the computer. In some instances, a detection system comprises a computer system comprising a polynucleotide sequencing device, a database for storage and retrieval of data relating to polynucleotide sequence, software for converting DNA code of a polynucleotide sequence to binary code, a computer for reading the binary code, or any combination thereof.

Provided herein are sequencing systems that can be integrated into the devices described herein. Various methods of sequencing are well known in the art, and comprise "base calling" wherein the identity of a base in the target polynucleotide is identified. In some instances, polynucleotides synthesized using the methods, devices, compositions, and systems described herein are sequenced after cleavage from the synthesis surface. In some instances, sequencing occurs during or simultaneously with polynucleotide synthesis, wherein base calling occurs immediately after or before extension of a nucleoside monomer into the growing polynucleotide chain. Methods for base calling include measurement of electrical currents generated by polymerase-catalyzed addition of bases to a template strand. In some instances, synthesis surfaces comprise enzymes, such as polymerases. In some instances, such enzymes are tethered to electrodes or to the synthesis surface.

Computer Systems

In various aspects, any of the systems described herein are operably linked to a computer and are optionally automated through a computer either locally or remotely. In various instances, the methods and systems of the invention further comprise software programs on computer systems and use thereof. Accordingly, computerized control for the synchronization of the dispense/vacuum/refill functions such as orchestrating and synchronizing the material deposition device movement, dispense action and vacuum actuation are within the bounds of the invention. In some instances, the computer systems are programmed to interface between the user specified base sequence and the position of a material deposition device to deliver the correct reagents to specified regions of the substrate.

Figure 8:
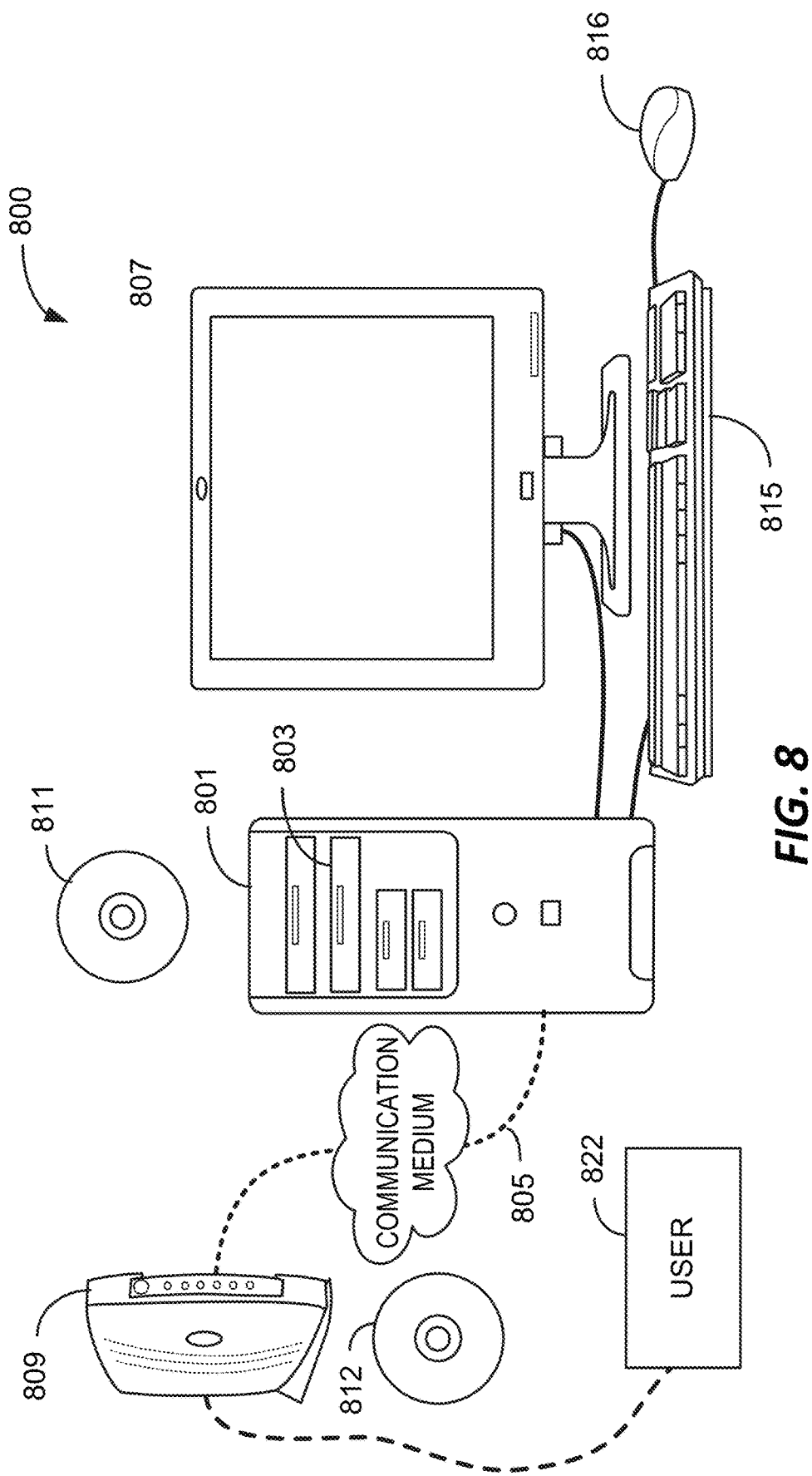
FIG. 8 illustrates an example of a computer system.

The computer system 800 illustrated in FIG. 8 may be understood as a logical apparatus that can read instructions from media 811 and/or a network port 805, which can optionally be connected to server 809 having fixed media 812. The system can include a CPU 801, disk drives 803, optional input devices such as keyboard 815 and/or mouse 816 and optional monitor 807. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 822.

Figure 9:
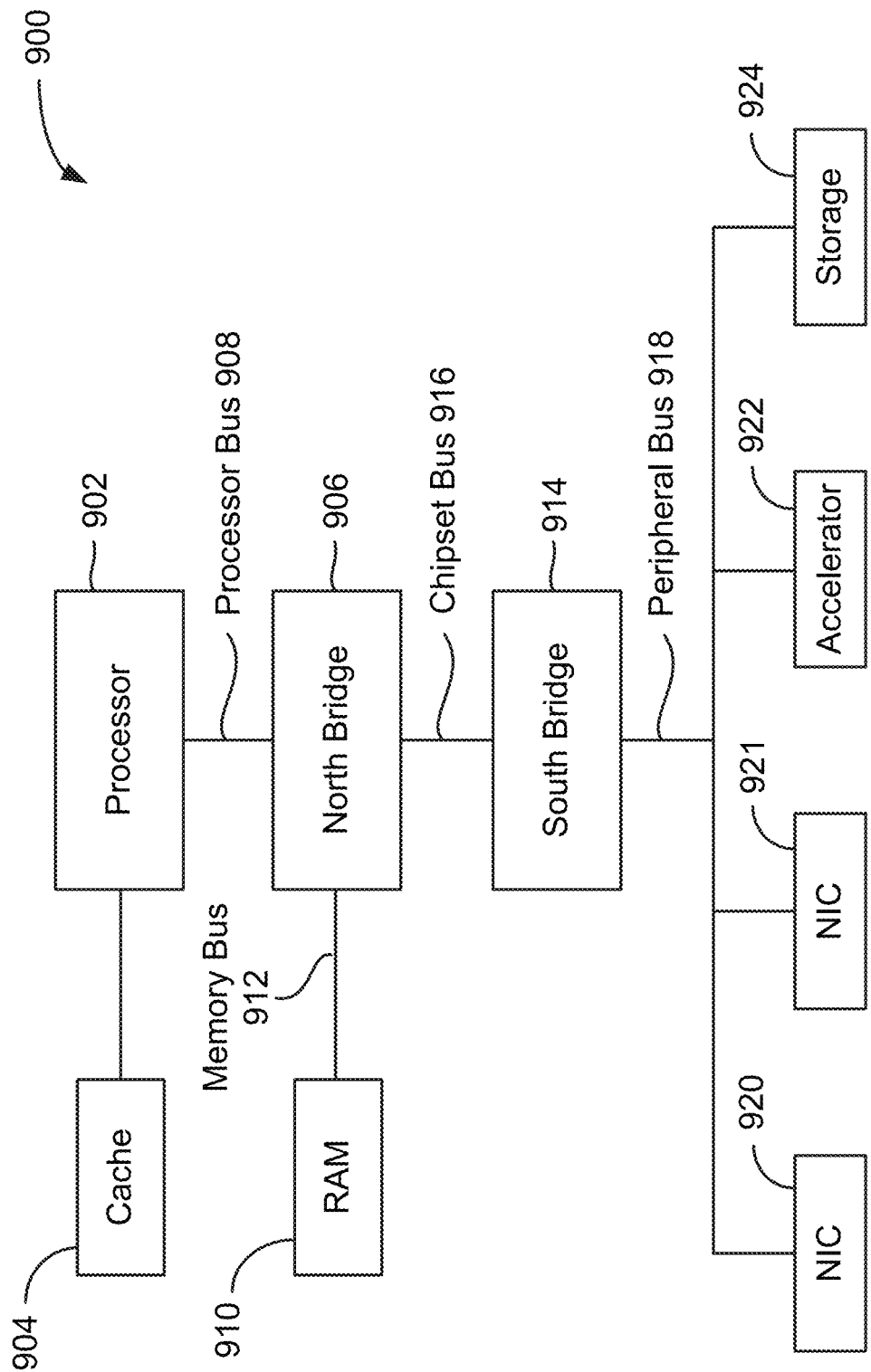
FIG. 9 is a block diagram illustrating architecture of a computer system.

FIG. 9 is a block diagram illustrating a first example architecture of a computer system that can be used in connection with example instances of the present invention. As depicted in FIG. 5, the example computer system can include a processor 902 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some instances, multiple processors or processors with multiple cores can also be used, whether in a single computer system, in a cluster, or distributed across systems over a network comprising a plurality of computers, cell phones, and/or personal data assistant devices.

As illustrated in FIG. 9, a high speed cache 904 can be connected to, or incorporated in, the processor 902 to provide a high speed memory for instructions or data that have been recently, or are frequently, used by processor 902. The processor 902 is connected to a north bridge 906 by a processor bus 908. The north bridge 906 is connected to random access memory (RAM) 910 by a memory bus 912 and manages access to the RAM 910 by the processor 902. The north bridge 906 is also connected to a south bridge 914 by a chipset bus 916. The south bridge 914 is, in turn, connected to a peripheral bus 918. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 918. In some alternative architectures, the functionality of the north bridge can be incorporated into the processor instead of using a separate north bridge chip.

In some instances, a system 900 can include an accelerator card 922 attached to the peripheral bus 918. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 924 and can be loaded into RAM 910 and/or cache 904 for use by the processor. The system 900 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

In this example, system 900 also includes network interface cards (NICs) 920 and 921 connected to the peripheral bus for providing network interfaces to external storage, such as Network Attached Storage (NAS) and other computer systems that can be used for distributed parallel processing.

Figure 10:
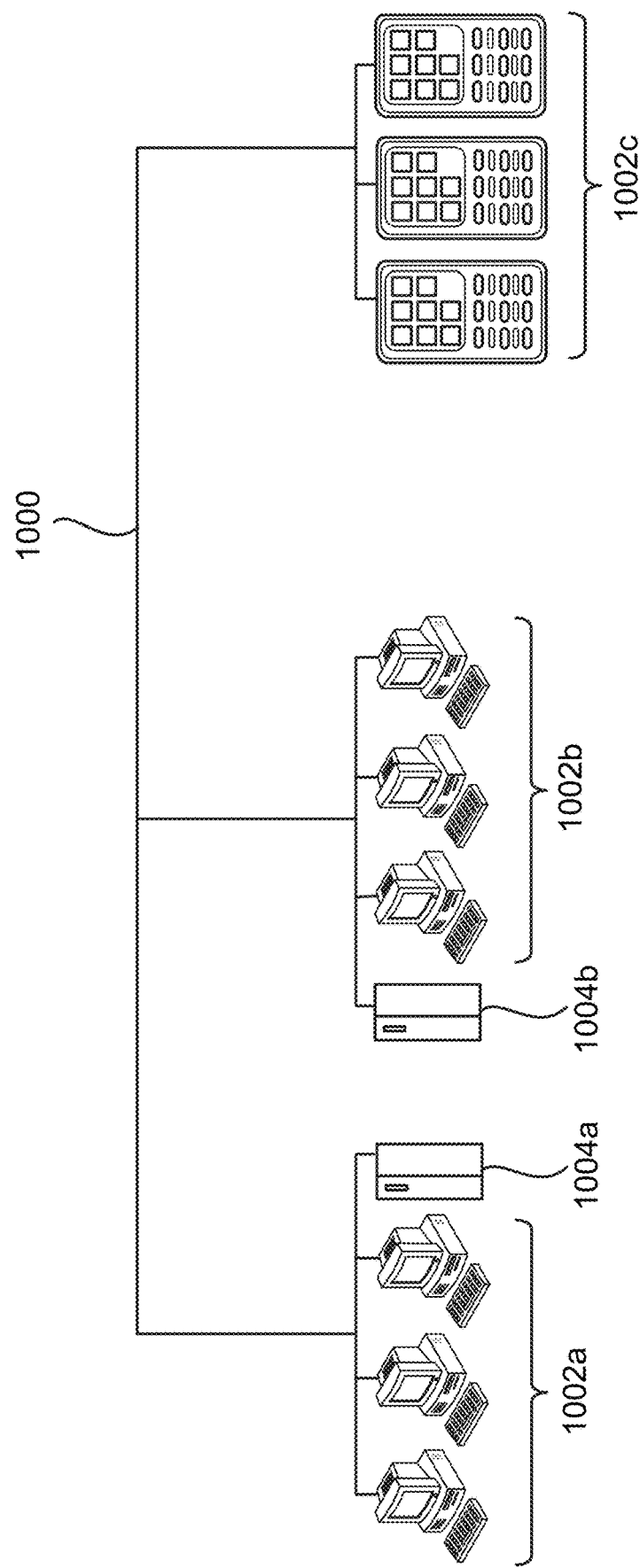
FIG. 10 is a diagram demonstrating a network configured to incorporate a plurality of computer systems, a plurality of cell phones and personal data assistants, and Network Attached Storage (NAS).

FIG. 10 is a diagram showing a network 1000 with a plurality of computer systems 1002a, and 1002b, a plurality of cell phones and personal data assistants 1002c, and Network Attached Storage (NAS) 1004a, and 1004b. In example embodiments, systems 1002a, 1002b, and 1002c can manage data storage and optimize data access for data stored in Network Attached Storage (NAS) 1004a and 1004b. A mathematical model can be used for the data and be evaluated using distributed parallel processing across computer systems 1002a, and 1002b, and cell phone and personal data assistant systems 1002c. Computer systems 1002a, and 1002b, and cell phone and personal data assistant systems 1002c can also provide parallel processing for adaptive data restructuring of the data stored in Network Attached Storage (NAS) 1004a and 1004b. FIG. 10 illustrates an example only, and a wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 11:
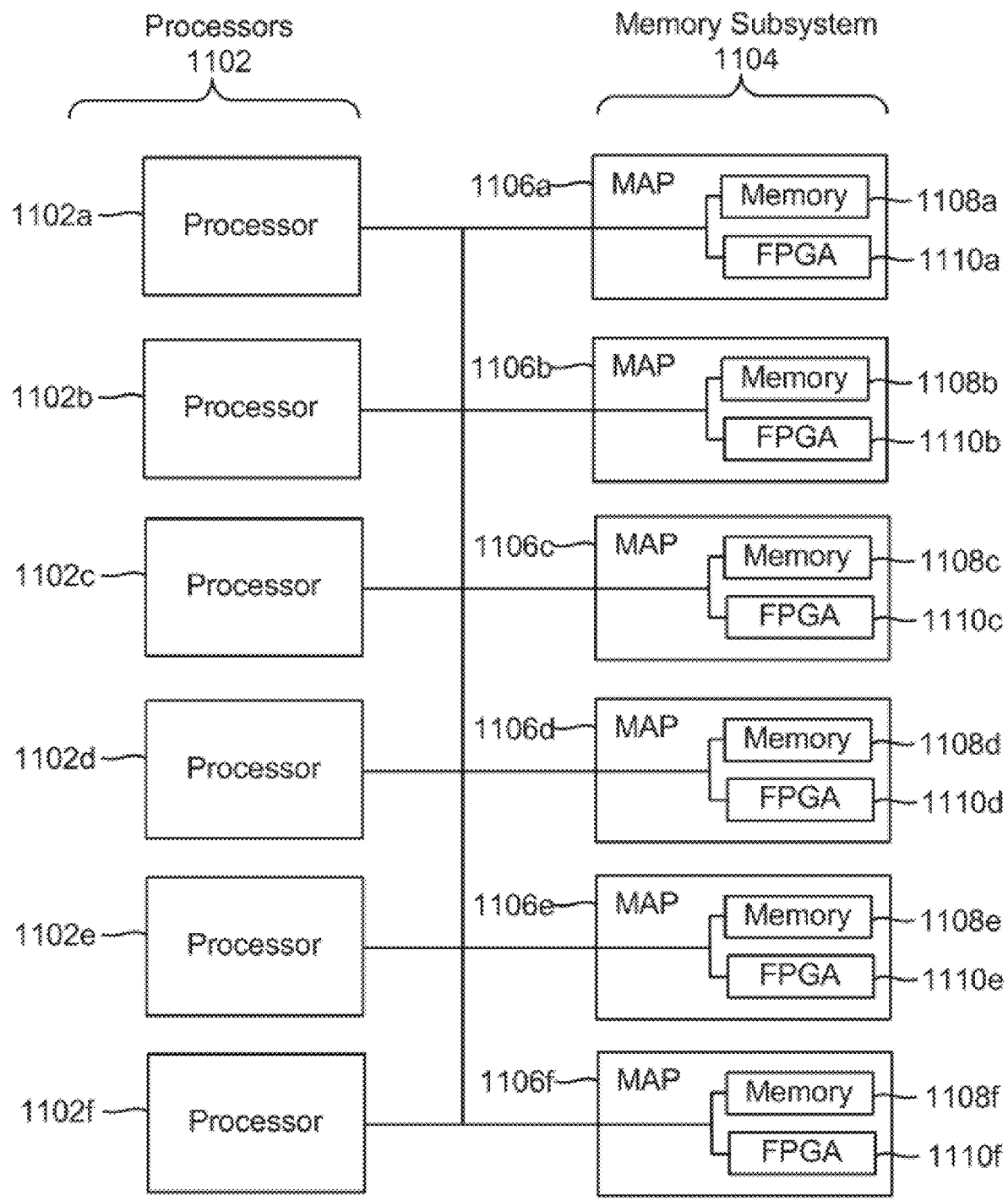
FIG. 11 is a block diagram of a multiprocessor computer system using a shared virtual address memory space.

FIG. 11 is a block diagram of a multiprocessor computer system 1100 using a shared virtual address memory space in accordance with an example embodiment. The system includes a plurality of processors 1102a-f that can access a shared memory subsystem 1104. The system incorporates a plurality of programmable hardware memory algorithm processors (MAPs) 1106a-f in the memory subsystem 1104. Each MAP 1106a-f can comprise a memory 1108a-f and one or more field programmable gate arrays (FPGAs) 1110a-f. The MAP provides a configurable functional unit and particular algorithms or portions of algorithms can be provided to the FPGAs 1110a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 1108a-f, allowing it to execute tasks independently of, and asynchronously from, the respective microprocessor 1102a-f In this configuration, a MAP can feed results directly to another MAP for pipe-lining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card.

Embodiments

Provided herein are methods for storing information, comprising: a) providing a structure comprising a surface; b) depositing at least one nucleotide on the surface, wherein the at least one nucleotide couples to a polynucleotide attached to the surface; and c) repeating step b) to synthesize a plurality of polynucleotides on the surface, wherein a storage density of unique polynucleotides on the surface is at least $100 \times 10^6$ polynucleotides per $cm^2$. Further provided herein are methods, wherein the method further comprises cleaving at least one polynucleotide from the surface, wherein the polynucleotide is dissolved in a droplet. Further provided herein are methods, wherein the method further comprises sequencing at least one polynucleotide from the surface. Further provided herein are methods, wherein the method further comprises drying the surface. Further provided herein are methods, wherein the method further comprises washing the nucleotides away from the surface. Further provided herein are methods, wherein the surface is a solid support. Further provided herein are methods, wherein the surface comprises glass, fuse silica, silicon, silicon dioxide, silicon nitride, plastics, metals, or combinations thereof.

Provided herein are methods for storing information, comprising: a) providing a structure comprising a surface; b) depositing at droplet comprising at least one nucleotide on the surface, wherein the at least one nucleotide couples to a polynucleotide attached to the surface; and c) repeating step b) to synthesize a plurality of polynucleotides on the surface, wherein the droplet has a volume of less than about 100 femtoliters.

Provided herein are methods for storing information, comprising: a) providing a structure comprising a surface; b) depositing at least one nucleotide on the surface, wherein the at least one nucleotide couples to a polynucleotide attached to the surface; and c) repeating step b) to synthesize a plurality of polynucleotides on the surface, wherein the time to repeat step b) using four different nucleotides is less than about 100 milliseconds. Further provided herein are methods, wherein the method further comprises one or more wash steps. Further provided herein are methods, wherein the method further comprises deblocking, oxidizing, washing, capping, or any combination thereof.

Provided herein are devices for storing information, comprising: a chip comprising an array of addressable loci, wherein one or more addressable loci comprise at least one electrode, a synthesis surface, and at least one fluid port, wherein the synthesis surface at each addressable loci comprises at least one polynucleotide extending from the surface, wherein a density of addressable loci on the chip is at least $100 \times 10^6$ polynucleotides per $cm^2$. Further provided herein are devices, wherein the at least one polynucleotide is about 150 to about 500 bases in length. Further provided herein are devices, wherein the at least one polynucleotide are about 200 bases in length. Further provided herein are devices, wherein the device further comprises a reagent reservoir. Further provided herein are devices, wherein the device further comprises a heating or cooling unit. Further provided herein are devices, wherein at least one addressable locus comprises a droplet. Further provided herein are devices, wherein the droplet is less than 50 micrometers in diameter.

Provided herein are methods for storing information, the method comprising: a) converting at least one item of information in a form of at least one digital sequence to at least one nucleic acid sequence; b) synthesizing a plurality of polynucleotides having predetermined sequences collectively encoding for the at least one nucleic acid sequence; c) depositing at droplet comprising at least one nucleotide on a surface, wherein the at least one nucleotide couples to a polynucleotide attached to the surface; d) repeating step c) to synthesize the plurality of polynucleotides on the surface; and e) storing the plurality of polynucleotides, wherein the droplet has a volume of less than about 100 femtoliters.

Provided herein are methods for storing information, the method comprising: a) converting at least one item of information in a form of at least one digital sequence to at least one nucleic acid sequence; b) synthesizing a plurality of polynucleotides having predetermined sequences collectively encoding for the at least one nucleic acid sequence; c) depositing at droplet comprising at least one nucleotide on a surface, wherein the at least one nucleotide couples to a polynucleotide attached to the surface; d) repeating step c) to synthesize the plurality of polynucleotides on the surface; and e) storing the plurality of polynucleotides, wherein the time to repeat step c) using four different nucleotides is less than about 100 milliseconds.

Provided herein are methods of synthesizing polynucleotides, comprising: a) providing a structure comprising a surface, wherein the surface comprises a plurality of loci for nucleotide extension; and b) synthesizing a plurality of polynucleotides extending from the surface, wherein synthesizing comprises depositing one or more reagents by applying a potential to the surface. Further provided are methods, wherein the potential is an electric potential. Further provided are methods, wherein the surface is a solid support.

Provided herein are devices for information storage using any one of the methods described herein. Provided herein are systems for information storage using any one of the methods described herein.

The following examples are set forth to illustrate more clearly the principle and practice of embodiments disclosed herein to those skilled in the art and are not to be construed as limiting the scope of any claimed embodiments. Unless otherwise stated, all parts and percentages are on a weight basis.

EXAMPLES

Example 1: Functionalization of a Device Surface

A device was functionalized to support the attachment and synthesis of a library of polynucleotides. The device surface was first wet cleaned using a piranha solution comprising 90% $H_2SO_4$ and 10% $H_2O_2$ for 20 minutes. The device was rinsed in several beakers with DI water, held under a DI water gooseneck faucet for 5 min, and dried with $N_2$. The device was subsequently soaked in $NH_4OH$ (1:100; 3 mL:300 mL) for 5 min, rinsed with DI water using a handgun, soaked in three successive beakers with DI water for 1 min each, and then rinsed again with DI water using the handgun. The device was then plasma cleaned by exposing the device surface to $O_2$. A SAMCO PC-300 instrument was used to plasma etch $O_2$ at 250 watts for 1 min in downstream mode.

The cleaned device surface was actively functionalized with a solution comprising N-(3-triethoxysilylpropyl)-4-hydroxybutyramide using a YES-1224P vapor deposition oven system with the following parameters: 0.5 to 1 torr, 60 min, 70° C., 135° C. vaporizer. The device surface was resist coated using a Brewer Science 200× spin coater. SPR™ 3612 photoresist was spin coated on the device at 2500 rpm for 40 sec. The device was pre-baked for 30 min at 90° C. on a Brewer hot plate. The device was subjected to photolithography using a Karl Suss MA6 mask aligner instrument. The device was exposed for 2.2 sec and developed for 1 min in MSF 26A. Remaining developer was rinsed with the handgun and the device soaked in water for 5 min. The device was baked for 30 min at 100° C. in the oven, followed by visual inspection for lithography defects using a Nikon L200. A cleaning process was used to remove residual resist using the SAMCO PC-300 instrument to $O_2$ plasma etch at 250 watts for 1 min.

The device surface was passively functionalized with a 100 μL solution of perfluorooctyltrichlorosilane mixed with 10 μL light mineral oil. The device was placed in a chamber, pumped for 10 min, and then the valve was closed to the pump and left to stand for 10 min. The chamber was vented to air. The device was resist stripped by performing two soaks for 5 min in 500 mL NMP at 70° C. with ultrasonication at maximum power (9 on Crest system). The device was then soaked for 5 min in 500 mL isopropanol at room temperature with ultrasonication at maximum power. The device was dipped in 300 mL of 200 proof ethanol and blown dry with $N_2$. The functionalized surface was activated to serve as a support for polynucleotide synthesis.

Example 2: Highly Accurate DNA-Based Information Storage and Assembly

Digital information was selected in the form of binary data totaling about 0.2 GB included content for the Universal Declaration of Human Rights in more than 100 languages, the top 100 books of Project Guttenberg and a seed database. The digital information was encrypted into a nucleic acid-based sequence and divided into strings. Over 10 million non-identical polynucleotides, each corresponding to a string, were synthesized on a rigid silicon surface. Each non-identical polynucleotide was under equal or less than 200 bases in length. The synthesized polynucleotides were collected and sequenced and decoded back to digital code, with 100% accuracy for the source digital information, compared to the initial at least one digital sequence.

Example 3: High Density Information Storage System

Polynucleotides are de novo synthesized by methods described herein. Following synthesis, the polynucleotides are collected into a single droplet and transferred to storage on a silicon solid support. The solid support has dimensions of 86 mm×54 mm and is 1-2 mm thick. The capacity of the solid support is 1-10 petabytes (PB) that is implemented as an addressable array of 10 gigabyte packets. The physical partitioning into packets is redundantly encoded as a leading sequence with each polynucleotide within a packet sharing a common initial sequence and any other sequence information for indexing or searching. Packets are implemented as aqueous droplets with dissolved polynucleotides, with physical redundancy of 100-1000 copies of each polynucleotide. The polynucleotide length is in a range of 100-1000 bases. Droplet volume is equivalent to spheres 40-50 μm in diameter. The solid support further comprises up to 10,000× 10,000 positions in an area less than a square inch.

Figure 12A:
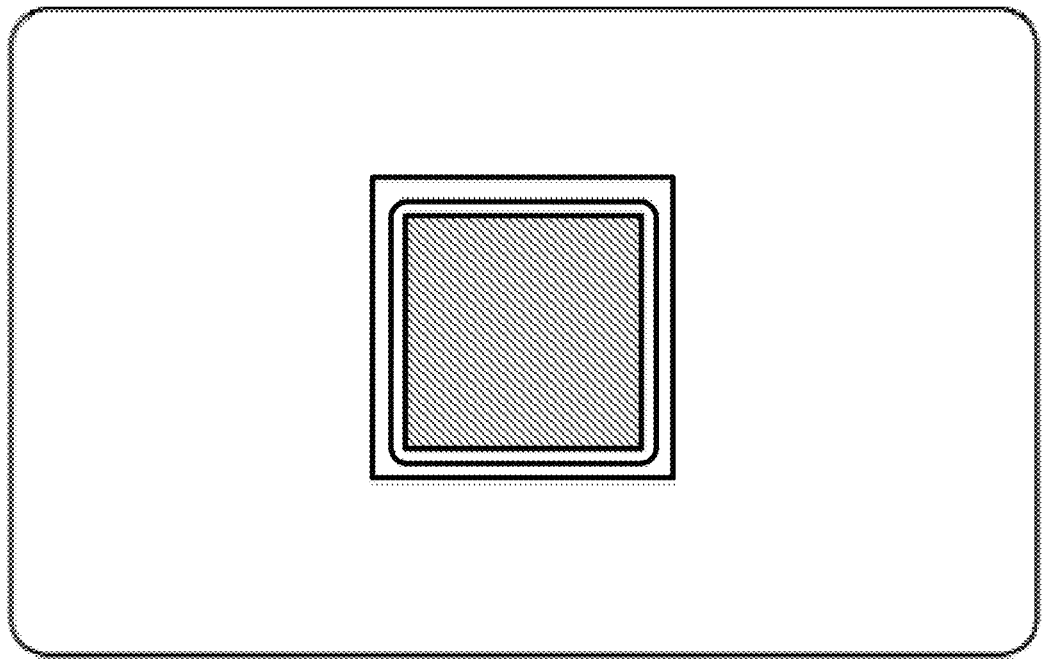
FIG. 12A is a front side of an example of a solid support array.
Figure 12B:
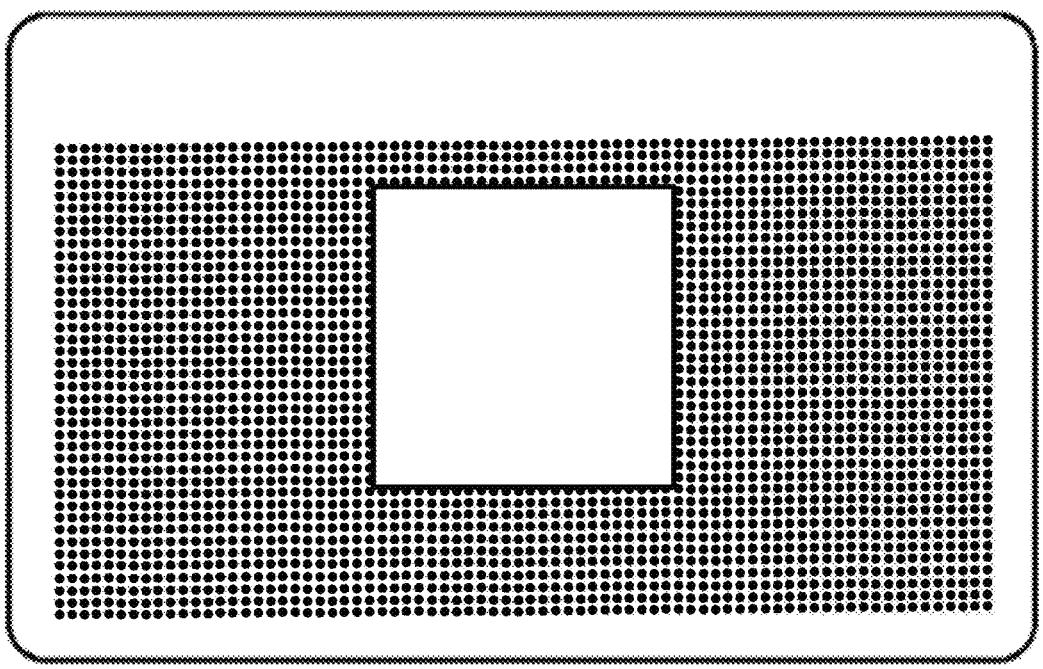
FIG. 12B is a back side of an example of a solid support array.

An exemplary solid support can be seen in FIGS. 12A-12B. FIG. 12A shows a front side of the solid support made of glass and comprising a clear window for array and fluidic ports. FIG. 12B shows a back side of the solid support that is a circuit comprising electrical contacts (LGA 1 mm pitch) and a thermal interface under the solid support area.

Following addition of the droplets to the solid support, the solid support may be dried and later resolvated for use for downstream applications. Alternatively, the solid support is dried and stored. Because the droplets within each packet comprise sequence information for indexing and searching, specific packets are retrieved from the plurality of packets based on the sequence information.

Example 4: High Density Information Storage System With Access

Figure 17:
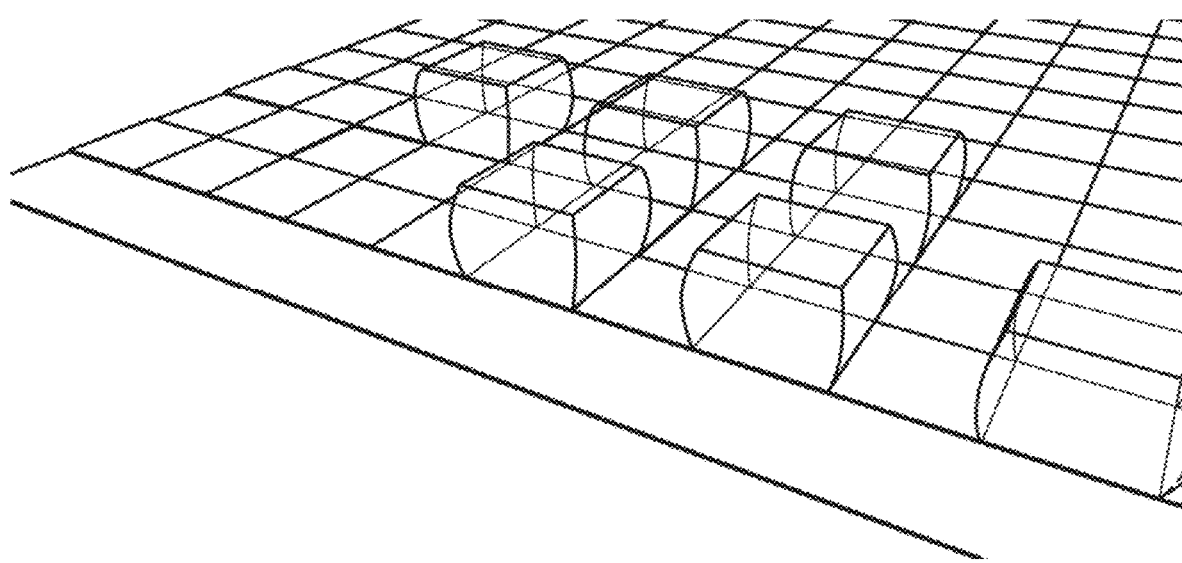
FIG. 17 depicts wells for nucleic acid synthesis or storage and a pitch distance between wells.
Figure 18:
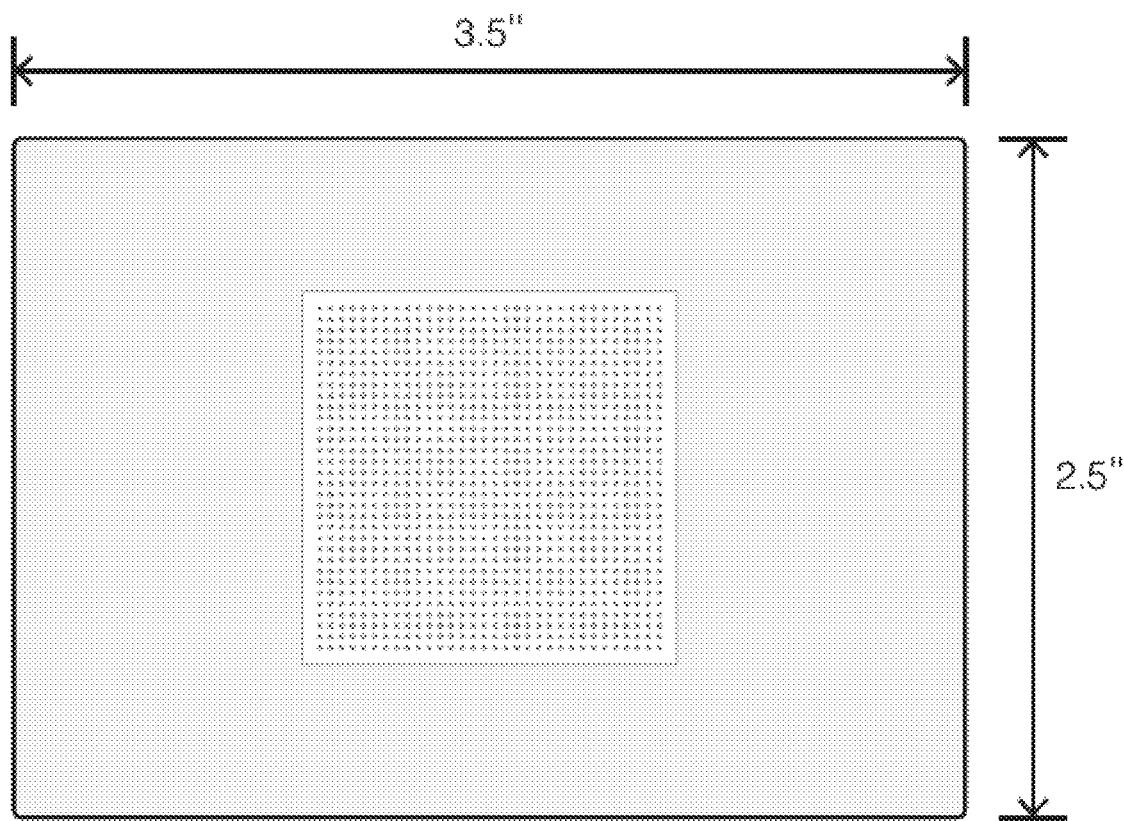
FIG. 18 illustrates an example of a solid support comprising an addressable array.

Polynucleotides are de novo synthesized by methods described herein. Following synthesis, the polynucleotides are collected into a single droplet and transferred to storage on a paper solid support. The solid support has dimensions of 3.5 inches by 2.5 inches. The capacity of the solid support is 1 petabyte that is implemented as an addressable 32×32 array comprising 1024 spots. Each spot comprises 1 terabyte pool. See e.g. FIG. 17 and FIG. 18.

At least one item of information of 10-100 megabytes is encoded in DNA and stored in 1 petabyte of data. At a later time, the 10-100 megabytes of encoded DNA is retrieved by random access of the encoded DNA and retrieving the encoded DNA from 1 terabyte pool.

Example 5: Local Control of Polynucleotide Synthesis on a Solid Support

Polynucleotides of 240 bases in length are synthesized on a solid support using the methods described herein. Polynucleotides comprising dsDNA are approximately 80 nm in length, and polynucleotides comprising ssDNA are approximately 160 nm in length. The solid support comprises an array of 500 nm (depth)×400 nm (diameter) wells (volume approximately 0.628 femtoliters). Each wells comprises an addressable locus, addressable electrodes inside the sidewalls of each well (area is 50,000 $nm^2$/electrode), and a 250 nm (diameter) surface for polynucleotide synthesis/attachment in addressable communication with a 250 nm (diameter) addressable bottom electrode. Electrodes are independently addressable. Polynucleotides are present on the synthesis surface at a density of 1 polynucleotide per 50 $nm^2$. Wells are separated by a pitch of 1.0 um. 10 nm thick sidewall electrodes (located about 100 nm above the polynucleotide surface) are charged to generate a gradient of $H^+$ ions that remove protecting groups (wherein the polynucleotide is blocked with an acid-cleavable blocking group) from the 5' OH groups on defined polynucleotides at loci on the synthesis surface. $H^+$ ions are then removed. (See FIG. 16B). A nucleoside phosphoramidite monomer is added, and the polynucleotides at unblocked sites and will be available for coupling to nucleosides. Cycles of deprotection and coupling are repeated to synthesis the polynucleotides. By applying a series of electrode-controlled masks to the surface before addition of each type of monomer, the desired polynucleotides are synthesized at exact locations on the surface in a controlled sequence.

Example 6: Local Control of Polynucleotide Synthesis on a Solid Support With Electric Fields Polynucleotides of 240 bases in length are synthesized on a solid support using the methods described herein. The solid support comprises an array of 500 nm (depth)×500 nm (diameter) wells. Each wells comprises an addressable locus, addressable electrodes inside the sidewalls of each well (area is 50,000 $nm^2$/electrode), and a 250 nm (diameter) surface for polynucleotide synthesis/attachment in addressable communication with a 250 nm (diameter) addressable bottom electrode. Electrodes are independently addressable.

Polynucleotides are present on the synthesis surface at a density of 1 polynucleotide per 50 $nm^2$. Wells are separated by a pitch of 1.0 um. A nucleoside phosphoramidite monomer is added, and the polynucleotides at unblocked sites and will be available for coupling to nucleosides. Cycles of deprotection and coupling are repeated to synthesis the polynucleotides. By applying a series of electrode-controlled masks to the surface before addition of each type of monomer, the desired polynucleotides are synthesized at exact locations on the surface in a controlled sequence. Bottom electrodes in the bottom of the well are activated, which induces release of the polynucleotides attached thereto. Sidewall electrodes are charged to generate an electric field which moves the polynucleotides out of the well. Nucleoside phosphoramidite monomers are then added which extend from reusable linkers attached to the surface, and synthesis is repeated.

Example 7: Local Control of Polynucleotide Synthesis on a Solid Support

Polynucleotides of 240 bases in length are synthesized on a solid support using the methods described herein. Polynucleotides comprising dsDNA are approximately 80 nm in length, and polynucleotides comprising ssDNA are approximately 160 nm in length. The solid support comprises an array of 100 nm diameter addressable electrodes on the surface for polynucleotide synthesis/attachment (See FIG. 19).

Polynucleotides are present on the synthesis surface at a density of 1 polynucleotide per 39.27 $nm^2$. Wells are separated by a pitch of 0.25 um. The electrodes are charged to generate a gradient of $H^+$ ions that remove protecting groups (wherein the polynucleotide is blocked with an acid-cleavable blocking group) from the 5' OH groups on defined polynucleotides at loci on the synthesis surface. $H^+$ ions are then removed. A nucleoside phosphoramidite monomer is added, and the polynucleotides at unblocked sites and will be available for coupling to nucleosides. Cycles of deprotection and coupling are repeated to synthesis the polynucleotides. By applying a series of electrode-controlled masks to the surface before addition of each type of monomer, the desired polynucleotides are synthesized at exact locations on the surface in a controlled sequence.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for storing nucleic acid-based digital information, comprising:
   a) providing a device comprising:
      a solid support, wherein the solid support comprises a plurality of wells, wherein each of the wells comprises an addressable locus comprising:
         a synthesis surface located in a bottom region of each of the wells;
         a bottom electrode in addressable communication with the synthesis surface; and
         at least one sidewall electrode located on a sidewall of each of the wells, wherein the at least one sidewall electrode is 50 nm to 200 nm from the bottom region, wherein the at least one sidewall electrode and the bottom electrode are independently addressable;
   b) providing instructions for polynucleotide synthesis;
   c) depositing at least one nucleoside on the synthesis surface, wherein the at least one nucleoside couples to a polynucleotide attached to the synthesis surface;
   d) deblocking at least one nucleoside on the synthesis surface, wherein deblocking comprises applying an electrical potential to the at least one sidewall electrode to generate a deprotection reagent; and
   e) repeating steps c) and d) to synthesize a plurality of polynucleotides on the synthesis surface, wherein the instructions comprise at least one sequence encoding for the plurality of polynucleotides, wherein the method further comprises at least one oxidation step, and wherein at least some of the polynucleotides encode for digital information.

2. The method of claim 1, wherein the solid support comprises addressable loci at a density of at least 100×$10^6$ addressable loci per $cm^2$.

3. The method of claim 1, wherein the addressable locus comprises a diameter up to about 750 nm.

4. The method of claim 1, wherein the method further comprises cleaving at least one polynucleotide from the surface, wherein the polynucleotide is dissolved in a droplet.

5. The method of claim 1, wherein the method further comprises sequencing at least one polynucleotide from the surface.

6. The method of claim 1, wherein the nucleoside comprises a nucleoside phosphoramidite.

7. The method of claim 1, wherein the method further comprises drying the surface.

8. The method of claim 1, wherein the method further comprises a cleavage step, wherein the cleavage step comprises applying an electrical potential to the bottom electrode to generate a cleavage reagent.

9. The method of claim 1, wherein the method further comprises a capping step.

10. The method of claim 1, wherein the method further comprises an oxidation step between steps c) and d).

11. The method of claim 1, wherein each of the wells comprises a longest cross-sectional diameter of 100 nm to 800 nm.

12. The method of claim 1, wherein the bottom electrode comprises an area of $10^4$ $nm^2$ to $10^5$ $nm^2$.

13. The method of claim 1, wherein at least one of the sidewall electrodes is 75 nm to 125 nm from the bottom region.

14. The method of claim 1, wherein at least one of the sidewall electrodes comprises a height of 5 nm to 25 nm.

* * * * *